US012296349B2

United States Patent
Diaz et al.

(10) Patent No.: US 12,296,349 B2
(45) Date of Patent: May 13, 2025

(54) POINT-OF-CARE ELECTROFLOTATION OF DISPERSED, LOW TOLERANCE PATHOGENS

(71) Applicant: University of Hawaii, Honolulu, HI (US)

(72) Inventors: Lena Diaz, Morrison, CO (US); Daniel Mckewn Jenkins, Honolulu, HI (US)

(73) Assignee: University of Hawaii, Honolulu, HI (US)

(*) Notice: Subject to any disclaimer, the term of this patent is extended or adjusted under 35 U.S.C. 154(b) by 1155 days.

(21) Appl. No.: 17/259,647

(22) PCT Filed: Jul. 15, 2019

(86) PCT No.: PCT/US2019/041833
§ 371 (c)(1),
(2) Date: Jan. 12, 2021

(87) PCT Pub. No.: WO2020/014704
PCT Pub. Date: Jan. 16, 2020

(65) Prior Publication Data
US 2021/0238658 A1 Aug. 5, 2021

Related U.S. Application Data

(60) Provisional application No. 62/697,574, filed on Jul. 13, 2018.

(51) Int. Cl.
*B03D 1/14* (2006.01)
*B03D 1/02* (2006.01)
(Continued)

(52) U.S. Cl.
CPC .......... *B03D 1/1437* (2013.01); *B03D 1/028* (2013.01); *C02F 1/46109* (2013.01);
(Continued)

(58) Field of Classification Search
CPC .. C02F 1/465; C02F 1/46; C02F 2001/46152; B03D 1/1437; C12Q 1/02; C12Q 1/025;
(Continued)

(56) References Cited

U.S. PATENT DOCUMENTS 1,147,989 A * 7/1915 Towne .................. C02F 1/4674
204/230.2
3,505,188 A * 4/1970 Pan .......................... C02F 1/465
210/221.1

(Continued)

FOREIGN PATENT DOCUMENTS

WO 2018083594 A1 5/2018

OTHER PUBLICATIONS

Khosla et al. "Pulsed electrogeneration of bubbles for electroflotation" Journal of Applied Electrochemistry 21 (1991) 986-990 (Year: 1991).*

(Continued)

*Primary Examiner* — Luan V Van
*Assistant Examiner* — Alexander R. Parent
(74) *Attorney, Agent, or Firm* — Riverside Law LLP

(57) ABSTRACT

The present invention relates to delivering sample preparation technologies to enhance the performance of point-of-care agricultural diagnostics by improving the capacity to detect trace contaminations of pathogenic organisms along the entire food supply chain including pre- and post-harvest processing and distribution. Sample preparation is crucial for adequate test performance of downstream diagnostics like LAMP and supports sensitive detection of bacterial contaminates. This invention increases the speed and scale of routine pathogen surveillance and the efficacy of management response and mitigation of foodborne disease outbreaks.

19 Claims, 37 Drawing Sheets

Specification includes a Sequence Listing.

(51) Int. Cl.
| | |
|---|---|
| C02F 1/461 | (2023.01) |
| C02F 1/465 | (2023.01) |
| C02F 1/52 | (2023.01) |
| C12Q 1/02 | (2006.01) |
| C12Q 1/6806 | (2018.01) |
| C12Q 1/689 | (2018.01) |
| C12R 1/19 | (2006.01) |
| G01N 33/18 | (2006.01) |

(52) U.S. Cl.
CPC ............ *C02F 1/465* (2013.01); *C02F 1/5263* (2013.01); *C12Q 1/02* (2013.01); *C12Q 1/689* (2013.01); *G01N 33/1826* (2013.01); *B03D 2203/003* (2013.01); *C02F 2001/46133* (2013.01); *C02F 2001/46152* (2013.01); *C02F 2209/008* (2013.01); *C02F 2209/06* (2013.01); *C12Q 1/6806* (2013.01); *C12R 2001/19* (2021.05)

(58) Field of Classification Search
CPC ................. C12Q 1/028; C12Q 1/1437; C12Q 2203/003; C12Q 1/689; C25B 1/04
USPC ........................................................ 205/757
See application file for complete search history.

(56) References Cited

U.S. PATENT DOCUMENTS

| | | | | |
|---|---|---|---|---|
| 4,321,125 | A * | 3/1982 | Nazarian | C02F 1/463 204/288 |
| 4,469,863 | A | 9/1984 | Ts o et al. | |
| 5,034,506 | A | 7/1991 | Summerton | |
| 5,216,141 | A | 6/1993 | Benner | |
| 5,235,033 | A | 8/1993 | Summerton | |
| 5,275,732 | A * | 1/1994 | Wang | B03D 1/1462 210/603 |
| 5,386,023 | A | 1/1995 | Sanghvi | |
| 5,602,240 | A | 2/1997 | De | |
| 5,637,684 | A | 6/1997 | Cook | |
| 5,644,048 | A | 7/1997 | Yau | |
| 5,989,407 | A * | 11/1999 | Andrews | C01B 13/10 204/266 |
| 6,824,740 | B1 | 11/2004 | Sheldon, III | |
| 8,460,520 | B2 * | 6/2013 | Rigby | C02F 1/4602 205/687 |
| 9,297,083 | B2 * | 3/2016 | Abhishek | C25B 1/04 |
| 10,053,379 | B1 * | 8/2018 | Tsantrizos | C02F 1/463 |

OTHER PUBLICATIONS

Abdel-Hamid, I., Ivnitski, D., Atanasov, P., & Wilkins, E. (1999). Flow-through immunofiltration assay system for rapid detection of *E. coli* O157: H7. Biosensors and Bioelectronics, 14(3), 309-316.
Abdel-Hamid, I., Ivnitski, D., Atanasov, P., & Wilkins, E. (1999). Highly sensitive flow-injection immunoassay system for rapid detection of bacteria. Analytica Chimica Acta, 399(1-2), 99-108.
Alam, R., & Shang, J. Q. (2016). Electrochemical model of electroflotation. Journal of Water Process Engineering, 12, 78-88.
Almutairi, Z., Ren, C. L., & Simon, L. (2012). Evaluation of polydimethylsiloxane (PDMS) surface modification approaches for microfluidic applications. Colloids and Surfaces A: Physicochemical and Engineering Aspects, 415, 406-412.
Angelopoulos, M. (2001). Conducting polymers in microelectronics. IBM journal of research and development, 45(1), 57-75.
Ballantyne, A., Forrest, G., Goosey, M., Griguceviciene, A., Juodkazyte, J., Kellner, R., . . . & Veninga, E. (2012). Advanced surface protection for improved reliability PCB systems (ASPIS). Circuit World, 38(1), 21-29.
Barany, S., & Szepesszentgyörgyi, A. (2004). Flocculation of cellular suspensions by polyelectrolytes. Advances in colloid and interface science, 111(1-2), 117-129.
Beaucage, S. L., & Iyer, R. P. (1993). The functionalization of oligonucleotides via phosphoramidite derivatives. Tetrahedron, 49(10), 1925-1963.
Bhattacharya, S., Datta, A., Berg, J. M., & Gangopadhyay, S. (2005). Studies on surface wettability of poly (dimethyl) siloxane (PDMS) and glass under oxygen-plasma treatment and correlation with bond strength. Journal of microelectromechanical systems, 14(3), 590-597.
Bhattacharya, S., Gao, Y., Korampally, V., Othman, M. T., Grant, S. A., Gangopadhyay, K., & Gangopadhyay, S. (2007). Mechanics of plasma exposed spin-on-glass (SOG) and polydimethyl siloxane (PDMS) surfaces and their impact on bond strength. Applied surface science, 253(9), 4220-4225.
Bodas, D., & Khan-Malek, C. (2006). Formation of more stable hydrophilic surfaces of PDMS by plasma and chemical treatments. Microelectronic engineering, 83(4-9), 1277-1279.
Bodas, D., & Khan-Malek, C. (2007). Hydrophilization and hydrophobic recovery of PDMS by oxygen plasma and chemical treatment—An SEM investigation. Sensors and actuators B: chemical, 123(1), 368-373.
Bouazaze, H., Cattarin, S., Huet, F., Musiani, M., & Nogueira, R. P. (2006). Electrochemical noise study of the effect of electrode surface wetting on the evolution of electrolytic hydrogen bubbles. Journal of Electroanalytical Chemistry, 597 (1), 60-68.
Breslin, C. B., Fenelon, A. M., & Conroy, K. G. (2005). Surface engineering: corrosion protection using conducting polymers. Materials & design, 26(3), 233-237.
Brill, W. K., Tang, J. Y., Ma, Y. X., & Caruthers, M. H. (1989). Synthesis of oligodeoxynucleoside phosphorodithioates via thioamidites. Journal of the American Chemical Society, 111(6), 2321-2322.
Bui, Q. V., Nam, N. D., Choi, D. H., Lee, J. B., Lee, C. Y., Kar, A., . . . & Jung, S. B. (2010). Corrosion protection of ENIG surface finishing using electrochemical methods. Materials Research Bulletin, 45(3), 305-308.
Cao, W., Easley, C. J., Ferrance, J. P., & Landers, J. P. (2006). Chitosan as a polymer for pH-induced DNA capture in a totally aqueous system. Analytical chemistry, 78(20), 7222-7228.
Carlsson, C., Jonsson, M., Norden, B., Dulay, M. T., Zare, R. N., Noolandi, J., . . . & Zielenski, J. (1996). Screening for genetic mutations [1]. Nature. 1 page.
Chandler, D. P., Brown, J., Call, D. R., Wunschel, S., Grate, J. W., Holman, D. A., . . . & Bruckner-Lea, C. J. (2001). Automated immunomagnetic separation and microarray detection of *E. coli* O157: H7 from poultry carcass rinse. International journal of food microbiology, 70(1-2), 143-154.
Chen, G. (2004). Electrochemical technologies in wastewater treatment. Separation and purification Technology, 38 (1), 11-41.
Chisti, Y. (2000). Animal-cell damage in sparged bioreactors. Trends in biotechnology, 18(10), 420-432.
Chung, Y. C., Yeh, J. Y., & Tsai, C. F. (2011). Antibacterial characteristics and activity of water-soluble chitosan derivatives prepared by the Maillard reaction. Molecules, 16(10), 8504-8514.
De Leon, A., & Advincula, R. C. (n.d.). Conducting Polymers with Superhydrophobic Effects as Anticorrosion Coating. In Intelligent coatings for corrosion control / (pp. 409-430). Butterworth-Heinemann,. https://doi.org/10.1016/B978-0-12-411467-8.00011-8.
De Mesmaeker, A., Waldner, A., Sanghvi, Y. S., & Lebreton, J. (1994). Comparison of rigid and flexible backbones in antisense oligonucleotides. Bioorganic & Medicinal Chemistry Letters, 4(3), 395-398.
Dempcy, R. O., Browne, K. A., & Bruice, T. C. (1995). Synthesis of a thymidyl pentamer of deoxyribonucleic guanidine and binding studies with DNA homopolynucleotides. Proceedings of the National Academy of Sciences, 92(13), 6097-6101.
Diaz, L. M. (2017). Point-of-Care Electroflotation of Dispersed, Low Tolerance Pathogens Improves Detection Rates by Loop Mediated Isothermal Amplification (Doctoral dissertation). 108 pages.
Diaz, L. M., Jenkins, D., Kubota, R., Walter, N., Li, Y., & McNealy, T. (2018). Electroflotation of *Escherichia coli* improves detection rates by Loop-Mediated Isothermal AMPlification. Transactions of the ASABE, 61(4), 1209-1220.

(56) References Cited

OTHER PUBLICATIONS

Duby, P. (1993). The history of progress in dimensionally stable anodes. Jom, 45(3), 41-43.
Eckstein, Oligonucleotides and Analogues: A Practical Approach, Oxford University Press, 1991, Part 1—1-78 of 344 pages.
Eckstein, Oligonucleotides and Analogues: A Practical Approach, Oxford University Press, 1991, Part 2—79-150 of 344 pages.
Eckstein, Oligonucleotides and Analogues: A Practical Approach, Oxford University Press, 1991, Part 3—151-344 of 344 pages.
Egholm, M., Buchardt, O., Christensen, L., Behrens, C., Freier, S. M., Driver, D. A., . . . & Nielsen, P. E. (1993). PNA hybridizes to complementary oligonucleotides obeying the Watson-Crick hydrogen-bonding rules. Nature, 365(6446), 566-568.
Egholm, M., Buchardt, O., Nielsen, P. E., & Berg, R. H. (1992). Peptide nucleic acids (PNA). Oligonucleotide analogs with an achiral peptide backbone. Journal of the American Chemical Society, 114(5), 1895-1897.
Elias, C. B., Desai, R. B., Patole, M. S., Joshi, J. B., & Mashelkar, R. A. (1995). Turbulent shear stress—effect on mammalian cell culture and measurement using laser Doppler anemometer. Chemical Engineering Science, 50(15), 2431-2440.
Fan, W., Wu, X., Ding, B., Gao, J., Cai, Z., Zhang, W., . . . & Gao, S. (2012). Degradable gene delivery systems based on Pluronics-modified low-molecular-weight polyethylenimine: preparation, characterization, intracellular trafficking, and cellular distribution. International journal of nanomedicine, 1127-1138.
Fang, R., Li, X., Hu, L., You, Q., Li, J., Wu, J., . . . & Gao, Q. (2009). Cross-priming amplification for rapid detection of *Mycobacterium tuberculosis* in sputum specimens. Journal of clinical microbiology, 47(3), 845-847.
Farías, T., de Ménorval, L. C., Zajac, J., & Rivera, A. (2009). Solubilization of drugs by cationic surfactants micelles: Conductivity and 1H NMR experiments. Colloids and Surfaces A: Physicochemical and Engineering Aspects, 345(1-3), 51-57.
Fu, H., Lee, D., Lee, J., Tong, G., Lee, S., Singh, P., . . . & Jiang, G. (Oct. 2015). Creep corrosion failure analysis on ENIG printed circuit boards. In 2015 10th International Microsystems, Packaging, Assembly and Circuits Technology Conference (IMPACT) (pp. 124-129). IEEE.
Fu, Z., Rogelj, S., & Kieft, T. L. (2005). Rapid detection of *Escherichia coli* O157: H7 by immunomagnetic separation and real-time PCR. International journal of food microbiology, 99(1), 47-57.
G. H. 2009. Nucleic Acid Sample Preparation for Downstream Analyses. In: The Federation of European Biochemical Societies Journal. vol. 28-9624-0. p. 1-171.
Gao, X., & Jeffs, P. W. (1994). Unusual Conformation of a 3'-thioformacetal Linkage in a DNA Duplex. Journal of Biomolecular NMR, 4(1), 17-34.
Garg, S., Wang, L., & Schenk, P. M. (2014). Effective harvesting of low surface-hydrophobicity microalgae by froth flotation. Bioresource technology, 159, 437-441.
Ghernaout, D., Benblidia, C., & Khemici, F. (2015). Microalgae removal from Ghrib Dam (Ain Defla, Algeria) water by electroflotation using stainless steel electrodes. Desalination and Water Treatment, 54(12), 3328-3337.
Ghosh, M., Ganguli, A., & Pathak, S. (2009). Application of a novel biopolymer for removal of *Salmonella* from poultry wastewater. Environmental Technology, 30(4), 337-344.
Gonzales, L. V., Veneu, D. M., Monte, M. B. D. M., & Torem, M. L. (2012). Measurement and analysis of micro-bubbles produced in electroflotation. In 67th ABM International Congress. Rio de Janeiro, RJ, Brazil (pp. 2136-2146).
Gregory, J., & Barany, S. (2011). Adsorption and flocculation by polymers and polymer mixtures. Advances in colloid and interface science, 169(1), 1-12.
Halladay, D., Resnik, R. (1963). Physics for Students of Science and Engineering. John Wiley and Sons. Part 1 (1-150 pages).
Halladay, D., Resnik, R. (1963). Physics for Students of Science and Engineering. John Wiley and Sons. Part 2 (151-300 pages).
Halladay, D., Resnik, R. (1963). Physics for Students of Science and Engineering. John Wiley and Sons. Part 3 (301-499 pages).
Halladay, D., Resnik, R. (1963). Physics for Students of Science and Engineering. John Wiley and Sons. Part 3 (500-620 pages).
Halldorsson, S., Lucumi, E., Gómez-Sjöberg, R., & Fleming, R. M. (2015). Advantages and challenges of microfluidic cell culture in polydimethylsiloxane devices. Biosensors and Bioelectronics, 63, 218-231.
Hemmilä, S., Cauich-Rodríguez, J. V., Kreutzer, J., & Kallio, P. (2012). Rapid, simple, and cost-effective treatments to achieve long-term hydrophilic PDMS surfaces. Applied Surface Science, 258(24), 9864-9875.
Hoffmann, S., Batz, M. B., & Morris Jr, J. G. (2012). Annual cost of illness and quality-adjusted life year losses in the United States due to 14 foodborne pathogens. Journal of food protection, 75(7), 1292-1302.
Horn, T., Chaturvedi, S., Balasubramaniam, T. N., & Letsinger, R. L. (1996). Oligonucleotides with alternating anionic and cationic phosphoramidate linkages: Synthesis and hybridization of stereo-uniform isomers. Tetrahedron letters, 37(6), 743-746.
Hu, S., Ren, X., Bachman, M., Sims, C. E., Li, G. P., & Allbritton, N. (2002). Surface modification of poly (dimethylsiloxane) microfluidic devices by ultraviolet polymer grafting. Analytical chemistry, 74(16), 4117-4123.
Jacobs, A., Lafolie, F., Herry, J. M., & Debroux, M. (2007). Kinetic adhesion of bacterial cells to sand: cell surface properties and adhesion rate. Colloids and Surfaces B: Biointerfaces, 59(1), 35-45.
Jarvis, P., Jefferson, B., Gregory, J., & Parsons, S. A. (2005). A review of floc strength and breakage. Water Res., 39(14), 3121-3137. https://doi.org/10.1016/j.watres.2005.05.022.
Jenkins, G. N., & Turner, N. J. (1995). The biosynthesis of carbocyclic nucleosides. Chemical Society Reviews, 24(3), 169-176.
Joshi, J. B., Elias, C. B., & Patole, M. S. (1996). Role of hydrodynamic shear in the cultivation of animal, plant and microbial cells. The Chemical Engineering Journal and the Biochemical Engineering Journal, 62(2), 121-141.
Jung, P. M., Histand, G., & Letsinger, R. L. (1994). Hybridization of alternating cationic/anionic oligonucleotides to RNA segments. Nucleosides, Nucleotides & Nucleic Acids, 13(6-7), 1597-1605.
Karim, M. N., Graham, H., Han, B., & Cibulskas, A. (2008). Flocculation enhanced microfiltration of *Escherichia coli* lysate. Biochemical engineering journal, 40(3), 512-519.
Khosla, A. (2012). Nanoparticle-doped electrically-conducting polymers for flexible nano-micro Systems. The Electrochemical Society Interface, 21(3-4), 67.
Kong, M., Chen, X. G., Xing, K., & Park, H. J. (2010). Antimicrobial properties of chitosan and mode of action: a state of the art review. International journal of food microbiology, 144(1), 51-63.
Koshkin, A. A., Nielsen, P., Meldgaard, M., Rajwanshi, V. K., Singh, S. K., & Wengel, J. (1998). LNA (locked nucleic acid): an RNA mimic forming exceedingly stable LNA: LNA duplexes. Journal of the American Chemical Society, 120 (50), 13252-13253.
Kubota, R., & Jenkins, D. M. (2015). Real-time duplex applications of loop-mediated AMPlification (LAMP) by assimilating probes. International Journal of Molecular Sciences, 16(3), 4786-4799.
Kubota, R., Alvarez, A. M., Su, W. W., & Jenkins, D. M. (2011). FRET-based assimilating probe for sequence-specific real-time monitoring of loop-mediated isothermal amplification (LAMP). Biological Engineering Transactions, 4(2), 81-100.
Kurniawati, H. A., Ismadji, S., & Liu, J. C. (2014). Microalgae harvesting by flotation using natural saponin and chitosan. Bioresource technology, 166, 429-434.
Kyzas, G. Z., & Matis, K. A. (2014). Flotation of biological materials. Processes, 2(1), 293-310.
Lautkaski, R. (2005). Pressure rise in confined gas explosions. Dec. 30, 2005). https://www. vtt. fi/inf/julkaisut/muut/2005/PRO1_P1026_05. pdf.
Lee, H. Y., Barber, C., & Minerick, A. R. (2014). Improving electrokinetic microdevice stability by controlling electrolysis bubbles. Electrophoresis, 35(12-13), 1782-1789.
Letsinger, R. L., & Mungall, W. S. (1970). Nucleotide chemistry. XVI. Phosporamidate analogs of oligonucleotides. The Journal of organic chemistry, 35(11), 3800-3803.

(56) References Cited

OTHER PUBLICATIONS

Letsinger, R. L., Bach, S. A., & Eadie, J. S. (1986). Effects of pendant groups at phosphorus on binding properties of d-ApA analogues. Nucleic acids research, 14(8), 3487-3499.

Letsinger, R. L., Singman, C. N., Histand, G., & Salunkhe, M. (1988). Cationic oligonucleotides. Journal of the American Chemical Society, 110(13), 4470-4471.

Liang, C., Chu, Y., Cheng, S., Wu, H., Kajiyama, T., Kambara, H., & Zhou, G. (2012). Multiplex loop-mediated isothermal amplification detection by sequence-based barcodes coupled with nicking endonuclease-mediated pyrosequencing. Analytical chemistry, 84(8), 3758-3763.

Lide DR. 1994. Dissociation Constants, Ionic Conductivities. In: CRC Handbook of Chemistry and Physics. 74th ed. CRC Press. p. 8-47, 5-91.

Lu, J., Gerke, T. L., Buse, H. Y., & Ashbolt, N. J. (2014). Development of an *Escherichia coli* K12-specific quantitative polymerase chain reaction assay and DNA isolation suited to biofilms associated with iron drinking water pipe corrosion products. Journal of water and health, 12(4), 763-771.

Luo, C., Meng, F., & Francis, A. (2006). Fabrication and application of silicon-reinforced PDMS masters. Microelectronics journal, 37(10), 1036-1046.

Luo, Y., Huang, B., Wu, H., & Zare, R. N. (2006). Controlling electroosmotic flow in poly (dimethylsiloxane) separation channels by means of prepolymer additives. Analytical Chemistry, 78(13), 4588-4592.

Ma, N., Chalmers, J. J., Auniņš, J. G., Zhou, W., & Xie, L. (2004). Quantitative studies of cell-bubble interactions and cell damage at different Pluronic F-68 and cell concentrations. Biotechnology progress, 20(4), 1183-1191.

Mag, M., Silke, L., & Engels, J. W. (1991). Synthesis and selective cleavage of an oligodeoxynucleotide containing a bridged internucleotide 5'-phosphorothioate linkage. Nucleic acids research, 19(7), 1437-1441.

Mandal, P. K., Biswas, A. K., Choi, K., & Pal, U. K. (2011). Methods for Rapid Detection of Foodborne Pathogens: An Overview. American Journal of Food Technology, 6(2), 87-102.

Maron, P. A., Schimann, H., Ranjard, L., Brothier, E., Domenach, A. M., Lensi, R., & Nazaret, S. (2006). Evaluation of quantitative and qualitative recovery of bacterial communities from different soil types by density gradient centrifugation. European Journal of Soil Biology, 42(2), 65-73.

Martzy, R., Kolm, C., Brunner, K., Mach, R. L., Krska, R., Šinkovec, H., . . . & Reischer, G. H. (2017). A loop-mediated isothermal amplification (LAMP) assay for the rapid detection of *Enterococcus* spp. in water. Water research, 122, 62-69.

Mattes, J., Yang, M., & Foster, P. S. (2007). Regulation of microRNA by antagomirs: a new class of pharmacological antagonists for the specific regulation of gene function?. American journal of respiratory cell and molecular biology, 36 (1), 8-12.

Meier, C., & Engels, J. W. (1992). Peptide Nucleic Acids (PNAs)— Unusual Properties of Nonionic Oligonucleotide Analogues. Angewandte Chemie International Edition in English, 31(8), 1008-1010.

Metters, J. P., Gomez-Mingot, M., Iniesta, J., Kadara, R. O., & Banks, C. E. (2013). The fabrication of novel screen printed single-walled carbon nanotube electrodes: electroanalytical applications. Sensors and Actuators B: Chemical, 177, 1043-1052.

Metters, J. P., Kadara, R. O., & Banks, C. E. (2012). Electroanalytical properties of screen printed graphite microband electrodes. Sensors and Actuators B: Chemical, 169, 136-143.

Montemayor, L. C. (Sep. 2002). Electrically Conductive Silicone Adhesive. In Proceedings of SMTA International Conference. 7 pages.

Montes-Atenas, G., Garcia-Garcia, F. J., Mermillod-Blondin, R., & Montes, S. (2010). Effect of suspension chemistry onto voltage drop: Application to electro-flotation. Powder Technology, 204(1), 1-10.

Moscicki A, Sobierajski T, Falat T, Felba J. The post-curing technology for conductivity improvement of low-viscosity electrically conductive adhesives. :2-5. 2013. 18 pages.

Moscicki, A., Smolarek, A., Felba, J., & Falat, T. (2013). Properties of different types of protective layers on silver metallic nanoparticles for ink-jet printing technique. by JE Morris and K. Iniewski, CRC Press Taylor & Francis Group, 303-320.

Mozes, N., Amory, D. E., Leonard, A. J., & Rouxcet, P. G. (1989). Surface properties of microbial cells and their role in adhesion and flocculation. Colloids and surfaces, 42(2), 313-329.

Murugananthan, M., Raju, G. B., & Prabhakar, S. (2004). Separation of pollutants from tannery effluents by electro flotation. Separation and Purification Technology, 40(1), 69-75.

Nagai, N., Takeuchi, M., Kimura, T., & Oka, T. (2003). Existence of optimum space between electrodes on hydrogen production by water electrolysis. International journal of hydrogen energy, 28(1), 35-41.

Nagamine, K., Hase, T., & Notomi, T. J. M. C. P. (2002). Accelerated reaction by loop-mediated isothermal amplification using loop primers. Molecular and cellular probes, 16(3), 223-229.

Nguyen, A. V., & Evans, G. M. (2002). The liquid flow force on a particle in the bubble-particle interaction in flotation. Journal of colloid and interface science, 246(1), 100-104.

Notomi, T., Okayama, H., Masubuchi, H., Yonekawa, T., Watanabe, K., Amino, N., & Hase, T. (2000). Loop-mediated isothermal amplification of DNA. Nucleic acids research, 28(12), e63-e63.

Osada, H., & Takahashi, T. (2007). MicroRNAs in biological processes and carcinogenesis. Carcinogenesis, 28(1), 2-12.

Pearson, C. R., Heng, M., Gebert, M., & Glatz, C. E. (2004). Zeta potential as a measure of polyelectrolyte flocculation and the effect of polymer dosing conditions on cell removal from fermentation broth. Biotechnology and bioengineering, 87(1), 54-60.

Percino, M. J., Chapela, V. M. (2013). Conducting Polymers, in Handbook of Polymer Synthesis, Characterization, and Processing. E. Saldívar-Guerra and E. Vivaldo-Lima, editor. Inc., Hoboken, NJ, USA: John Wiley & Sons. 22 pages.

Qin, C., Li, H., Xiao, Q., Liu, Y., Zhu, J., & Du, Y. (2006). Water-solubility of chitosan and its antimicrobial activity. Carbohydrate polymers, 63(3), 367-374.

Rawls, R. L. (1997). Optimistic about antisense. Chemical & engineering news, 75(22), 35-39.

Rinaudo, M. (2006). Chitin and chitosan: Properties and applications. Progress in polymer science, 31(7), 603-632.

Rohwerder, M., & Michalik, A. (2007). Conducting polymers for corrosion protection: What makes the difference between failure and success?. Electrochimica Acta, 53(3), 1300-1313.

Sahoo, P. R., Sethy, K., Mohapatra, S., & Panda, D. (2016). Loop mediated isothermal amplification: An innovative gene amplification technique for animal diseases. Veterinary world, 9(5), 465.

Salahinejad, E., Eslami-Farsani, R., & Tayebi, L. (2017). Corrosion failure analysis of printed circuit boards exposed to H2S-containing humid environments. Engineering Failure Analysis, 79, 538-546.

Sanghvi, Y. S., & Cook, P. D. (Eds.). (1994). Carbohydrate modifications in antisense research. American Chemical Society. 1 page.

Santos, D. M., Sequeira, C. A., & Figueiredo, J. L. (2013). Hydrogen production by alkaline water electrolysis. Química Nova, 36, 1176-1193.

Sawai, H. (1984). Synthesis and properties of oligoadenylic acids containing 2'-5'phosphoramide linkage. Chemistry Letters, (5), 805-808.

Scharff, R. L. (2012). Economic burden from health losses due to foodborne illness in the United States. Journal of food protection, 75(1), 123-131.

Scheithauer, U. (1991). Application of the analytical methods REM/EDX, AES and SNMS to a chlorine induced aluminium corrosion. Fresenius' journal of analytical chemistry, 341, 445-448.

Sharma, P. K., Gibcus, M. J., van der Mei, H. C., & Busscher, H. J. (2005). Influence of fluid shear and microbubbles on bacterial detachment from a surface. Applied and environmental microbiology, 71(7), 3668-3673.

Sowana, D. D., Williams, D. R. G., Dunlop, E. H., Dally, B. B., O'Neill, B. K., & Fletcher, D. F. (2001). Turbulent shear stress

(56) References Cited

OTHER PUBLICATIONS effects on plant cell suspension cultures. Chemical Engineering Research and Design, 79(8), 867-875.

Sprinzl, M., Sternbach, H., Von Der Haar, F., & Cramer, F. (1977). Enzymatic Incorporation of ATP and CTP Analogues into the 3' End of tRNA. European journal of biochemistry, 81(3), 579-589.

Stevens, K. A., & Jaykus, L. A. (2004). Bacterial separation and concentration from complex sample matrices: a review. Critical reviews in microbiology, 30(1), 7-24.

Strand, S. P., Nordengen, T., & Østgaard, K. (2002). Efficiency of chitosans applied for flocculation of different bacteria. Water Research, 36(19), 4745-4752.

Strand, S. P., Vandvik, M. S., Vårum, K. M., & Østgaard, K. (2001). Screening of chitosans and conditions for bacterial flocculation. Biomacromolecules, 2(1), 126-133.

Strand, S. P., Vårum, K. M., & Østgaard, K. (2003). Interactions between chitosans and bacterial suspensions: adsorption and flocculation. Colloids and Surfaces B: Biointerfaces, 27(1), 71-81.

Sugimoto, M., Morimoto, M., Sashiwa, H., Saimoto, H., & Shigemasa, Y. (1998). Preparation and characterization of water-soluble chitin and chitosan derivatives. Carbohydrate polymers, 36(1), 49-59.

Švancara, I., Vytřas, K., Kalcher, K., Walcarius, A., & Wang, J. (2009). Carbon paste electrodes in facts, numbers, and notes: a review on the occasion of the 50-years jubilee of carbon paste in electrochemistry and electroanalysis. Electroanalysis: An International Journal Devoted to Fundamental and Practical Aspects of Electroanalysis, 21(1), 7-28.

Szpyrkowicz, L. (2005). Hydrodynamic effects on the performance of electro-coagulation/electro-flotation for the removal of dyes from textile wastewater. Industrial & engineering chemistry research, 44(20), 7844-7853.

Teh, C. S. J., Chua, K. H., Lim, Y. A. L., Lee, S. C., & Thong, K. L. (2014). Loop-mediated isothermal amplification assay for detection of generic and verocytotoxin-producing *Escherichia coli* among indigenous individuals in Malaysia. The Scientific World Journal, 2014. 7 pages.

Tharmalingam, T., Ghebeh, H., Wuerz, T., & Butler, M. (2008). Pluronic enhances the robustness and reduces the cell attachment of mammalian cells. Molecular biotechnology, 39, 167-177.

Thatcher, S. A. (2015). DNA/RNA preparation for molecular detection. Clinical chemistry, 61(1), 89-99.

Von Kiedrowski, G., Wlotzka, B., Helbing, J., Matzen, M., & Jordan, S. (1991). Parabolic Growth of a Self-Replicating Hexadeoxynucleotide Bearing a 3'-5'-Phosphoamidate Linkage. Angewandte Chemie International Edition in English, 30(4), 423-426.

Walls, P. L., Bird, J. C., & Bourouiba, L. (2014). Moving with bubbles: a review of the interactions between bubbles and the microorganisms that surround them. American Zoologist, 54(6), 1014-1025.

Wang, H., & Turechek, W. W. (2016). A loop-mediated isothermal amplification assay and sample preparation procedure for sensitive detection of Xanthomonas fragariae in strawberry. PLoS One, 11(1), e0147122. 21 pages.

Wang, Z., Wang, J., Yue, T., Yuan, Y., Cai, R., & Niu, C. (2013). Immunomagnetic separation combined with polymerase chain reaction for the detection of Alicyclobacillus acidoterrestris in apple juice. PLoS One, 8(12), e82376. https://doi.org/10.1371/journal.pone.0082376.

Wessling, B., & Posdorfer, J. (1999). Corrosion prevention with an organic metal (polyaniline): corrosion test results. Electrochimica Acta, 44(12), 2139-2147.

Wilson, I. G. (1997). Inhibition and facilitation of nucleic acid amplification. Applied and environmental microbiology, 63(10), 3741-3751.

Xu, G., Hu, L., Zhong, H., Wang, H., Yusa, S. I., Weiss, T. C., . . . & You, Q. (2012). Cross priming amplification: mechanism and optimization for isothermal DNA amplification. Scientific reports, 2(1), 246.

Yang, Z., Yuan, B., Huang, X., Zhou, J., Cai, J., Yang, H., . . . & Cheng, R. (2012). Evaluation of the flocculation performance of carboxymethyl chitosan-graft-polyacrylamide, a novel amphoteric chemically bonded composite flocculant. Water Research, 46(1), 107-114.

You, D. J., Geshell, K. J., & Yoon, J. Y. (2011). Direct and sensitive detection of foodborne pathogens within fresh produce samples using a field-deployable handheld device. Biosensors and Bioelectronics, 28(1), 399-406.

Zarras, P., Anderson, N., Webber, C., Irvin, D. J., Irvin, J. A., Guenthner, A., & Stenger-Smith, J. D. (2003). Progress in using conductive polymers as corrosion-inhibiting coatings. Radiation Physics and Chemistry, 68(3-4), 387-394.

Zhang, B., Wang, Q., & Pan, X. (2007). MicroRNAs and their regulatory roles in animals and plants. Journal of cellular physiology, 210(2), 279-289.

Zhang, J., Liang, Z., Hreid, T., Guo, W., & Yuan, Z. (2012). Fabrication and investigation of a new copper-doped screen-printable carbon paste's conductive mechanism by AFM. RSC advances, 2(11), 4787-4791.

Zhao, L. H., Lee, J., & Sen, P. N. (2012). Long-term retention of hydrophilic behavior of plasma treated polydimethylsiloxane (PDMS) surfaces stored under water and Luria-Bertani broth. Sensors and Actuators A: Physical, 181, 33-42.

Zhao, Y., Gu, S., Gong, K., Zheng, J., Wang, J., & Yan, Y. (2017). Iodine redox-mediated electrolysis for energy-efficient chlorine regeneration from gaseous HCl. Journal of the Electrochemical Society, 164(7), E138.

Zhou, W., Gao, L., Cheng, W., Chen, L., Wang, J., Wang, H., . . . & Liu, T. (2016). Electro-flotation of *Chlorella* sp. assisted with flocculation by chitosan. Algal research, 18, 7-14.

Zimmerman, W. B., Tesar, V., Butler, S., & Bandulasena, H. C. (2008). Microbubble generation. Recent patents on engineering, 2(1), 1-8.

Zita, A., & Hermansson, M. (1997). Effects of bacterial cell surface structures and hydrophobicity on attachment to activated sludge flocs. Applied and environmental microbiology, 63(3), 1168-1170.

\* cited by examiner

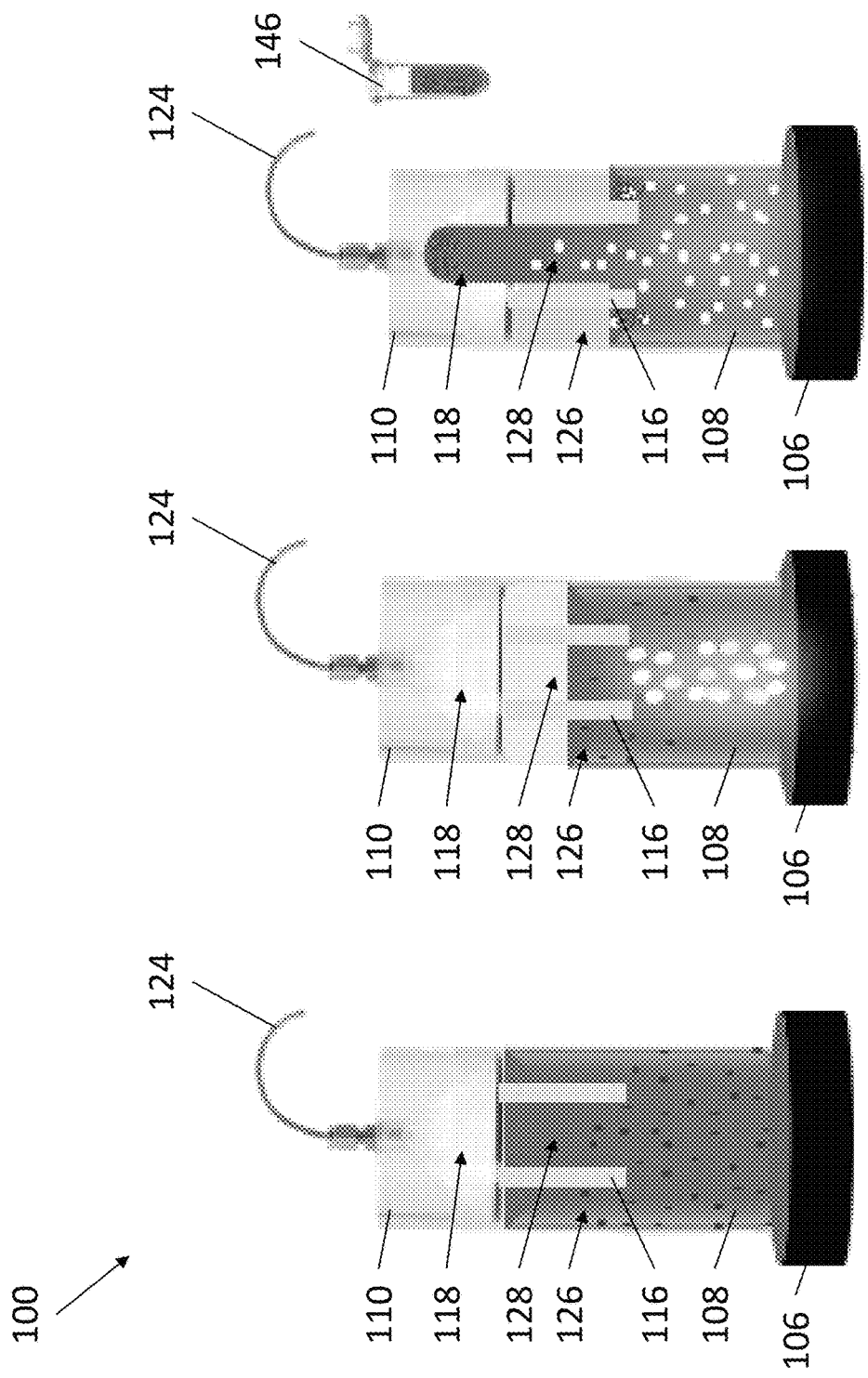

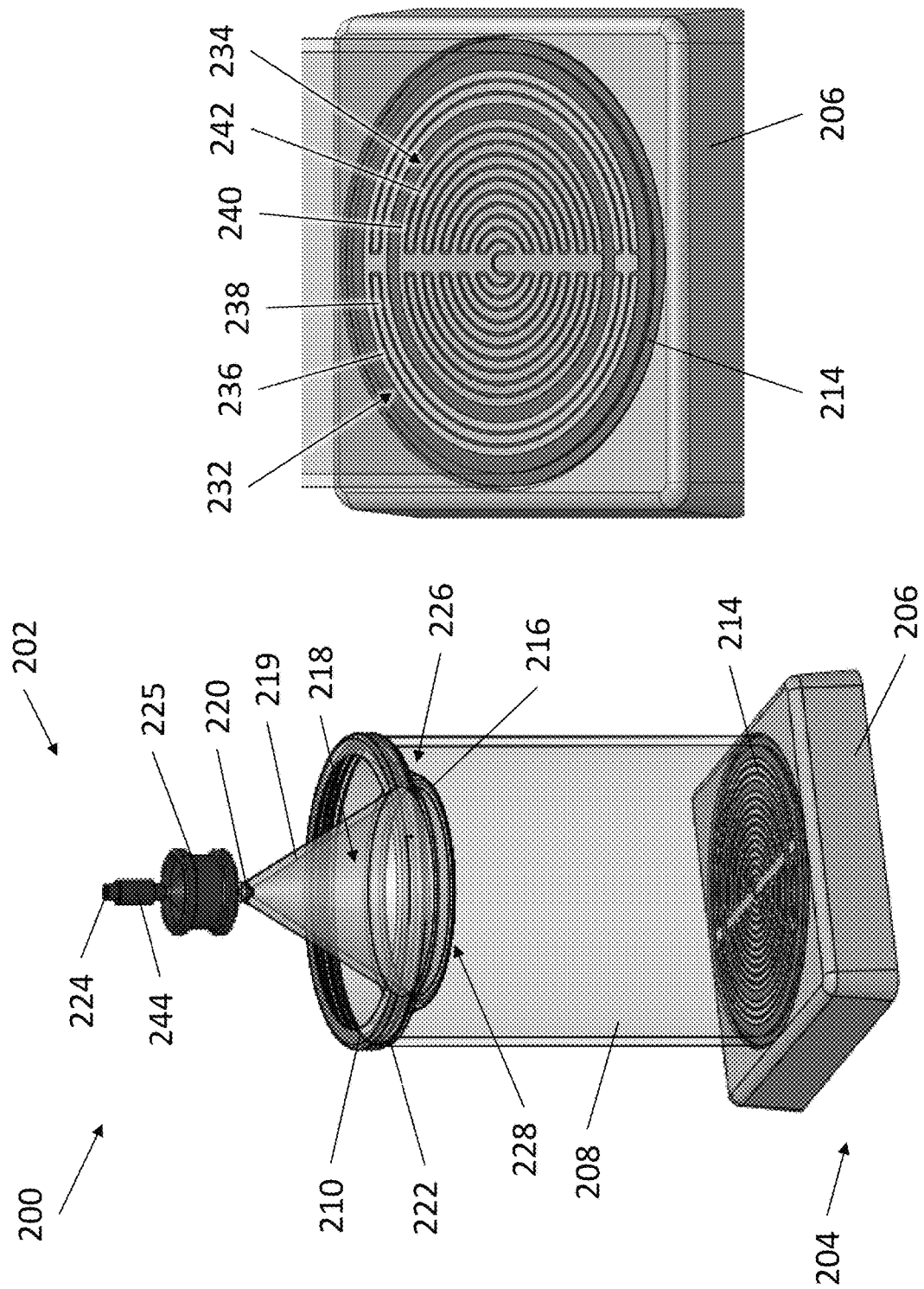

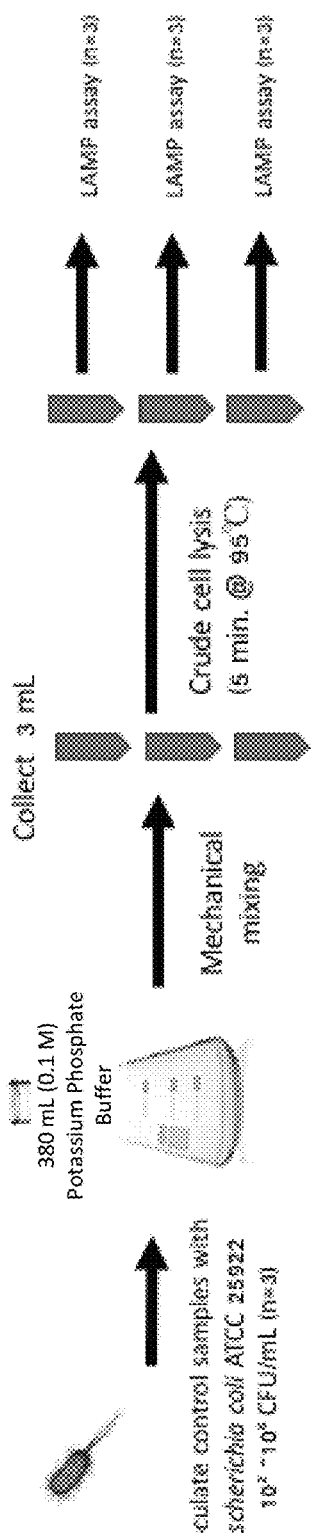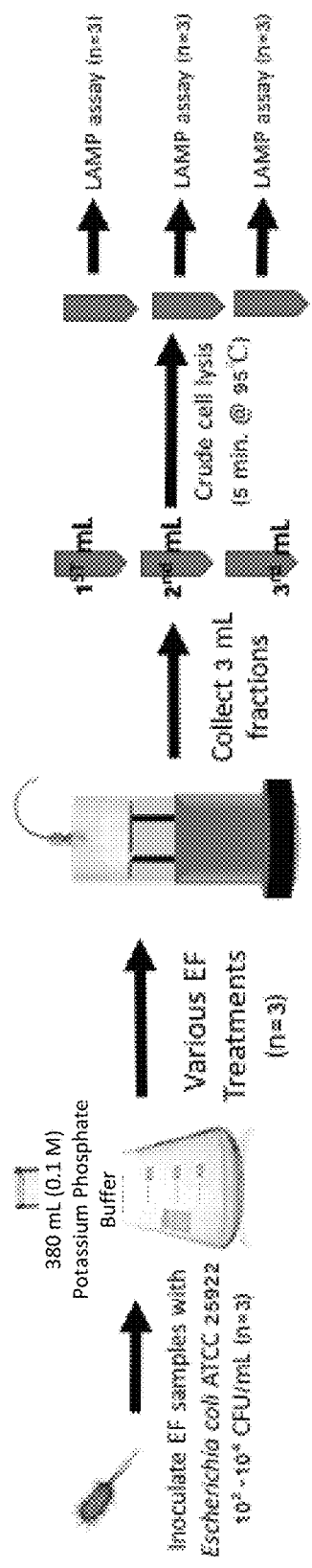
FIG. 14A Control
FIG. 14B Experimental

Mix

40 μm

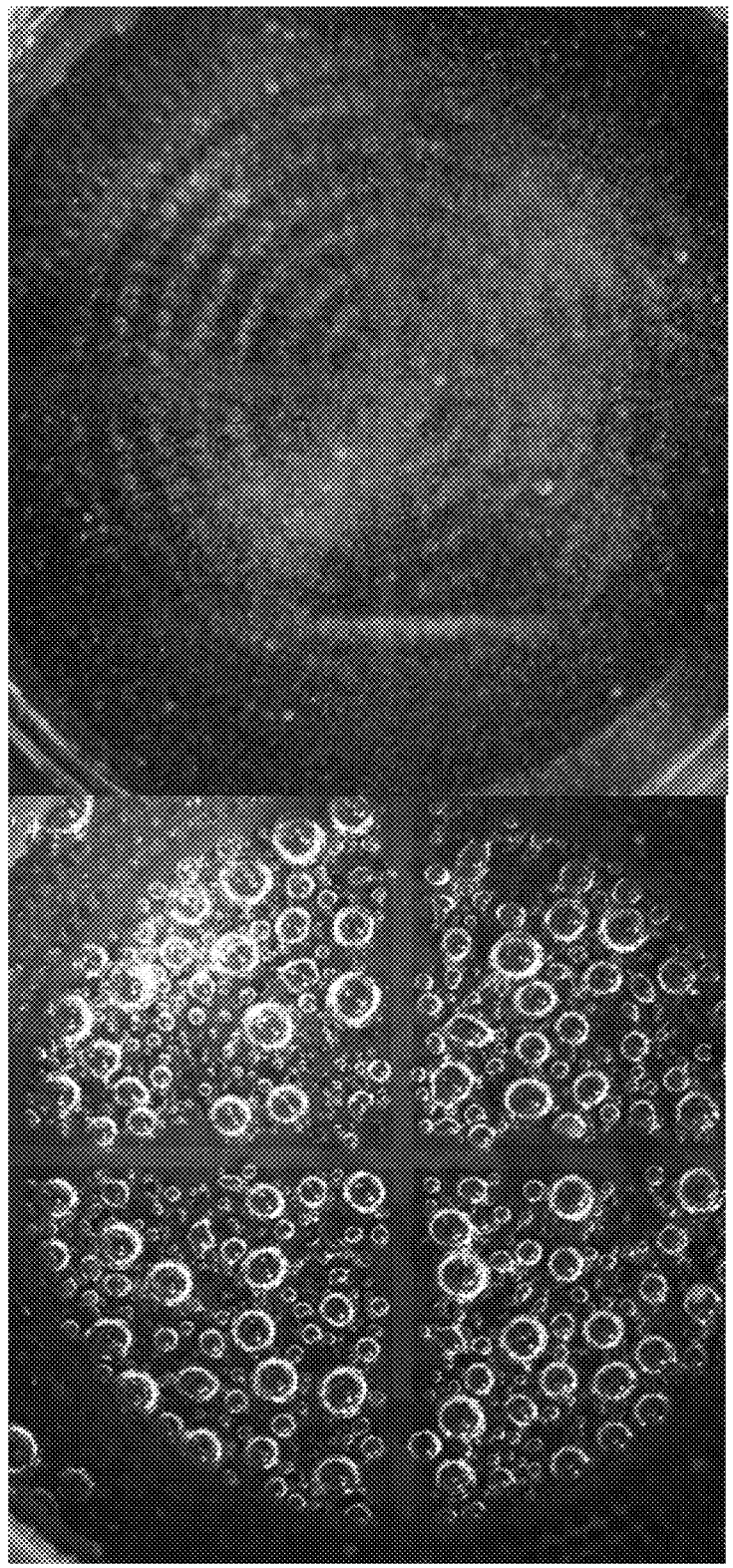

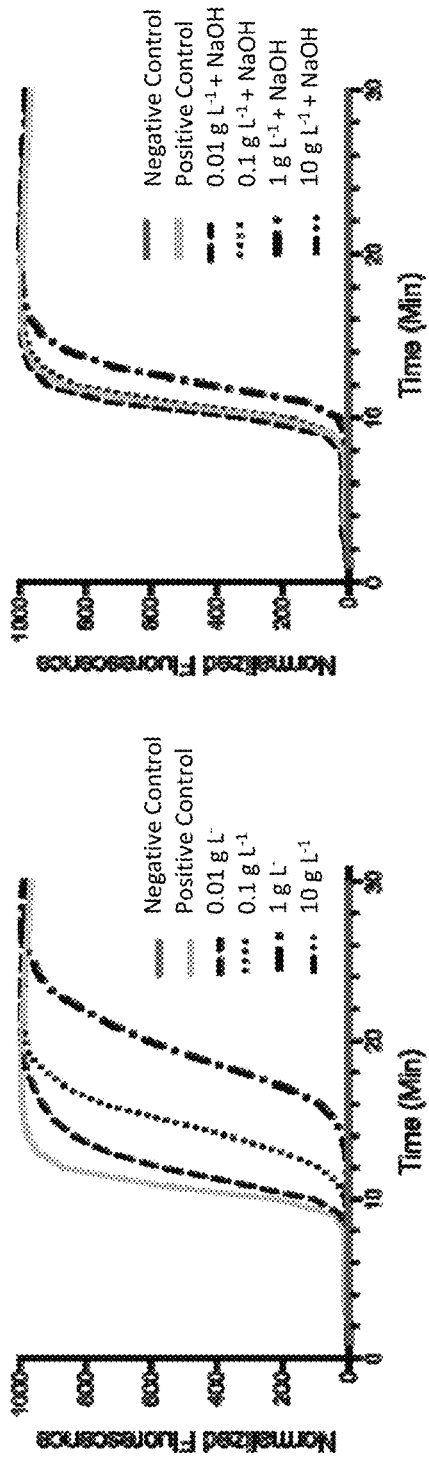
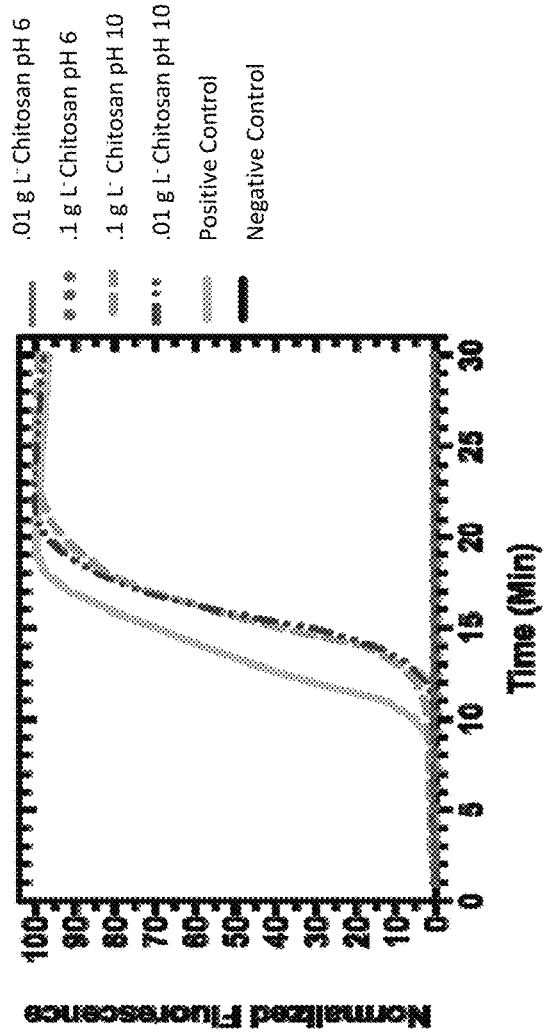
FIG. 31A
FIG. 31B
FIG. 31C

SEQUENCE LISTING

```
<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: chemically synthesized

<400> SEQUENCE: 1
ggtagatcga acggtcatcg                                                   20

<210> SEQ ID NO 2
<211> LENGTH: 18
<212> TYPE: DNA
<213> ORGANISM: Artificial Sequence
<220> FEATURE:
<223> OTHER INFORMATION: chemically synthesized

<400> SEQUENCE: 2
ggccagcaac ggattacg                                                     18

<210> SEQ ID NO 3
<211> LENGTH: 40
<212> TYPE: DNA
<213> ORGANISM: Artificial Sequence
<220> FEATURE:
<223> OTHER INFORMATION: chemically synthesized

<400> SEQUENCE: 3
cgcagacttc aagcgtcacg atcgaaggaa cggtggatgc                             40

<210> SEQ ID NO 4
<211> LENGTH: 38
<212> TYPE: DNA
<213> ORGANISM: Artificial Sequence
<220> FEATURE:
<223> OTHER INFORMATION: chemically synthesized
```

-continued

```
<400> SEQUENCE: 4
ccttaccggc gacgggaaaa cttttcaggc gcgaccag                               38

<210> SEQ ID NO 5
<211> LENGTH: 20
<212> TYPE: DNA
<213> ORGANISM: Artificial Sequence
<220> FEATURE:
<223> OTHER INFORMATION: chemically synthesized

<400> SEQUENCE: 5
tgagatggcg gcagcaagtg                                                   20

<210> SEQ ID NO 6
<211> LENGTH: 19
<212> TYPE: DNA
<213> ORGANISM: Artificial Sequence
<220> FEATURE:
<223> OTHER INFORMATION: chemically synthesized

<400> SEQUENCE: 6
ggcgaatgcc gttatccag                                                    19

<210> SEQ ID NO 7
<211> LENGTH: 19
<212> TYPE: DNA
<213> ORGANISM: Artificial Sequence
<220> FEATURE:
<223> OTHER INFORMATION: chemically synthesized

<400> SEQUENCE: 7
cgtgacgctt gaagtctgc                                                    19

<210> SEQ ID NO 8
<211> LENGTH: 21
<212> TYPE: DNA
<213> ORGANISM: Artificial Sequence
<220> FEATURE:
<223> OTHER INFORMATION: chemically synthesized

<400> SEQUENCE: 8
cgcgcctgaa aagcgtaatc c                                                 21

<210> SEQ ID NO 9
<211> LENGTH: 20
<212> TYPE: DNA
<213> ORGANISM: Artificial Sequence
<220> FEATURE:
<223> OTHER INFORMATION: chemically synthesized

<400> SEQUENCE: 9
cgcatgacga atcagctctc                                                   20

<210> SEQ ID NO 10
<211> LENGTH: 21
<212> TYPE: DNA
<213> ORGANISM: Artificial Sequence
<220> FEATURE:
<223> OTHER INFORMATION: chemically synthesized

<400> SEQUENCE: 10
caatcaccgc cgttttcccg t                                                 21

<210> SEQ ID NO 11
<211> LENGTH: 20
```

```
<212> TYPE: DNA
<213> ORGANISM: Artificial Sequence
<220> FEATURE:
<223> OTHER INFORMATION: chemically synthesized

<400> SEQUENCE: 11
cgatgggcga aacagtgaat                                              20

<210> SEQ ID NO 12
<211> LENGTH: 19
<212> TYPE: DNA
<213> ORGANISM: Artificial Sequence
<220> FEATURE:
<223> OTHER INFORMATION: chemically synthesized

<400> SEQUENCE: 12
tgctggcgtc aagttttgg                                               19

<210> SEQ ID NO 13
<211> LENGTH: 20
<212> TYPE: DNA
<213> ORGANISM: Artificial Sequence
<220> FEATURE:
<223> OTHER INFORMATION: chemically synthesized

<400> SEQUENCE: 13
cgccggtaag gccataaaaa                                              20
```

POINT-OF-CARE ELECTROFLOTATION OF DISPERSED, LOW TOLERANCE PATHOGENS

CROSS-REFERENCE TO RELATED APPLICATIONS

This application is a U.S. national phase application filed under 35 U.S.C. § 371 claiming benefit to International Patent Application No. PCT/US19/41833, filed Jul. 15, 2019, which is entitled to priority under 35 U.S.C. § 119 (e) to U.S. Provisional Application No. 62/697,574, filed Jul. 13, 2018, each of which applications is hereby incorporated herein by reference in its entirety.

STATEMENT REGARDING FEDERALLY SPONSORED RESEARCH OR DEVELOPMENT

This invention was made with government support under Grant No. 2014-67005-21702 and Grant No. HAW05027-H awarded by the National Institute of Food and Agriculture. The government has certain rights in the invention.

BACKGROUND OF THE INVENTION

Food borne diseases result in hundreds of thousands of cases of illness, thousands of hospitalizations, and hundreds of deaths in the United States annually (Scahrff R L. et al., 2012, J. Food Prot. 75:123-131). The most common food pathogens include *Clostridium perfringens*, *Salmonella enteritidas*, *Camplyobacter* spp., *Staphylococcus aureus*, and *Escherichia coli* 0157. Federal regulations, like the FDA Food Safety Modernization Act of 2011 (111th Congress, 2011, Pharm. Law Desk Ref.: 111-353) identify the current state of public health attributed to food safety as a serious burden, but believe outbreaks of contaminations can be prevented by implementing preventative controls and standards across the food supply chain. One key recommendation is that good sanitation practices be conducted with routine testing for pathogens on-site by rapid detection methods to provide real-time results in order to mitigate outbreaks from food borne illness. In the last two decades rapid diagnostics based on immunological interactions (Chandler, D. P. et al., 2001, Int. J. Food Microbiol. 70:143-154), nucleic acid-based assays (Martzy R. et al., 2017, Water Res. 122:62-69) and other biosensors (i.e. Lab-on-chip technology) (You D. J. et al., 2011, Biosens. Bioelectron. 28:399-406) have been integrated into miniaturized portable hand-held technology enabling detection in 1 hour or less. While rapid detection technologies seem ideal for on-site testing, they lack sufficient sensitivity for direct point-of-care (POC) testing (Mandal P. K. et al., 2011, Am. J. Food Technol. 6:87-102). As a result, trace contaminations of pathogens on food and in the environment, remain notoriously difficult to detect in a timely fashion.

The limit of detection by rapid methods is generally above $10^3$ CFU/g or $10^3$ CFU/ml of food or liquid samples (Abdel-Hamid, I. et al., 1999, Anal. Chim. Acta 399:99-108; Taylor, P. et al., 2009, Environmental technology 30 (4): 337-344). For example, gene-based assays typically test sample volumes of 1-5 µL, so that a single replicate of even a robust assay is statistically unlikely to detect pathogens at levels below $10^3$ CFU/mL. This limit exceeds regulatory levels for many high-consequence pathogens.

Sample preparation methods like enrichment and concentration of bacteria can provide sufficient target for amplification in gene-based assays, however severely delay the sample-to result time and require a lab facility (Stevens, K. A. et al., 2004, Microbiol. 30:7-24). While methods like centrifugation (Maron P. et al., 2006, Eur. J. Soil. Bio., 42:65-73), filtration (Karim M. N. et al., 2008, Biochem. Eng. J. 40:512-519), and immunomagnetic separation (Fu Z. et al., 2005, Int. J. Food Microbiol. 99:47-57) have the ability to rapidly concentrate bacteria from samples, these approaches are challenging to implement in field and even rudimentary labs.

In summary, practical application of point-of-care (POC) diagnostics in agriculture, environmental, and food industries is beset with fundamental challenges including: 1) complex environmental sample matrices with many compounds potentially inhibitory of molecular assay reactions (Stevens, K. A. et al., 2004, Microbiol. 30:7-24) 2), physical limitations on direct detection limits, necessitating extensive sampling and/or time-consuming enrichment for meaningful results, (Mandal P. K. et al., 2011, Am. J. Food Technol. 6:87-102), and; 3) logistical requirements for successfully detecting organisms dispersed on an ecological scale—for example, how to process large (liters or hundreds of mL) samples into small (µL) assay formats without losing meaningful information (Thatcher S. A., 2015, Clin. Chem. 61:89-99).

The development of portable technologies capable of producing high quality sample preparation is a crucial, but under-researched step to realizing truly real-time detection with portable biotechnology for POC-testing in food safety, water quality or agricultural applications (Stevens, K. A. et al., 2004, Microbiol. 30:7-24). While portable molecular diagnostics have reached commercial maturity, technologies to facilitate sample acquisition and processing for use with downstream molecular testing platforms remain underdeveloped. The present invention meets this need.

SUMMARY OF THE INVENTION

In one aspect, the present invention provides an electroflotation device comprising: a cylindrical body having a hollow interior, an upper end, and a lower end; a base sealed to the lower end of the body, wherein the base comprises an electrode array exposed to the hollow interior of the body, the electrode array having a concentric outer array and inner array; a removable lid connected to the upper end of the body, wherein a hollow core having an open lower end and upper end extends from the lid into the hollow interior of the cylindrical body, such that the hollow core defines an inner space within the core and an outer space between the hollow core and the cylindrical body; wherein the inner space is in vertical alignment with the inner array and the outer space is in vertical alignment with the outer array; and a microcontroller.

In one embodiment, the core extends past a lower rim of the lid for a distance between about 10% and 50% of a height of the body. In one embodiment, the open upper end of the core is connected to the lid at a headspace, with a taper terminating in an aperture. In one embodiment, the aperture comprises a port adaptable with a connector selected from the group consisting of: threaded connectors, luer locks, and stepped connectors. In one embodiment, the aperture can be connected to an attachment through the port selected from the group consisting of: a dispenser, a filter, a valve, a DNA purification chip, a microfluidic chip, and a spigot. In one embodiment, the lid comprises an airtight and watertight fitting provided by an O-ring, a rubber flange, or a gasket. In one embodiment, the outer and inner arrays each comprise at least one anode and at least one cathode. In one embodiment, the electrodes are arranged in horizontal pattern of concentric rings alternating between anode and cathode. In one embodiment, the electrodes are insert molded and permanently fixed into a thermoplastic elastomer base cradle. In one embodiment, the electrodes are made of a material selected from the group consisting of: platinum, silver, nickel, palladium, gold, silver, copper, iridium, rhodium, and mercury. In one embodiment, the electrodes are printed circuit boards and comprise a protective surface finish selected from the group consisting of: silver filled conductive epoxy, carbon conductive paste, conductive silicone and platinum coated titanium electrodes. In one embodiment, the device comprises at least one sensor selected from the group consisting of: flow sensors, pressure sensors, liquid level sensors, temperature sensors, pH sensors, volume sensors, level sensors, current sensors, turbidity sensors, conductivity sensors, and voltage sensors.

In one aspect, the present invention provides a method of detecting and identifying pathogens, wherein the method comprises the steps of: providing the electroflotation device according to the present invention; supplying a sample into the electroflotation device; energizing the inner array to form upward flowing microbubbles that direct and concentrate sample particulates into the inner space; energizing both inner and outer arrays so that gas accumulates in the inner and outer spaces and pushes/impels sample particulates in the inner space through the hollow core and out of the lid; collecting defined volume fractions of the sample particulates through the lid; performing DNA extraction using an extraction method to release nucleic acids in the volume fraction of the sample particulates; amplifying the released nucleic acid by a nucleic acid amplification assay; and identifying pathogens using specific primers.

In one embodiment, the nucleic acid amplification assay is selected from the group consisting of: polymerase chain reaction (PCR); strand displacement amplification (SDA); roiling circle amplification (RCA); nucleic acid sequence-based amplification (NASBA), Q-β replicase amplification; helicase-dependent amplification (HAD); loop-mediated isothermal amplification (LAMP); nicking enzyme amplification reaction (NEAR), and recombinase polymerase amplification (RPA). In one embodiment, the method further comprises a step of pathogen identification using an immunoassay, flow cytometry, or cell senescence assay. In one embodiment, the sample is selected from the group consisting of: bodily fluids, environmental samples, plant materials, biological warfare agent samples, research samples, irrigation water, agricultural product rinsates, drinking water, waste water, agricultural runoff, food homogenates, aquaponics reflow water, flood water, ocean water, and fresh water. In one embodiment, the method comprises a further step of contacting the sample with an additive formulation selected from the group consisting of: a flocculant, a surfactant, a pH modifier, and combinations thereof. In one embodiment, the flocculant is chitosan. In one embodiment, the surfactant is Pluronic F-68. In one embodiment, the pH is adjusted to above 9.5.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 2A is a top view of a platinum coated titanium electrode array assembly. FIG. 2B depicts an electrode array schematic. An inner array is shown in yellow, and an outer array is shown in red. The grey area corresponds to the TPE housing.

FIG. 3A through FIG. 3C depict a sequence of electroflotation for concentrating and recovering suspended particles (red dots). A sample volume is loaded into a device (FIG. 3A), inner electrode arrays are energized to concentrate particles in collection chamber (FIG. 3B), and inner and outer electrodes arrays are energized to displace concentrated sample (FIG. 3C).

FIG. 4A depicts another exemplary electroflotation device. FIG. 4B depicts a magnified view of an insert-molded electrode array, illustrating concentric inner and outer arrays.

FIG. 6A depicts a PCB electrode array without corrosion coating. FIG. 6B depicts an EAGLE CAD schematic of electrical routes of inner anode (red cross-hatch), inner cathode (blue cross hatch) outer anode (solid red), outer cathode (solid blue).

FIG. 14A and FIG. 14B depict experimental outlines of *E. coli* electroflotation. FIG. 14A depicts a control outline. FIG. 14B depicts an experimental outline.

FIG. 15A depicts SEM images of untreated silver epoxy before oxidation. FIG. 15B depicts SEM images of silver epoxy after oxidation.

FIG. 16A depicts EDS distribution of Ag (red), K (green) and Cl (blue) overlaid onto the SEM image depicted in FIG. 16B.

FIG. 17A depicts distribution of Ag (red), K (green) and Cl (blue) overlaid onto the SEM image depicted in FIG. 17B.

FIG. 19A depicts corrosion (seen in blue) of the PCB electrode array with applied CCP layer after 120 minutes of EF at 4.21 V in 0.1 M potassium phosphate buffer. FIG. 19B depicts current (mA) of inner and outer electrode arrays during 120 min. of EF treatment.

FIG. 20A and FIG. 20B depict PDMS coated electrodes undergoing electrolysis with and without surface modification. FIG. 20A depicts the PDMS surface before surface modification. FIG. 20B depicts the PDMS surface after Oxygen Plasma Treatment and PEG grafting.

FIG. 21A depicts current (mA) (red line) over time at varying voltage (V) (black line) of PDMS coated PCB electrodes before $O_2$ plasma surface modification and PEG grafting. FIG. 21B depicts current (mA) (red line) over time at varying voltage (V) (black line) of PDMS coated PCB electrodes after $O_2$ plasma surface modification and PEG grafting.

FIG. 23A depicts recorded current (mA) for high turbulence for 20 minute EF treatments using TiPt electrodes. FIG. 23B depicts recorded current (mA) for low turbulence for 20 minute EF treatments using TiPt electrodes.

FIG. 31A through FIG. 31C depicts the results of increasing sample pH to prevent LAMP inhibition by chitosan. FIG. 31A depicts representative LAMP amplification curves for samples (pH 5.8 and pH 11) containing 0.0, 0.01, 0.1 and 1 g L$^{-1}$ chitosan. Samples (pH 5.8) containing 10 g L$^{-1}$ chitosan completely inhibited LAMP (data not shown). Samples containing 1 g L$^{-1}$ chitosan significantly inhibited LAMP amplification while samples containing 0.01 and 0.1 g L$^{-1}$ only slightly inhibited LAMP when compared to the positive control not containing any chitosan. FIG. 31B depicts the addition of NaOH to samples removed most of the inhibition on LAMP. FIG. 31C depicts representative LAMP amplification curves for samples (pH 6 and pH 10) containing 0.01 and 0.1 g L$^{-1}$ chitosan. Samples (pH 6) containing 0.01 and 0.1 g L$^{-1}$ chitosan completely inhibited LAMP. Whereas samples adjusted with NaOH to achieve pH 10 also containing 0.01 and 0.1 g L$^{-1}$ chitosan did not inhibit LAMP. All reactions contained 0.2 ng *E. coli* 25922 DNA except the negative control. 3 replicate assays were performed for each condition.

DETAILED DESCRIPTION

Figure 1:
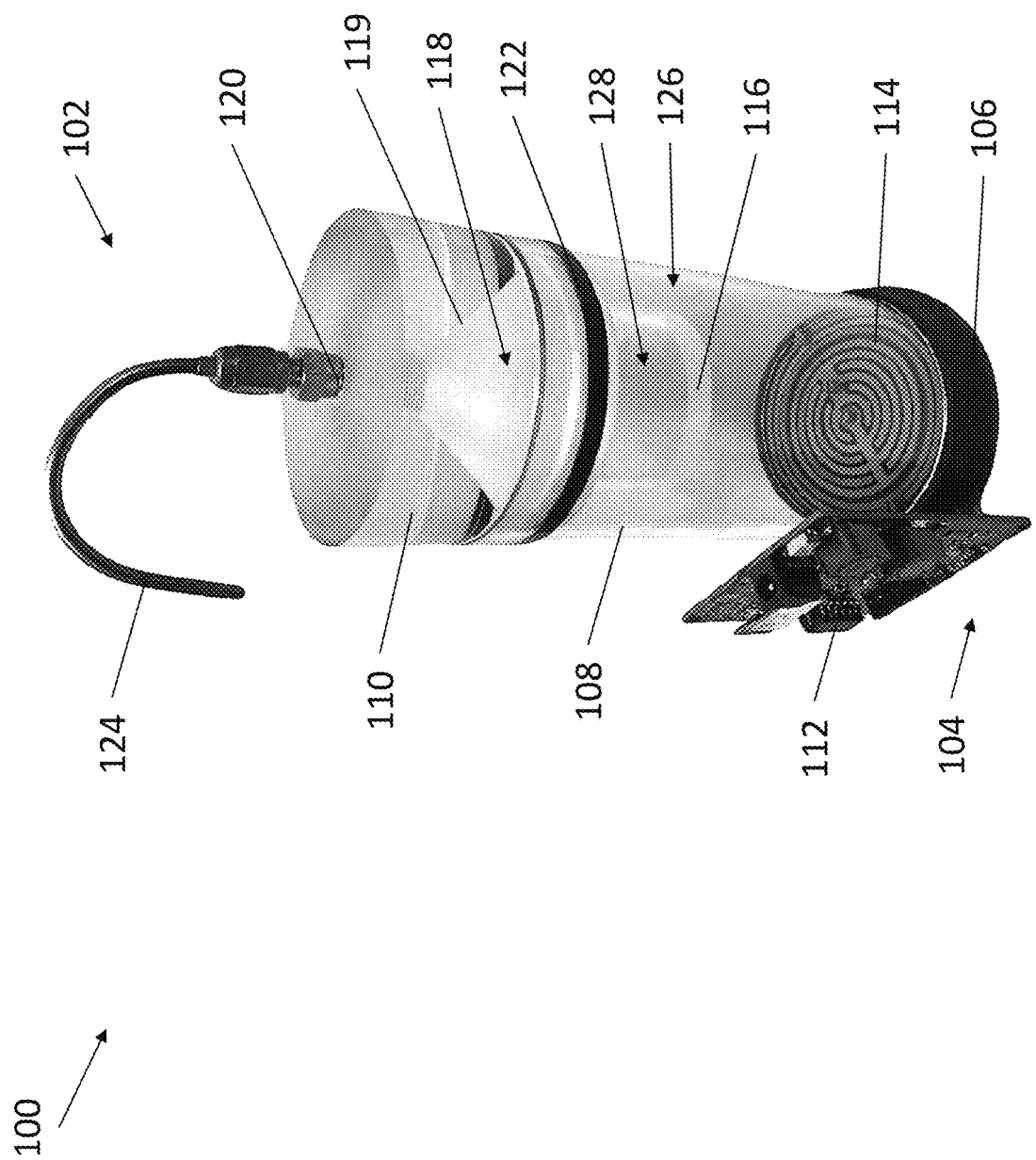
FIG. 1 depicts an exemplary electroflotation device.

It is to be understood that the figures and descriptions of the present invention have been simplified to illustrate elements that are relevant for a clear understanding of the present invention, while eliminating, for the purpose of clarity, many other elements found in the field of point-of-care devices, including those indicated for the purpose of diagnostics by improving the capacity to detect trace contaminations. Those of ordinary skill in the art may recognize that other elements and/or steps are desirable and/or required in implementing the present invention. However, because such elements and steps are well known in the field, and because they do not facilitate a better understanding of the present invention, a discussion of such elements and steps is not provided herein. The disclosure herein is directed to all such variations and modifications to such elements and methods known to those skilled in the art.

Definitions

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G or 4G/LTE networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Electroflotation Device

The present invention provides in part electroflotation devices capable of concentrating and extracting a population of targeted and non-targeted particles from a volume of sample fluid. The devices comprise electrodes that, when energized, produce columns of microbubbles. The microbubbles carry (impel) target particles to the surface of the sample fluid to concentrate the target particles. The microbubbles collect in a gas trap to displace the sample fluid to deliver the concentrated target particles out of the device for extraction.

Referring now to FIG. 1, an exemplary electroflotation device 100 is depicted. Device 100 has an upper end 102, a lower end 104, and comprises a base 106, a body 108, a lid 110, and a microcontroller 112. Body 108 comprises a hollow, substantially cylindrical shape and is sealed at a lower end by base 106. Base 106 comprises electrode array 114 exposed to the hollow interior of body 108. Body 108 is scalable at an upper end by a removable lid 110. Lid 110 can fit onto body 108 in any suitable manner, such as by a friction fit, a threaded fitting, a twist lock fitting, and the like. In some embodiments, lid 110 comprises an airtight and watertight fitting provided by O-ring 122, a rubber flange, a gasket, and the like. Lid 110 comprises a hollow core 116 having an open lower end and upper end. Core 116 extends past a lower rim of lid 110 for a distance between about 10% and 50% of a height of body 108. When lid 110 is secured to body 108, the extension of core 116 positions the open lower end of core 116 within the hollow interior of body 108 to partition an upper portion of the hollow interior of body 108 into two concentric regions: an outer space 126 (corresponding to a space between body 108 and core 116) and an inner space 128 (corresponding to the hollow interior of core 116). The open upper end of core 116 is connected to lid 110 at a headspace 118, which is substantially funnel shaped with a taper 119 terminating in an aperture 120. Aperture 120 is fluidly connected to an exterior of device 100 and comprises a port adaptable with any commonly used connector, including but not limited to threaded connectors, luer locks, stepped connectors, and the like. Accordingly, aperture 120 is compatible with any number of suitable attachments, including but not limited to a dispenser 124, a filter, a valve, a spigot, a microfluidic chip, a DNA purification chip, and the like.

Referring now to FIG. 2, electrode array 114 is described in detail. Electrode array 114 comprises an outer array 132 and an inner array 134. Outer array 132 and inner array 134 are concentric electrode arrays that are positioned to mirror outer space 126 and inner space 128 formed by core 116 and body 108, as described above. Outer array 132 comprises at least one anode 136 and at least one cathode 138, and inner space 128 comprises at least one anode 140 and at least one cathode 142. Each anode can be separated by each cathode by any suitable spacing, such as a distance between about 500 μm to 1500 μm. Each electrode is secured to electrode array 114 by at least one screw 144. Printed circuit board (PCB) connector 130 is provided to interface with microcontroller 112.

Referring now to FIG. 3A through FIG. 3C, the operation of device 100 is now described. Beginning with FIG. 3A, a sample volume containing an amount of particles is loaded into the hollow interior of body 108. The sample volume rises above the open lower end of core 116 and occupies outer space 126 and inner space 128. In FIG. 3B, inner array 134 is energized to generate a flow of collimated microbubbles in a region directly beneath inner space 128, whereupon target particles are directed upwards towards inner space 128 and concentrated within inner space 128. The microbubbles are vented out of inner space 128 through aperture 120 and any attached component, such as a dispenser 124. In FIG. 3C, outer array 132 is energized to generate a flow of collimated microbubbles in a region directly beneath outer space 126. Outer space 126 does not vent gas, permitting microbubbles to accumulate in outer space 126 and to displace the sample volume. The displacement of sample volume out of outer space 126 directs sample volume and concentrated target particles through inner space 128 and out of dispenser 124 into a vessel 146. Vessel 146 can be any suitable vessel for collecting a sample, including but not limited to PCR tubes, vials, cuvettes, centrifuge tubes, petri dishes, microfluidic chips, and the like.

Referring now to FIG. 4A and FIG. 4B, an exemplary electroflotation device 200 is depicted. Device 200 has an upper end 202, a lower end 204, and comprises a base 206, a body 208, a lid 210. In some embodiments, base 206 further houses one or more microcontrollers and power sources. In some embodiments, base 206 comprises spring-loaded contacts for interfacing with an external microcontroller and power source, such as a cradle. Body 208 comprises a hollow, substantially cylindrical shape and is scaled at a lower end by base 206. Base 206 comprises electrode array 214 exposed to the hollow interior of body 208. Body 208 is scalable at an upper end by a removable lid 210. Lid 210 can fit onto base 206 in any suitable manner, such as by a friction fit, a threaded fitting, a twist lock fitting, and the like. In some embodiments, lid 210 comprises an airtight and watertight fitting provided by O-ring 222, a rubber flange, a gasket, and the like. Lip 216 extends past a lower rim of lid 210 for a distance between about 10% and 50% of a height of body 208. When lid 210 is secured to base 206, the extension of lip 216 positions the open lower end of lip 216 within the hollow interior of body 208 to partition an upper portion of the hollow interior of body 208 into two concentric regions: an outer space 226 (corresponding to a space between body 208 and lip 216) and an inner space 228 (corresponding to the hollow interior of lip 216). Funnel 218 is connected to lip 216 at a wide end and has a taper 219 terminating in an aperture 220 at a narrow end. Aperture 220 is fluidly connected to an exterior of device 200 and comprises a port adaptable with any commonly used connector, including but not limited to threaded connectors, luer locks, stepped connectors, and the like. Accordingly, aperture 220 is compatible with any number of suitable attachments, including but not limited to a dispenser 224, a filter 225, a valve, a spigot, a microfluidic chip, a DNA purification chip, and the like.

Similar to device 100 described elsewhere herein, electrode array 214 comprises an outer array 232 and an inner array 234. Outer array 232 and inner array 234 are concentric electrode arrays that are positioned to mirror outer space 226 and inner space 228 formed by lip 216 and body 208, as described above. Outer array 232 comprises at least one anode 236 and at least one cathode 238, and inner space 228 comprises at least one anode 240 and at least one cathode 242. Each anode can be separated by each cathode by any suitable spacing, such as a distance between about 500 μm to 1500 μm. Each electrode can be secured to electrode array 214 by at least one screw. In some embodiments, electrodes can be permanently fixed by insert molding or by being over molded into the base and would then not require any screws.

Device 200 operates in a similar manner as device 100. A sample volume containing an amount of particles is loaded into the hollow interior of body 208. The sample volume rises above lip 216 and occupies outer space 226 and inner space 228. Inner array 234 is energized to generate a flow of collimated microbubbles in a region directly beneath inner space 228, whereupon target particles are directed upwards towards inner space 228 and concentrated within inner space 228. The microbubbles are vented out of inner space 228 through aperture 220 and any attached component, such as a dispenser 224. Outer array 232 is then energized to generate a flow of collimated microbubbles in a region directly beneath outer space 226. Outer space 226 does not vent gas, permitting microbubbles to accumulate in outer space 226 and to displace the sample volume. The displacement of sample volume out of outer space 226 directs sample volume and concentrated target particles through inner space 228 and out of dispenser 224 into a vessel. The vessel can be any suitable vessel for collecting a sample, including but not limited to PCR tubes, vials, cuvettes, centrifuge tubes, petri dishes, microfluidic chips, and the like.

In various embodiments, the devices of the present invention can be controlled by a microcontroller. The microcontroller can comprise any computing device, for example an integrated microcontroller or processor, and can also comprise a quantity of volatile and/or non-volatile memory on which instructions may be stored to perform steps of a method of the present invention. The microcontroller can be electronically connected to a voltage regulator to modulate output in the electrode arrays. The device can be powered by a power source, for example a battery, and can further include power management hardware and one or more communication devices, for example wired or wireless communication devices for transmitting or receiving data, configuration information, or operating instructions to and from a remote computing device. In some embodiments, the device includes a Bluetooth transceiver that may be paired with a remote computing device to send and receive data.

The components of the devices of the present invention can have any suitable construction. In some embodiments, the devices can be described as having a volume rating. A volume rating describes the recommended maximum capacity of sample that a device can hold within a hollow interior. Exemplary volumes include but are not limited to 100 mL, 250 mL, 500 mL, 750 mL, 1 L, 1.5 L, 2 L, 2.5 L, 5 L, and the like. The devices can have any suitable dimensions to contain a desired volume. For example, the devices can have a diameter between about 5 cm to about 50 cm and a height between about 5 cm to about 100 cm. In various embodiments, the devices of the present invention can include one or more sensors. Contemplated sensors include but are not limited to flow sensors, pressure sensors, liquid level sensors, temperature sensors, pH sensors, volume sensors, level sensors, current sensors, voltage sensors, turbidity sensors, conductivity sensors, and the like. The various sensors can be used separately or in combination to monitor the contents of a loaded sample volume, to monitor the rate of gas accumulation and sample volume displacement, to monitor the output of the electrode arrays, and to ensure that the devices are placed on a level surface. In some embodiments, a liquid level sensor, such as a capacitive sensor, is provided adjacent to an aperture of a lid of the devices. The liquid level sensor can detect when a sample volume approaches the aperture and can notify a user or automatically deactivate electrode arrays.

The components of the systems of the present invention can be constructed from any suitable material, including but not limited to metals and polymers, such as stainless steel, titanium, aluminum, acrylic, polyether ether ketone (PEEK), polyethylenes, polyvinyls, polyurethanes, polyamides, polycarbonates, and the like. In some embodiments, certain components or portions of certain components can be constructed from a transparent or translucent material. The components and systems can be made using any suitable method known in the art. The method of making may vary depending on the materials used. For example, devices substantially comprising a metal may be milled from a larger block of metal or may be cast from molten metal. Likewise, components substantially comprising a plastic or polymer may be milled from a larger block, cast, or injection molded. In some embodiments, the devices may be made using 3D printing or other additive manufacturing techniques commonly used in the art. The electrodes described herein can be constructed from any suitable conductive material, including but not limited to platinum, silver, nickel, palladium, gold, silver, copper, iridium, rhodium, mercury, and the like. The materials can be applied using any technique, including but not limited to electrodeposition, electroplating, and lithography. In various embodiments, the electrodes can comprise a protective surface finish, including but not limited to silver filled conductive epoxy, carbon conductive paste, conductive silicone, platinum coated titanium electrodes, and the like.

Method of Use

The present invention also relates to a method for rapid, on-site detection of pathogens using electroflotation devices described elsewhere herein. In some embodiments, this invention relates to using an electroflotation device to separate, extract, and concentrate small quantities of bacteria dispersed in ecological-scale samples.

Figure 5:
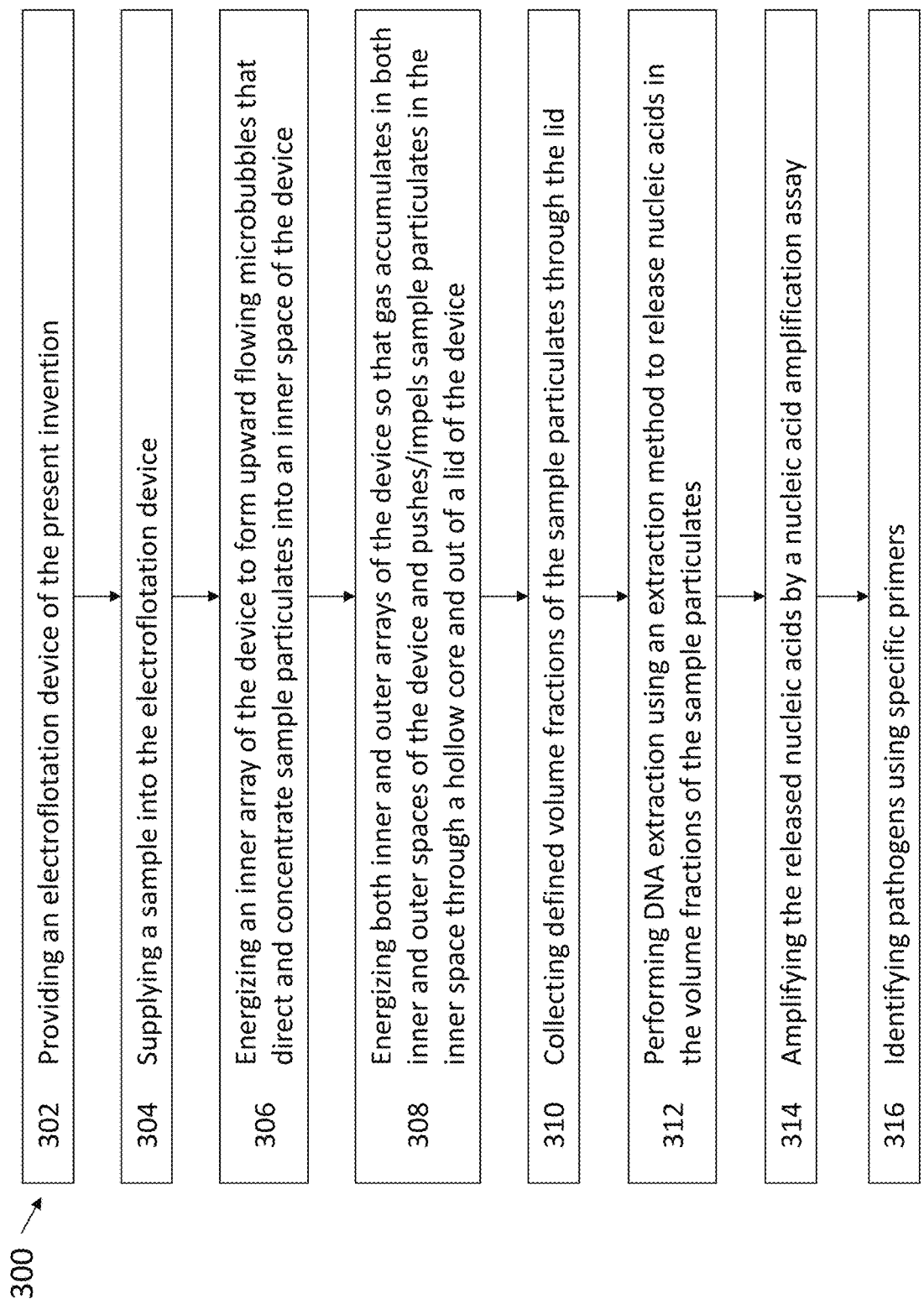
FIG. 5 is a flowchart depicting an exemplary method of rapid, on-site detection of pathogens using an electroflotation device of the present invention.
Figure 6B:
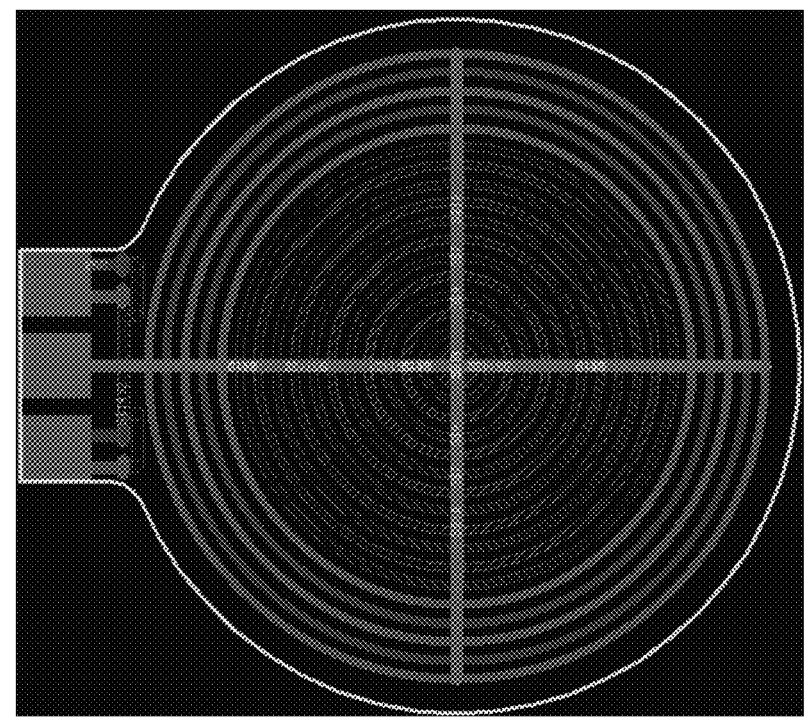
FIG. 6A and FIG. 6B depict an image and electrical schematic of a PCB electrode array.
Figure 6A:
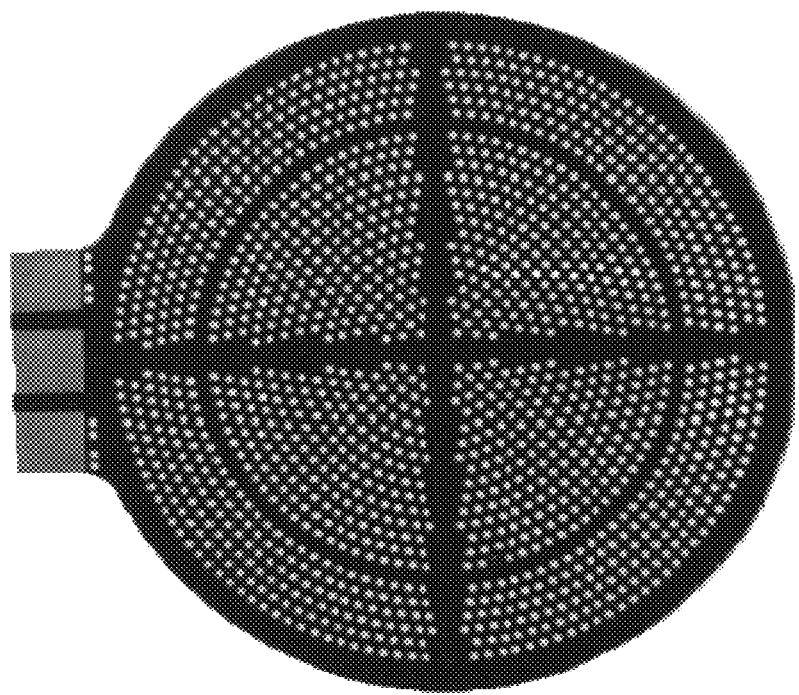

Referring now to FIG. 5, an exemplary method 300 is depicted. Method 300 begins with step 302, wherein an electroflotation device as described herein is provided. In step 304, a sample is supplied into the electroflotation device. In step 306, an inner array of the device is energized to form upward flowing microbubbles that direct and concentrate sample particulates into an inner space of the device. In step 308, both inner and outer arrays of the device are energized so that gas accumulates in both inner and outer spaces of the device and pushes/impels sample particulates in the inner space through a hollow core and out of a lid of the device. In step 310, defined volume fractions of the sample particulates are collected through the lid. In step 312, DNA extraction is performed using an extraction method to release nucleic acids in the volume fractions of the sample particulates. In step 314, the released nucleic acid is amplified by a nucleic acid amplification assay. In step 316, pathogens are identified using specific primers.

A variety of nucleic acid extraction solutions have been developed over the years for extracting nucleic acid sequences from a sample of interest. See, for example, Green, Michael R., and Joseph Sambrook. Molecular cloning: a laboratory manual. New York: Cold Spring Harbor Laboratory Press, 2012. Many such methods typically require one or more steps of, for example, a detergent-mediated step, a proteinase treatment step, a phenol and/or chloroform extraction step, and/or an alcohol precipitation step. In some embodiments, some nucleic acid extraction solutions may comprise an ethylene glycol-type reagent or an ethylene glycol derivative to increase the efficiency of nucleic acid extraction. In some embodiments, some nucleic acid extraction methods only use grinding and/or boiling the sample in water. In some embodiments, methods including solvent-based systems and sonication, could also be utilized in conjunction with other extraction methods.

In some embodiments, a DNA purification chip can be used to perform DNA extraction in real time. In some embodiments, the DNA purification chip of the invention employs an enzymatic process to degrade biological molecules such as proteins and lipids in the sample, and to release the DNA content for downstream analysis and detection. The released DNA then flows in the microfluidic channels to a PCR thermocycler module for amplification and detection by another module.

In some embodiments, this method can be used on bodily fluids (including, but not limited to, blood, urine, serum, lymph, saliva, anal and vaginal secretions, perspiration and semen, of virtually any organism, with mammalian samples being preferred and human samples being particularly preferred), environmental samples (including, but not limited to, air, agricultural, water and soil samples), plant materials, biological warfare agent samples and etc.

In some embodiments, sample acquisition includes irrigation water, agricultural product rinsates, drinking water, and waste water, agricultural runoff, food homogenates, aquaponics reflow water, flood water, ocean and fresh water.

The methods can also support detection methods beyond DNA-based technologies, including but not limited to immunoassays, flow cytometry, In some embodiments, the present invention may be used for diagnostics to determine the presence or absence of a pathogen. In some embodiments, without limitation thereto, pathogens may include viruses inclusive of RNA and DNA viruses, protozoa, worms inclusive of helminths, roundworms and annelids, fungi, Protista, Archaea and bacteria. Detection of—fungal, viral and/or bacterial plant pathogens is also contemplated according to the invention. Plants may include monoeotyledonous and dicotyledonous plants, crops, cereals, fruits, grasses, trees & vines, although without limitation thereto. Non-limiting examples of plant pathogens include DNA and RNA viruses such the RNA vims cucumber mosaic virus, bacteria such as *Pseudomonas syringae* and fungi such as *F. oxysporum* f.sp, *conglutinans* and Batrytis cinema.

However, it will be appreciated that the invention may be broadly practiced using nucleic acid samples obtainable from any organism, whether a non-pathogenic organism or a pathogen of human and non-human animals or plants.

Electroflotation Assisted Recovery by Chemical Additives

In some embodiments, the methods of the present invention further comprise the use of flocculants for separation of suspended particles and colloidal substances from an aqueous liquid. In some embodiments, methods and formulations for treatment of an aqueous sample involves bringing the sample into contact with an aqueous flocculant formulation including a flocculant, an aqueous surfactant formulation containing a surfactant and aqueous liquid sample; and separating flocculated contaminants from the aqueous liquid sample. In some embodiments, contaminant include, but are not limited to, ions, organics, biochemical reagents, heavy metals, heavy metal complexes, inorganic salts, inorganic reagents, dissolved and colloidal natural organic matter, clays, silicas, bacteria, microorganisms and any other chemically or biologically active bodies.

Flocculation is the process whereby particles are formed as a result of destabilization and are induced to come together, make contact and thereby form large and progressively larger agglomerates. In this case, the manifestation of destabilization is realized in practical terms: in effect, flocculation accelerates floc formation, influences the physical characteristics of flocs formed (e.g., their strength, size, and density), and governs the final concentration of destabilized particles.

Flocculants can be classified into overlapping categories such as organic, inorganic, polymeric, anionic, neutral, and cationic. Examples of inorganic flocculants include, but are not limited to, calcium oxide, iron (iii) chloride, iron (ii) sulfate, sodium silicate, polyaluminum chloride, aluminum chlorohydrate, polyaluminum chlorohydrate, aluminum sulfate, sodium aluminate. polyaluminum sulfate, polyaluminum silicate chloride, polyaluminum silicate sulfate.

Organic flocculants are generally polymeric, and depending on the types of functional groups present in the monomeric units, organic flocculants can be further characterized as anionic, neutral or cationic. Examples of organic flocculants include, but are not limited to, polyacrylamide, poly-alkyleneimines (polyethylene imine), polyacrylamide-co-acrylic acid, polysaccharides, such as chitosan, galactomannans, mucilages, alginate, dextran, and glycogen. It should be noted that some of these polymers may be protonated or deprotonated, depending on the pH of the sample.

Flocculant formulations are prepared as aqueous formulations. In some embodiments, the flocculant is a water soluble or water dispersible polymer, wherein the polymer is anionic. In some embodiments, the polymer is cationic.

In some embodiments, multiple flocculants can be used together in the same method, in the same flocculant formulation, and in separated flocculant formulations.

Additional agents can be included in the flocculant formulations to enhance the flocculating properties of the formulations. For example, an additive can serve as a coagulant that facilitates the formation of particulate aggregates. Any of the metal salts described herein can be used additives. Examples of additives include alkali metal salts (such as NaCl, NaOH), alkaline earth metal salts (such as $MgCl_{2.5}CaCl_2$, $CaCO_3)_3$ aluminum sulfate, ferric chloride, polymerized metal salts (such as polyaluminum chloride, polyaluminum silicate sulfate) and oxidants (such as hydrogen peroxide).

In some embodiments, chitosan can be used as the flocculant. Chitosan is an inexpensive, biodegradable, non-toxic, cationic natural polymer/polysaccharide obtained by partial (~50%) deacetylation of chitin found in the exoskeleton of crustaceans like shrimp (Qin, C. et al., 2006, Carbohydr. Polym. 63:367-374). The cationic nature of chitosan is particularly desirable to flocculate and aggregate negatively charged particles. Bacterial cells contain large quantities of side chain amino acids, methyl groups attached to polysaccharides and long chain carbon groups found in lipids; all contributing to the hydrophobic and predominately negatively charged properties of cell membranes (Mozes, N. et al., 1989, Colloids and Surfaces 42:313-329). In gram negative bacterial cells, the anionic phosphate and carboxyl group residing on lipopolysaccharides (LPS) of the outer membrane (OM) will electrostatically interact with the divalent cationic molecules of chitosan (Kong, M. et al., 2010, Int. J. Food Microbiol. 144:51-63). Chitosan polyelectrolytes rely on electrostatic surface charges to engage in extra cellular polymer/particle interactions and therefore can bind to the negatively charged extracellular structures (Rinaudo, M., 2006, Prog. Polym. Sci. 31:603-632).

Chitosan is soluble in slightly acidic conditions (Sugimoto, M. et al., 1998, Carbohydr. Polym. 36:49-59; Qin, C. et al., 2006, Carbohydr. Polym. 63:367-374) and can be categorized as any linear polysaccharide that has various proportions of (1→4) linked 2-acetamido-2-deoxy-β-D-glucopyranose (GlcNAc) and 2-amino-2-deoxy-β-D-glucopyranose (Strand, S. P. et al., 2001, Biomacromolecules 2:126-133). The solubility of chitosan is complicated, challenging to control and largely effects the efficiency of flocculation and other applications. The solubility of chitosan depends on the pH, degree of acetylation (DA) and molecular weight (MW). As a weak base chitosan is insoluble in pure water but soluble in slightly acidic solutions with pH<6.5. To broaden chitosan's flexibility in application, much effort has been applied to performing chemical procedures like the Maillard reaction (Chung, Y. C. et al., 2011, Molecules 16:8504-8514) to prepare functional, water soluble derivatives which has resulted in commercially available chitosan oligosaccharides of agricultural and pharmaceutical grade.

In some embodiments, the methods of the present invention further comprise the use of surfactants to prevent cell damage during electroflotation. Production of biological products like therapeutic proteins, vaccines, and antibodies are commonly derived from cell products cultivated in industrial-scale bioreactors (Chisti, Y., 2000, Trends Biotechnol. 18:420-432). Cell cultures require sufficient oxygen to remain healthy, so artificial aeration is particularly important for cell suspensions larger than 10,000 L (Ma, N. et al., 2004, Biotechnol. Prog. 20:1183-1191) with high cell densities ($\geq 10^6$ CFU/mL). Gas sparging is a common method delivering oxygen to bioreactors. Although highly effective, this process induces lethal levels of hydrodynamic force to the cell resulting in bubble associated damage leading to cell lysis and death. Two mechanisms of cell damage can occur during sparged aeration. Firstly, hydrodynamic forces (i.e., shear stress) at the gas-liquid interface as a bubble passes by and interacts with a cell, and secondly, cell death as bubbles rupture at the media surface (Walls, P. L. L. et al., 2014, Integr. Comp. Biol. 54:1014-1025). Additional cell damage can occur if the degree of turbulence of circulating media is especially intense resulting in high shear in the liquid phase itself (Chisti, Y., 2000, Trends Biotechnol. 18:420-432; Sowana, D. D. et al., 2001, Chem. Eng. Res. Des. 79:867-875). In the application of food safety and microbiology, it is important to keep cells in their native viable state as only living cells can be infectious.

Surfactants can change interactions between a bubble and surrounding biological material in a fluid by modifying the surface tension forces that typically attract, stress or disperse biomaterial (Ma, N. et al., 2004, Biotechnol. Prog. 20:1183-1191; Tharmalingam, T. et al., 2008, Mol. Biotechnol. 39:167-177; Walls, P. L. L. et al., 2014, Integr. Comp. Biol. 54:1014-1025.

In some embodiments, surfactant formulations are prepared as aqueous formulations. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates. such as sodium bis-(2-ethylthioxylj-sulfosuccinate, and alkyl sulfates such as sodium lauryl ether sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene, and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate. polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Suitable amphoteric surfactants include, but are not limited to, compounds such as sodium N-dodecyl-beta-alanine, sodium N-lauryl-beta-iminodipropionate, myristo-amphoacetate, lauryl betaine, and lauryl sulfobetaine. Nonionic surfactants include, but are not limited to, Pluronic® F-68, secondary alcohol ethoxylates. decyl glucoside, lauryl glucoside, octyl glucoside, fatty alcohol polyglycol ether, alkylphenol polyglycol ether, fatty acid polyglycol ester, polypropylene oxide-polyethylene oxide mixed polymers, N-methyl myristamide.N-sorbityl lauramide, N-methyl myristamide, N-sorbityl myristamide. and alkyl polysaccharides such as octyl, nonyldecyl, undecyldodecyl. tridecyl. tetradecyl. pentadecyl, hexadccyl. heptadecyl, and octa-decyl. di-. tri-. tetra-, penta-. and hexaglucosides, galacto-sides, lactosides, glucoses, fructosides, fructoses and/or galactoses. The surfactant formulations may contain additional components such as alkali metal salts (such as NaCl, NaOH), alkaline earth metal salts (such as $MgCl_2$, $CaCl_2$)), and oxidants (such as hydrogen peroxide). The relative amounts of the additional components which contain the surfactant formulation may vary over a wide range.

In some embodiments, multiple surfactants can be used together in the same method, in the same surfactant formulation, and in separated surfactant formulations.

In some embodiments, the methods described consist of adding, combining, or mixing a flocculant and a surfactant with the aqueous liquid. In some embodiment, the flocculant and the surfactant can be added as separate formulations or separate compositions, or the flocculant and surfactant can be added as a single formulation. In some embodiments of the single formulation comprising the flocculant and surfactant, the flocculant and the surfactant are separate compositions within the single formulation. In some embodiments, the flocculant and surfactants do not form a single additive molecule or polymer which comprises both the flocculant and surfactant. Without wishing to be bound by theory, the addition of a surfactant may aid in dispersing the flocculant in the wastewater. The flocculant is then more readily able to induce flocculation of contaminants present through processes such as electrostatic interaction, charge neutralization, and/or polymer bridging.

The methods described herein can be optimized to remove all or the majority of contaminants present in aqueous liquid. Those skilled in the art will recognize that the source and composition of the sample will affect the treatment conditions required, such as the relative formulation volumes to be applied and the treatment times required in treatment of the sample. It is well known that each type of sample, depending on its origin, will have its own particularities and that within the same class or type of sample significant variations may be encountered.

The pH of the aqueous liquid sample may affect the activity of flocculants and surfactants. In certain embodiments of the method, the pH of the aqueous liquid sample may be adjusted, as appropriate, in order to improve the efficiency of the treatment process. If the aqueous liquid sample to be treated is highly acidic (pH<3) or highly basic (pH>10), the pH of the aqueous liquid sample may be preferably adjusted to a pH in the range of about 4-9 prior to discharge of the treated water. In some embodiments the pH of the aqueous liquid sample is adjusted to a pH of about 5-8, 6-7, or to a pH of about 7 (i.e. neutral pH) prior to discharge.

In certain embodiments, the amount (by weight) of flocculant and/or surfactant formulation, added separately or in combination, to a given type or volume of aqueous liquid sample to be treated is in the range of between about 0.1 mg and 1000 mg per kilogram of aqueous liquid sample. Additionally, the ratio of flocculant to surfactant used in the treatment may be optimized to maximize the efficacy of the treatment and minimize the amount of flocculant used. in some embodiments, the step of bringing a flocculant and a surfactant into contact with aqueous liquid sample includes adding, combining, or mixing the flocculant and surfactant with the wastewater and applying some form of agitation or mixing, which may include, but is not limited to, mechanical stirring or acoustic (i.e. sonication-based) forms of mixing, to ensure sufficient adequate contact of the contaminants present in the aqueous liquid sample with the flocculant and surfactant formulation. In certain embodiments, agitation or mixing is performed for a few seconds up to about 20 minutes. Typically, the treatment is conducted at room temperature.

In certain embodiments, the combination or mixture of flocculant, surfactant, and aqueous liquid sample is allowed to stand for a sufficient amount of time to allow for flocculation and sedimentation of contaminants from the aqueous liquid sample to occur. In certain embodiments, sedimentation time is in the range of about 30 seconds up to about 5 hours, as determined by visual observation of sedimentation followed by UV transmission measurement.

Pathogen Detection Model

The present invention relates to methods and kits for rapid, on-site preparation of DNA and for rapid, on-site detection of DNA. Accordingly, the invention provides method and kits that may be used to prepare and/or detect DNA from any source in a rapid manner with minimal equipment, thereby being ideally suited to point of care (POC) or other on-site applications, including providing a rapid response system for detecting new outbreaks of emerging diseases in human and non-humans, animals and plants.

In an aspect, the invention provides a method of detecting a nucleic acid, said method including the step of combining an isolated nucleic acid and a particle, wherein the isolated nucleic acid and the particle are capable of forming a complex which can be detected by visual inspection. In another aspect, the invention provides a kit for detecting a nucleic acid, said kit comprising a particle which is capable of forming a complex with an isolated nucleic acid, which complex is capable of being detected by visual inspection. The kit may further comprise one or more of; a nucleic acid polymerase for nucleic acid sequence amplification; one or more primers for nucleic acid sequence amplification; a magnet; reagents for nucleic acid extraction; a filter; and/or one of more reaction vessels.

In some embodiments, the kit may be used according to the method hereinbefore described. Accordingly, the kit may provide one or a plurality of polymerases, particles, buffers, vessels and other components that facilitate the preparation and visual detection of nucleic acids as disclosed herein.

Nucleic acid extraction may be by any method known in the art. Typically, nucleic acid extraction may be facilitated by extraction buffer which typically comprises a non-ionic detergent, salt, pH buffer and a chaotropic agent. Non-limiting examples of extraction buffers are provided in more detail hereinafter. Nucleic acids so obtained or extracted are referred to herein as a "nucleic acid sample". Typically, the nucleic acid sample is obtained by extraction from a source such as hereinbefore described, without subjecting the extracted nucleic acid to centrifugation or other significant g forces, or administration of non-atmospheric pressure (e.g. a vacuum) to facilitate removal of undesired particulate matter or debris. Preferably, the extracted nucleic acid is filtered under gravity or manually-generated pressure to facilitate removal of undesired particulate matter or debris. In a particularly preferred embodiment, the nucleic acid sample is at least partly purified using particles which reversibly bind a target nucleic acid in the nucleic acid sample, as will be described in more detail hereinafter. Suitably, the target nucleic acid may subsequently be amplified by a nucleic acid amplification technique.

Nucleic acid amplification techniques are well known to the skilled in the art, and include but are not limited to polymerase chain reaction (PCR); strand displacement amplification (SDA); rolling circle amplification (RCA); nucleic acid sequence-based amplification (NASBA), Q-β replicase amplification; helicase-dependent amplification (HAD); loop-mediated isothermal amplification (LAMP); nicking enzyme amplification reaction (NEAR) and recombinase polymerase amplification (RPA), although without limitation thereto. As generally used herein, an "amplification product" refers to a nucleic acid product generated by a nucleic acid amplification technique.

Many nucleic acid amplification techniques cycle the nucleic acid sequence amplification procedure through different temperatures (for example 95° C. for denaturation, 72° C. for primer annealing and 42° C. for template extension) during each round of amplification, thereby requiring a thermal cycler for the technique. However, some nucleic acid amplification techniques may be isothermal, such as SDA, LAMP, NEAR, HAD, RCA and RPA, thereby obviating the need for a thermal cycler. Accordingly, in some embodiments the method and kit utilize isothermal nucleic acid sequence amplification.

Isothermal nucleic acid amplification assays, like loop-mediated amplification (LAMP), are increasingly used on commercially available portable molecular diagnostic platforms. Although LAMP is often compared to polymerase chain reaction (PCR), a common nucleic acid amplification assay, there are notable differences that support LAMP as an ideal diagnostic tool for POC testing. Foremost, gene-based assays like PCR require benchtop machinery to provide sufficient power to support rapid thermal cycling between relatively large temperature extremes, i.e., >90° C. for heat denaturation of the double stranded DNA and ~50-60° C. for primer annealing and extension. Unlike PCR, LAMP does not require heat denaturation of ds DNA and amplifies DNA under isothermal conditions i.e., 65° C. for 30 minutes. LAMP classically requires 4 separate primers: forward inner primer (FIP), forward outer primer (F3), backward inner primer (BIP), backward outer primer (B3) (Notomi, T. et al., 2000, Nucleic Acids Res. 28: E63). LAMP can be accelerated dramatically by the use of "loop" primers homologous to loops in the LAMP amplicon (Nagamine, K. et al., 2002, Mol. Cell. Probes 16:223-229). After FIP anneals to the complimentary ds DNA target at 65° C. (the condition of dynamic equilibrium for dsDNA) the intrinsic strand displacement of activity of the DNA polymerase initiates the complex LAMP amplification cascade through self-priming of loops in the amplicon, and additional priming with available inner primers.

LAMP is relatively insensitive to inhibitors commonly found in environmental and food sample matrices like polysaccharides, cellulose, humic acids and heavy metals (Wilson, I. G. et al., 1997, Applied and environmental microbiology 63.10:3741) enabling simple and field adaptable procedures (i.e., crude cell lysis) to extract nucleic acid from a sample for downstream analysis (G. H., 2009, The Federation of European Biochemical Societies Journal. Vol. 28-9624-0. p. 1-171). LAMP technology is rapid and can detect pathogens in 30 minutes or less while maintaining robust and sensitive detection of target DNA.

The methods and devices disclosed herein can be carried out using a variety of known isothermal amplification reactions, as well as thermocycling amplification techniques such as PCR and asymmetric PCR. Examples of isothermal amplification include, but are not limited to, Rolling Circle Amplification (RCA), Recombinase Polymerase Amplification (RPA), Strand Displacement Amplification (SDA), and Loop-Mediated Isothermal Amplification (LAMP). Other examples include nucleic acid sequence-based amplification (NASBA), transcription mediated amplification (TMA), and helicase dependent amplification (HDA). Yet another example is cross-priming amplification (CPA). CPA is discussed in more detail in Fang et al. (Cross-Priming Amplification for Rapid Detection of *Mycobacterium tuberculosis* in Sputum Specimens, *Journal of Clinical Microbiology*, March 2009, p. 845-847 Vol. 47, No. 3) and Xu et al. (Cross Priming Amplification: Mechanism and Optimization for Isothermal DNA Amplification, Scientific Reports, February 2012, Vol. 2 No. 246), both of which are hereby incorporated by reference in their entirety for their disclosure of CPA.

LAMP can be carried out using DNA or RNA (RT-LAMP). LAMP can amplify nucleic acids from a wide variety of samples. These include, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); plant materials; biological warfare agent samples; research samples (for example, the sample may be the product of an amplification reaction, for example general amplification of genomic DNA); purified samples, such as purified genomic DNA, RNA, proteins, etc.; raw samples (bacteria, virus, genomic DNA, etc.); as will be appreciated by those in the art, virtually any experimental manipulation may have been done on the sample. Some embodiments utilize siRNA and microRNA as target sequences (Zhang et al., J Cell Physiol. (2007) 210 (2): 279-89; Osada et al., Carcinogenesis. (2007) 28 (1): 2-12; and Mattes et al., Am J Respir Cell Mol Biol. (2007) 36 (1): 8-12, each of which is incorporated herein by reference in its entirety).

Some embodiments utilize nucleic acid samples from stored (e.g. frozen and/or archived) or fresh tissues. Paraffin-embedded samples are of particular use in many embodiments, as these samples can be very useful, due to the presence of additional data associated with the samples, such as diagnosis and prognosis. Fixed and paraffin-embedded tissue samples as described herein refers to storable or archival tissue samples. Most patient-derived pathological samples are routinely fixed and paraffin-embedded to allow for histological analysis and subsequent archival storage.

The target analytes can be nucleic acids. A nucleic acid will generally contain phosphodiester bonds (for example in the case of the target sequences), although in some cases, nucleic acid analogs are included that may have alternate backbones, comprising, for example, phosphoramide (Beaucage et al. Tetrahedron (1993) 49 (10): 1925 and references therein; Letsinger, J. Org. Chem. (1970) 35:3800; Sprinzl et al., Eur. J. Biochem. (1977) 81:579; Letsinger et al., Nucl. Acids Res. (1986) 14:3487; Sawai et al, Chem. Lett. (1984) 805; Letsinger et al., J. Am. Chem. Soc. (1988) 110:4470; and Pauwels et al. Chemica Scripta (1986) 26:141), phosphorothioate (Mag et al., Nucleic Acids Res. (1991) 19:1437; and U.S. Pat. No. 5,644,048), phosphorodithioate (Briu et al., J. Am. Chem. Soc. (1989) 111:2321, O-methylphophoroamidite linkages (see Eckstein, Oligonucleotides and Analogues: A Practical Approach, Oxford University Press), and peptide nucleic acid backbones and linkages (see Egholm, J. Am. Chem. Soc. (1992) 114:1895; Meier et al., Chem. Int. Ed. Engl. (1992) 31:1008; Nielsen, Nature, (1993) 365:566; Carlsson et al., Nature (1996) 380:207, all of which are incorporated herein by reference in their entirety). Other analog nucleic acids include those with bicyclic structures including locked nucleic acids, Koshkin et al., J. Am. Chem. Soc. (1998) 120:13252 3); positive backbones (Denpcy et al., Proc. Natl. Acad. Sci. USA (1995) 92:6097; non-ionic backbones (U.S. Pat. Nos. 5,386,023, 5,637,684, 5,602,240, 5,216,141 and 4,469,863; Kiedrowski et al., Angew. Chem. Intl. Ed. English (1991) 30:423; Letsinger et al. J. Am. Chem. Soc. (1988) 110:4470; Letsinger et al., Nucleoside & Nucleotide (1994) 13:1597; Chapters 2 and 3, ASC Symposium Series 580, Ed. Y. S. Sanghui and P. Dan Cook; Mesmacker et al., Bioorganic & Medicinal Chem. Lett. (1994) 4:395; Jeffs et al., J. Biomolecular NMR (1994) 34:17; Xu et al., Tetrahedron Lett. (1996) 37:743) and Ron-ribose backbones, including those described in U.S. Pat. Nos. 5,235,033 and 5,034,506, and Chapters 6 and 7, ASC Symposium Series 580, Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are herein expressly incorporated by reference. These modifications of the ribose-phosphate backbone may be done to facilitate the addition of labels or other moieties, to increase or decrease the stability and half-life of such molecules in physiological environments, etc.

EXPERIMENTAL EXAMPLES

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention and are not to be construed as limiting in any way the remainder of the disclosure.

Example 1: Point-of-Care Electroflotation of Dispersed, Low Tolerance Pathogens Improves Detection Rates by Loop Mediated Isothermal Amplification Electrode Arrays The feasibility and efficacy of the electroflotation system relies largely on electrode arrays to stably support electrolysis reactions in a highly corrosive environment without material degradation (i.e., anodic corrosion) and material property changes (i.e. decreased surface conductivity). Platinum coated titanium electrode arrays demonstrated superior performance during electroflotation treatments without any signs of corrosion and supported stable current densities without any additional protective coating or surface modifications. Conductive PDMS, carbon conductive paste, and silver filled epoxy were evaluated with electrochemical tests, SEM, and EDS as corrosion resistant coatings to protect exposed electrode metal on custom PCB electrode arrays. While conductive coatings work for industrial applications like creating electrical pathways, or as stand-alone electrodes, none of the tested corrosion inhibiting coatings were capable of long-term corrosion protection for electroflotation treatment conditions. The manufacturing costs of platinum coated titanium electrode arrays are more expensive ($33.00 per unit) when compared to PCB electrode arrays ($11.00 per unit), but last longer and do not require additional costs and labor to perform post processing steps i.e., screen printing corrosion inhibiting coatings. Innovations in production and development of electrochemical industrial titanium anodes supports prototyping applications when low cost and low volume manufacturing are necessary. Advances in technology that allow normally large scaled industrial products to be scaled down while remaining feasible demonstrates a promising future between industry and university research.

Foundational Electroflotation Experiments

Detection of nucleic acid amplification model LAMP can be enhanced by extracting and concentrating small quantities of bacteria dispersed in ecological-scale samples using a portable, automated, self-contained electroflotation system. Electroflotation treatment may use different chemical additives to improve aggregation or resistance of bacteria to shear, or different electrolysis conditions . . .

Effect of Pluronic on Electroflotation

The addition of a non-ionic surfactant (Pluronic® F-68) to EF treatments improved concentration of $E.\ coli$ 25922 and therefore improved detection rates of $E.\ coli$ 25922 by LAMP. The most impressive effect of adding Pluronic to EF samples, observed for the addition 0.1 g $L^{-1}$ Pluronic F-68 to $10^3$ CFU/mL bacterial quantities and subjected to 20 minutes low turbulence EF treatment, increased detection rates from 25% to 92.59%.

The mechanism by which Pluronic F-68 improves concentration of dispersed bacteria during flotation was not investigated. Interestingly, one study reports the use of surfactants to improve electro-kinetic stability of electrodes in lab-on-chip microdevice by promoting smaller bubble diameters and also more rapid bubble detachment from the electrode surface (Lee, H. Y. et al., 2014, Electrophoresis 35:1782-1789). While this effect was not measured directly, visual observation confirmed that larger bubbles sporadically detaching from electrodes occurred less frequent. This suggests that the effect of Pluronic to improve concentration of bacteria by EF extends beyond bubble-particle interactions by enabling quicker bubble detachment likely resulting in overall smaller and more uniformly sized microbubbles.

Pluronic F-68 is a non-ionic surfactant added to cell cultures to reduce shear forces and also reduce bacteria attachment to glass. Surfactants modify the surface tension forces that typically attract, stress or disperse biomaterial are commonly added to bioreactors to acrate cell cultures and protect cells from shear forces that result in cell lysis and death (Walls, P. L. L. et al., 2014, Integr. Comp. Biol. 54:1014-1025). The exact molecular mechanism by which Pluronic F-68 protects cells but it is unknown, but believed to be attributed to Pluronic F-68 masking the hydrophobic properties of the cell membrane. By design, surfactants interplay with bubbles result in local gradient changes in surface tension on the bubble surface so that a bubble will slide passed a cell with lowered interactions and collision efficiency (Walls, P. L. L. et al., 2014, Integr. Comp. Biol. 54:1014-1025). Theoretically, this should prevent bubble-cell attachment and decrease flotation efficiency. In contrast, Pluronic F-68 significantly improved EF concentration efficiency. Pluronic F-68 is an amphiphilic molecule that can self-assemble into microstructure micelles (Farías, T. et al., 2009, Colloids Surfaces A Physicochem. Eng. Asp. 345:51-57). Surfactant micelles can encapsulate other molecules and has been used widely for the solubilization of drugs and drug delivery (Fan, W. et al., 2012, Int. J. Nanomedicine 7:1127-1138). Similarly, it is conceivable Pluronic micelles formed around detectable cell material (i.e., free DNA, lipids, cell fragments) during EF treatments. The observed increased detection rates by LAMP may be attributed to the concentration of detectable cell material otherwise not observed in corresponding EF treatments without Pluronic.

Flocculation and Effects on Electroflotation

Chitosan was added to electroflotation treatments to support aggregation of dispersed bacteria, which can result in substantial increase in particle (i.e., bacteria) quantity recovered. Research using chitosan as a bacterial flocculation agent for $E.\ coli$ suspensions of $10^9$ CFU/mL suggests that optimal concentrations occur between 20-80 mg/g of cell dry weight depending on other factors like pH and degree of chitosan polymerization (Strand, S. P. et al., 2001, Biomacromolecules 2:126-133). Predicting adequate chitosan concentrations based on the dry weight of cells is impractical when conducting EF on environmental samples containing unknown quantities of dispersed bacteria at low titers ($<10^2$ CFU/mL). In other reports optimal chitosan or polymer concentration was found to be 10-20 ug/billion cells, 25-75 g/L (Pearson, C. R. et al., 2004, Biotechnol. Bioeng. 87:54-60), 20 mg/g of $chlorella$ (Zhou, W. et al., 2016, ALGAL 18:7-14). It is generally agreed that small increases or decreases in polymer dosage can have a large effect on the stabilization of the dispersed system and significantly affect the absorption rates of the flocculant to the substrate, however there is a lack of agreement on specific optimal chitosan concentrations reported in literature. This can be partially attributed to the challenges and complexity of quantifying properties of a dispersed colloidal system including the disagreement about the fundamental mechanism by which chitosan binds suspended solids; by bridging (Yang, Z. et al., 2012, Water Res. 46:107-114) or by charge neutralization (Barany J. et al., 2004, Adv. Colloid Interface Sci. 111:117-29).

Chitosan has previously been used to flocculate large quantities of bacteria ranging from $10^7$-$10^9$ CFU/mL. This is up to 7 orders of magnitude greater than the bacterial concentrations used in EF treatments ($10^2$-$10^4$ CFU/mL). To increase the likelihood of chitosan interacting with dilute suspension of bacteria, a relatively large dose of chitosan proportional to bacteria was added to EF treatments. For EF treatments containing ~$10^2$ CFU/mL $E.\ coli$, 0.01 or 0.1 g $L^{-1}$ was added to flocculate ~38,000 bacterial cells (the approximate quantity of $10^2$ CFU/mL cells dispersed in 380 mL of media).

Adding chitosan in large concentrations may have other benefits as well. Firstly, by the common "jar test method" $10^9$ CFU/mL cell suspensions and chitosan incubate together as a stationary culture for 24 hours during which cells are removed via sedimentation (Strand, S. P. et al., 2003, Colloids Surfaces B Biointerfaces 27:71-81). Predictively, flotation would counteract any flocculation achieved by sedimentation and therefore a larger dosage of chitosan may be required for optimal flocculation. Secondly, chitosan has lower solubility in tested EF media (0.1 M potassium phosphate buffer) due to the presence of buffering salts that bind to chitosan counterions (anions) resulting in charge neutralization (Kong, M. et al., 2010, Int. J. Food Microbiol. 144:51-63). Reduced solubility may decrease chitosan interactions with bacteria, and therefore a larger dosage of chitosan may be required for optimal flocculation. Thirdly, to maintain EF treatments a rapid process, the incubation period with chitosan restricted to 20 minutes. This incubation time is much shorter than previous studies (>2 hours) using chitosan as a flocculant for biological materials and therefore a larger dosage of chitosan may be required for optimal flocculation. Finally, studies report using much larger cell concentrations and therefore a larger dosage of chitosan may be required for optimal flocculation. For these reasons combined, chitosan was used in concentrations of 0.1 g L$^{-1}$ and 0.01 g L$^{-1}$ totaling 0.038 g chitosan and 0.0038 g chitosan to flocculate approximately 38,000 cells.

Preventing LAMP Inhibition by Chitosan

Despite LAMP resiliency against many common inhibitors, chitosan significantly inhibited detection by LAMP. Polysaccharides commonly found in environmental samples and plant matter are notorious inhibitors of nucleic acid amplification like PCR and competitively bind to template DNA, DNA polymerases and primer binding sites, preventing the initiation of DNA amplification. Diluting the sample can lower the concentration of inhibitors, however, this method is impractical for this application because improved detection is realized by concentrating a sample, not diluting. Unfortunately, by design, inhibitors that have aggregated during flocculation may also be concentrated during EF treatments.

The addition of chitosan as a flocculant to EF treated samples completely inhibited LAMP assays at concentration greater than 5×10$^{-4}$ mg/mL. At pH less than ~6.2 and below chitosan's pKa (~pH 9.5), chitosan has a strong positive charge and will bind strongly to negatively charged anions including template DNA inhibiting isothermal nucleic acid amplification. This approach to prevent LAMP inhibition by chitosan was adapted from a method that successfully extracted DNA on microchips lined with chitosan coated silica beads (Cao, W. et al., 2006, Anal. Chem. 78:7222-7228). In their system, when the buffer flowing through microchannels of the device was pH 5, DNA bound to chitosan coated beads, and then eluted from the beads at pH 10. This method was particularly desirable because it does not require downstream DNA purification or extraction methods to remove inhibitors. The pH can be titrated in the same tube as the recovered EF sample. This aligns nicely with platforms like the BioRanger™ that has a heat block capable of lysing cells at 100° C. so that all methodologies in this research, including DNA extraction, can be done in the field.

Safety Concerns

During EF treatments, electrolytically produced hydrogen and oxygen gases are allowed to mix in the flotation chamber (vented to the atmosphere) and gas trap creating a potentially hazardous scenario. While the lack of ignition sources and small diameter of the solid steel ejection port make ignition of the mixture unlikely, an analysis of the worst-case explosion risk within the EF cartridge was also conducted. In this worst-case scenario, the maximum pressure within the vessel was estimated for the case of an instantaneous and complete combustion of a perfect stoichiometric ratio of hydrogen and oxygen gas in the vessel headspace, assuming no venting of pressure/fluid through the ejection port (Adiabatic Isochoric Constant Combustion; AICC) (Lautkaski, R., 2005, Project Report). In the analysis, a final temperature from an initial ambient temperature (25° C.) of the stoichiometric hydrogen/oxygen mixture, and the temperature change based on the enthalpy of combustion of hydrogen and constant volume specific heat of water vapor resulting from the explosion was estimated. The maximum pressure was estimated from this temperature value using the ideal gas law and the total number of molecules of water vapor resulting from explosion of the stoichiometric mixture of hydrogen and oxygen initially at 1 atmosphere of pressure.

The maximum pressure was then used to estimate the maximum stress in the cylindrical vessel, as the orthogonal sum of the hoop stress and axial stresses. The estimated maximum stress (29.9 mPa) was then compared to the yield stress of the acrylic (69 mPa), to obtain a safety factor of 2.3, indicating no risk of explosion of the vessel under the above conservative assumptions.

The materials and methods employed in these experiments are now described.

PCB Electrode Arrays

For this design, electrolysis reactions were supported on planar, inert gold-plated PCB electrode arrays designed using a PCB CAD software (EAGLE, Autodesk, Mill Valley, California, USA) (FIG. 6A, FIG. 6B) patterned on custom printed circuit board (PCB) fabricated by a commercial manufacturer (OSH Park, Lake Oswego, OR, USA). The electrodes are arranged in horizontal pattern of concentric rings alternating between anode and cathode and separated by a space of approximately 1 mm. Solder mask material was used to cover all of the conductors on the surface except for a grid of plated vias perforating the board in circular patters around the perimeter of each conductive track. Conductive polymers were then printed into the vias to protect the underlying/exposed metal, and to provide electrical contact to the electrolyte. Electrodes were housed in a custom milled acrylic base that connects to the EF cartridge. A silicone gasket pressed between the cartridge and the base provided a seal to prevent leakage of the media. The housing assembly for the PCB electrodes was different than the final EF system housing design, primarily to enable connection to the different electrode arrays manufactured in the respective implementations.

Electrode Cleaning

To remove contaminants like ionic salts, oils or other particulates that could result in delamination of the conductive coatings, the PCB electrode arrays were cleaned using ultrasonic cavitation. The PCB arrays were placed in a beaker containing acetone inside the chamber of a CUBEX Sonic-3D for 5 min at 40 kHz at 25° C. After sonication, the electrodes were rinsed liberally with DI water, then dried and stored in sterile petri dishes.

Methods to Evaluate Corrosion Inhibiting Coatings

The following sections describe the materials and methods used to evaluate conductive pastes and adhesives as corrosion-resistant coatings for PCB electrode arrays:

1. Silver filled conductive epoxy
2. Carbon conductive paste
3. Graphite filled silicone While extensive testing was done using PCB electrode arrays, the final electrode arrays selected for use in electroflotation experiments were commercially manufactured titanium platinum electrode arrays. Characterization of electrolysis on the titanium platinum (TiPt) electrodes is summarized at the end of this section.

Methods to Evaluate Ag Epoxy

A sample EP21TDCS Silver Filled Epoxy was obtained from Masterbond (Hackensack, NJ, USA) as a previously cured sample on a glass slide.

Electrolytic Cell

Electrolysis is a process by which thermodynamically favored redox reactions are reversed by the application of an external electrical potential/energy. The relative thermodynamics and kinetics of different redox reactions with respect to the applied potential will determine which of the components in the electrolyte or electrodes are oxidized or reduced, and the rates at which these reactions occur. As a rule of thumb, electrolysis will occur first for paired half reactions with the nearest reduction potentials, though if one or both of these reactions require significant activation energy an overpotential will be required to support the desired reaction rates. However, application of overpotentials can result in undesirable redox reactions such as corrosion of electrodes or formation of reactive chlorine species.

Figure 7:
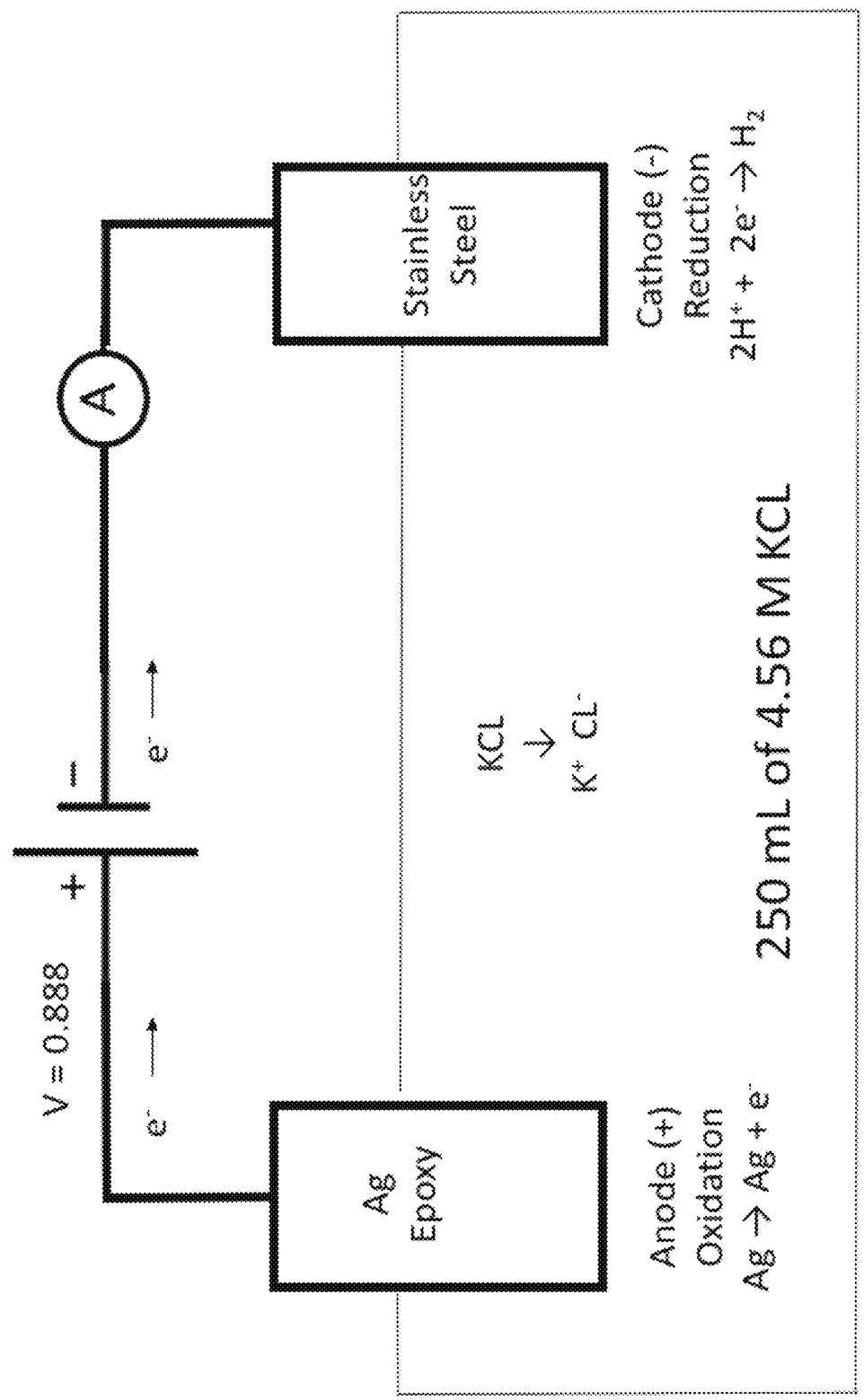
FIG. 7 depicts an electrolytic cell setup for oxidation of Ag epoxy.
Figure 8:
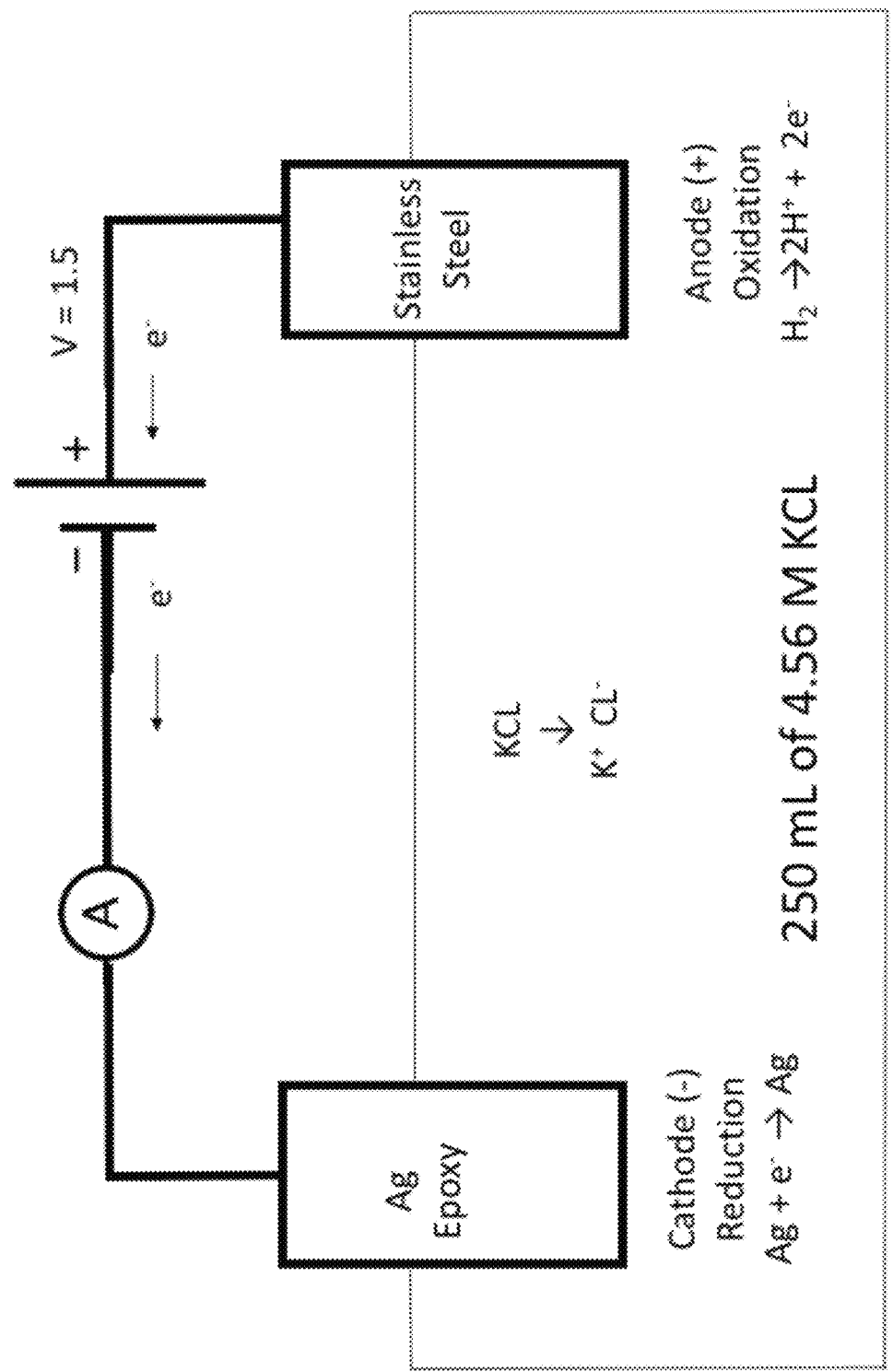
FIG. 8 depicts an electrolytic cell setup for reduction of Ag epoxy.

A simple electrolysis cell was constructed to examine the cyclic oxidation and reduction of silver epoxy. A silver epoxy electrode and stainless-steel counter electrode were submerged in 250 mL of a saturated KCl solution (4.56 M). A programmable DC power supply (Model E3632A, Agilent Technologies, Santa Clara, CA, USA) was used to apply desired potential, and handheld multimeter (Model 115/EFSP, Fluke Corporation, Everett, WA, USA) was used to measure the resulting current as shown for corresponding oxidation (FIG. 7) or reduction (FIG. 8) processes. Initially an oxidative potential of 0.888 V was applied to the silver epoxy electrode relative to the steel electrode, and current monitored for 180 minutes. Then to recover the reduced elemental silver, a reduction potential (−1.5V) for 180 minutes was applied, followed again by the 0.888 V oxidation potential for 180 minutes.

In the Constructed Cell:

$$E°_{cell} = E°_{oxidation} + E°_{reduction}$$

$$E°_{reduction}: 2H^{1+}_{(aq)} + 2e^- \rightarrow H_{2(g)} \quad E° = 0.00 \text{ V} \qquad \text{Eq. 1}$$

$$E°_{oxidation}: AgCl + e^- \rightarrow Ag + Cl^- \quad E° = 0.22 \text{ V} \qquad \text{Eq. 2}$$

Scanning Electron Microscopy & Energy Dispersive X-Ray Spectroscopy

Corrosion morphologies were imaged using scanning electron microscopy (SEM), (Hitachi S-4800 Field Emission model) followed by energy dispersive X-ray spectroscopy (EDS) (Oxford INCA X-Act EDS system) to measure the changes in compositional characteristics of the Ag epoxy electrodes after each 180-minute period of oxidation and reduction. SEM and EDS imaging were conducted at the Biological Electron Microscopy Facility in conjunction with the Pacific Biosciences Research Center at the University of Hawaii at Manoa. SEM allows for high resolution imaging of surface structures with a nanometer range resolution. EDS is a semi-quantitative analysis in which the energy of backscattered electrons images resulting from elastic collisions with atomic nuclei of different atomic numbers can be used to infer presence and composition of different elements on the material surface. The analysis is confined to a user set SEM window area and results show what elements are present in the material and relative percent (%) compositions (Hafner, B. 2006, *Characterization Facility, University of Minnesota* (2006): 1-26). EDS is a valuable technique to evaluate effects of corrosion, providing analysis of chemical composition of metal oxides during passivation of the metal (Zarras, P. et al., 2003, Radiat. Phys. Chem. 68:387-394) (Scheithauer, U., 1991, Anal. Chem. 341:445-448). SEM visualizes morphology and chemical composition of a material, and in this application, can show changes over time under different conditions and material degradation in a corrosive environment (Wessling, B. et al., 1999, Electrochimica Acta 44.12:2139-2147).

Methods to Evaluate Carbon Conductive Paste (CCP)

CCP 7102 was purchased from DuPont. It is a conductor with low sheet resistivity (20-30 ohms/sq/mil), high stability and rated to exhibit excellent adhesion to many types of substrates. 7102 is a black paste with high viscosity (60-125 Pa·S) and composed of dipropylene glycol methyl ether (60-70%), carbon black (10-20%), graphite (10-20%), polyether resins (10-20%) and small percent fatty acid salts of polyamine (0.1%-1%). CCP's generally have a hydrophobic surface characteristic due to the presence of lipophilic binders. Furthermore, the higher the lipophilic percent composition in the CCP, the slower the rate of charge transfer within the material and on the surface. Therefore, by reducing the amount of liquid in the CCP or subjecting the CCP to electrolysis which induces surfaces hydrophilization, the more rapid the charge transfer (Švancara, I. et al., 2009, Electroanalysis 21:7-28). Based on the composition of CCP 7102 as described in the MSDS, appropriate volumes of graphite power (G67-500, Grade 38, Fisher Chemicals) were added to 7102 and vigorously mechanically mixed to achieve a final composition of 50% graphite. CCP 7102 was screen-printed to fill and cover the exposed vias in the cleaned PCB electrode array using an AMI/PRESCO manual screen printer with a vacuum chuck. The stainless-steel screen/stencil was designed using a CAD software (EAGLE, Autodesk, Mill Valley, California, USA) and commercially fabricated (PCB Unlimited, Inc., Tualatin, OR, USA). After application, the PCB+CCP was cured in a box oven for 10 min at 120° C. The CPP application process was repeated twice curing the material each time.

The patterned and cured CCP+PCB electrodes were placed in a test EF system containing 400 mL of 0.1 M potassium phosphate electrolyte for 40 minutes with an applied potential of 4.21 V. Voltage, time and current (mA) data was logged using the microcontroller and custom developed Android OS application described in section 6.5 "Control System".

Methods to Evaluate Conductive Silicone

A two component, graphite filled electrically conductive Silicone, Mastersil 155 was purchased from Master Bond (Master Bond Inc., Hackensack, NJ, USA). Mastersil 155 is a silicone-based rubber with repeating units of poly-dimethyl-siloxane (PDMS). When cured, Mastersil 155 is rated to have a volume resistivity of 20-40-ohm cm$^{-1}$ and a conductivity of 20-30-ohm cm$^{-1}$ at 75° C. Mastersil 155 was patterned onto PCB electrode arrays using the same screen-printing method and stencil as described in the CCP methods section. After application, the PCB+conductive silicone was cured in a box oven for 30 min at 225° C.

Plasma treatments were conducted using a table top Harrick Plasma Basic Cleaner PDC-32G. Constant chamber pressure (250 mTorr), oxygen flow rate (1-1.5 kg/cm$^2$), and RF power (18 W) were all kept constant for plasma oxidation for a total plasma exposure time of 5 min. Immediately following plasma treatments Functional OH$^-$ groups were grafted onto the surface of conductive silicone by submerging the electrode array in PEG in a glass petri dish for 5 min. After grafting PEG, the electrode array was rinsed liberally with DI water and used in varying conditions of EF treatments. Images were taken of electrodes during electrolysis before and after plasma and grafting treatments. The patterned and cured conductive silicone+PCB electrodes were placed in a test EF system containing 400 mL of 0.1 M potassium phosphate electrolyte for 3-10 minutes with varying constant applied potentials (3-6 V). Voltage, time and current (mA) data was logged using the microcontroller and custom developed AndroidOS application described section 6.5 "Control System".

Platinum Coated Titanium Electrode Arrays

Figure 9:
FIG. 9 depicts a Solidworks drawing of TiPt electrode arrays (turquoise) with silicone base (grey). The outer diameter of the base is 76.5 mm.

Electrolysis reactions are supported on inert platinum (Pt) plated grade 1 titanium (Ti) electrodes (FIG. 2A) custom designed using a 3D CAD design software (SOLIDWORKS 2016, Waltham, MA) (FIG. 9) and fabricated by a commercial manufacturer (Baoji Qixin Titanium Co. Ltd, Maying Town, Weibin District, Baoji, Shaanxi, China). Carefully considering the spatial arrangement of electrodes is important to maintain high electrolysis efficiency (Nagai, N. et al., 2003, Int. J. Hydrogen Energy 28:35-41). To minimize ohmic losses and application of potentially corrosive overpotentials, electrodes are arranged in a horizontal pattern of concentric rings alternating between anode and cathode and separated by a spacing of 1 mm (Alam, R. et al., 2016, J. Water Process Eng. 12:78-88). The thickness of the electrodes was chosen to be 2 mm. The system consists of two individual sets of electrode arrays, each designed to generate bubbles in defined areas of the EF cell (see section "electroflotation cell and process"). The inner anode has a surface area (SA) of 826.05 $mm^2$ with corresponding cathode SA of 622.57 $mm^2$ while the outer anode has total SA of 880.02 $mm^2$ with corresponding cathode SA of 436.32 $mm^2$. Surface areas are calculated considering only the area of the exposed electrode face. Electrode arrays are housed in a custom engineered thermoplastic elastomer base (TPE) (3D Systems Inc., Atlanta, GA, USA) that electrically isolates adjacent electrodes from one another and provides a seal preventing leakage of electrolyte out of the EF cartridge and onto the attached electrical control system.

Methods to Evaluate Platinum Coated Titanium Electrodes

TiPt electrodes were tested at 20 minutes at high and low constant applied current in the EF cell (described in section 6.6) using a control feature to maintain a desired constant current (see section 6.5 "Control System"). These electrodes were used in all subsequent electroflotation experiments described in later sections. The stability and corrosion resistance were evaluated by observing how much the required potentials changed to support the designated current values over time i.e. high and low current settings. EF treatments performed at high turbulence flotation settings (see section 6.9) were used to evaluate high current settings i.e. 600 mA. EF treatments performed at low turbulence flotation settings (see section 6.9) were used to evaluate low current settings i.e. 300 mA. Voltage, time and current was recorded and logged using the EF system microcontroller and AndroidOS application. The logged current (mA) data from 3 experimental replicates at high and low current was averaged and reported.

Control System

Figures 2A, 2B:
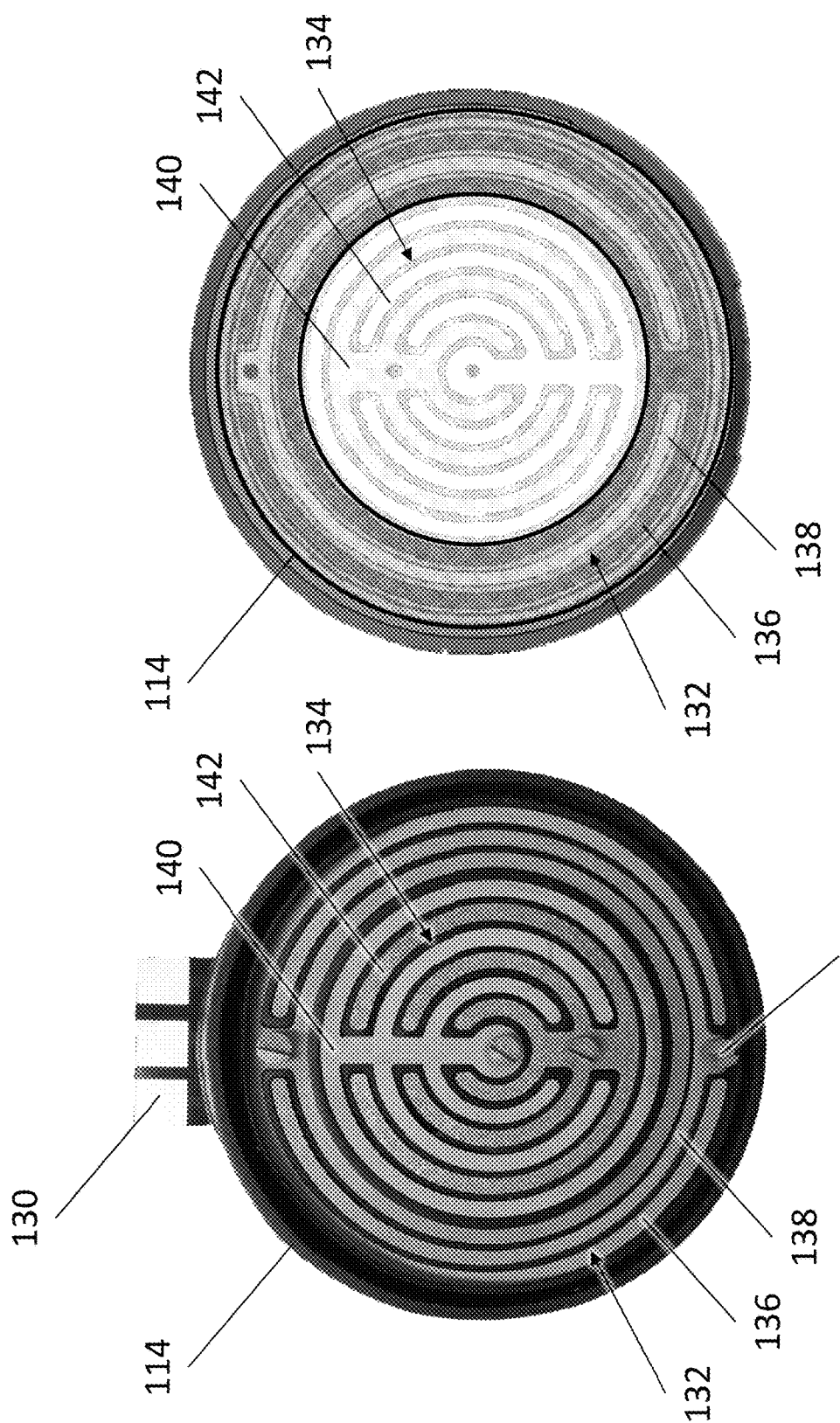
FIG. 2A and FIG. 2B depict an exemplary electrode array assembly.
Figure 10:
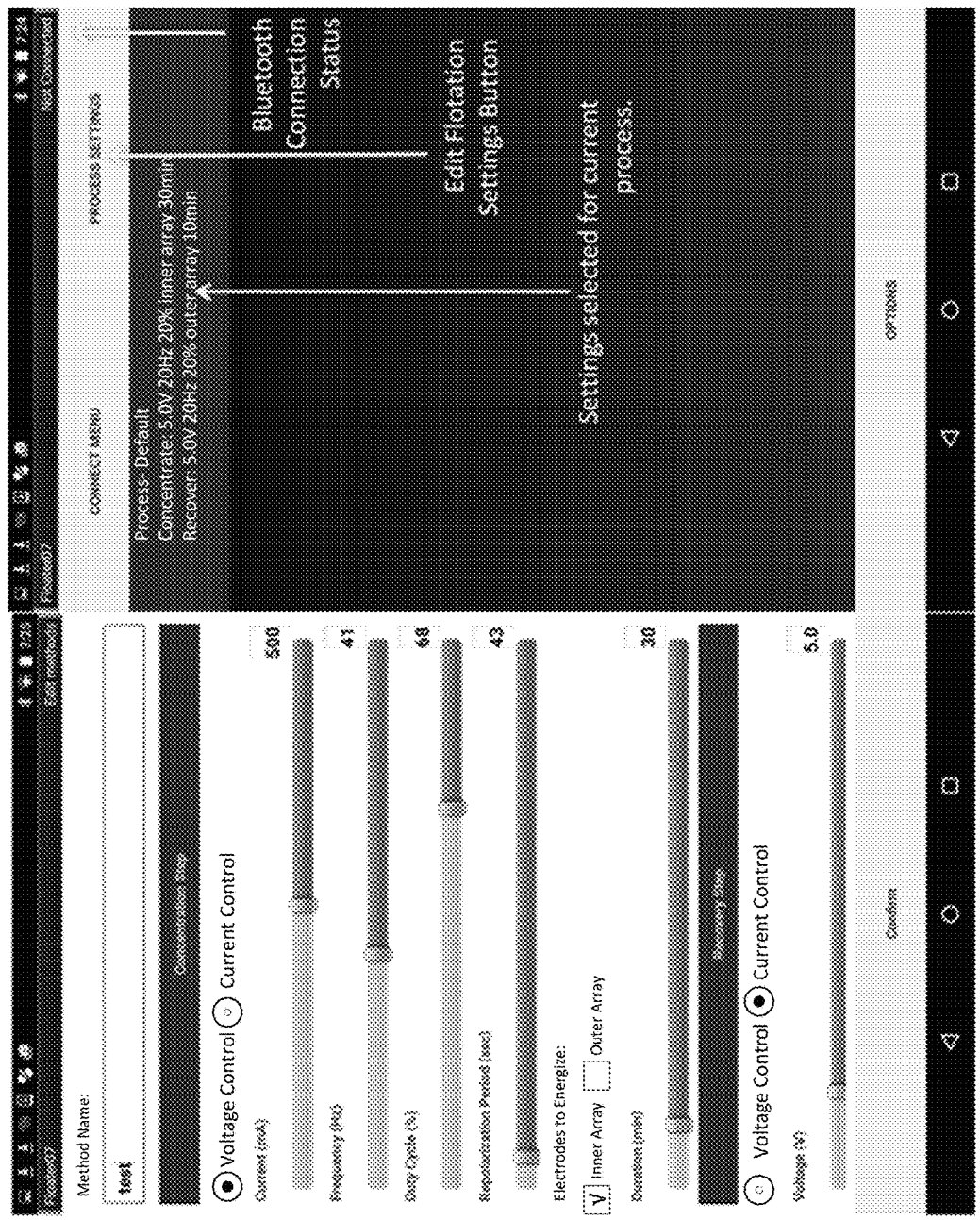
FIG. 10 depicts an AndroidOS application user interface. Home screen is shown on the right and process setting window is shown on the left.
Figure 11:
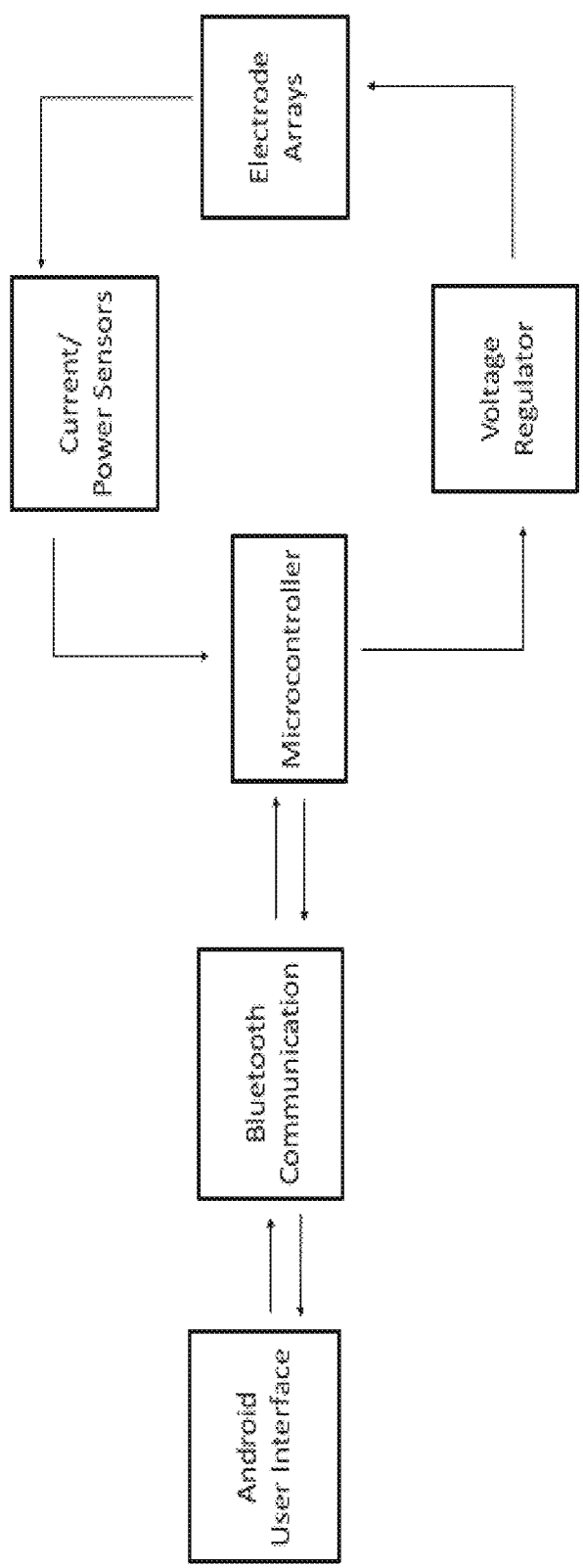
FIG. 11 depicts a block diagram of a control system information pathway.

Current through the electrode arrays is controlled with a custom circuit assembly connected to the electrodes with platinum plated titanium screws (FIG. 2A). The circuit is controlled with an 8-bit microcontroller (Atmega-328P, ATMEL Inc., San Jose, CA) interfaced through a Bluetooth modem (RN42, Microchip Technology, Chandler, AZ) to a custom Android application (FIG. 10) that allows user control of process parameters including process durations (min.), voltage (3.5-12 V), current (0-1000 mA), frequency (0-100 Hz), and duty cycle (1-100%). The current control feature allows a desired current (I) to be maintained throughout the EF process irrespective of the media composition/electrical characteristics, and subject to the constraints of the available voltage range. Feedback control of voltage (or current) on two sets of concentric electrode arrays is achieved by measuring cell currents and voltage with two bi-directional current/power monitors (INA219, Texas Instruments Incorporated, Sunnyvale, CA 94043), and adjusting the voltage output through a switching regulator (LT1373, Linear Technology Corporation, Milpitas, CA 93035) network controlled with a digital potentiometer. In general, the greater the applied voltage or current, the more vigorous the electroflotation process will be. An outline of communication and information transmission is demonstrated in a block diagram (FIG. 11). Current and voltages were recorded at the end of each pulse applied to the electrodes.

Electroflotation Cell for Automated Concentration and Recovery

The cylindrical electroflotation cell (FIG. 1) housing is made of custom machined cast acrylic tubing and rod where generated gas is partitioned into one of two headspaces: a collection chamber in the core of the cylinder that vents to the atmosphere, and a concentrically arranged trap where gas can accumulate to displace media from the collection chamber. After the sample is loaded into the flotation chamber (FIG. 3A), the electroflotation treatment consists of two main process events: (1) concentration step (FIG. 3B) and (2) recovery step (FIG. 3C). During the concentration step the inner set of electrode arrays are energized (FIG. 2B), allowing collimated microbubbles to flow upward directing particulates into the collection chamber. After a user defined duration (min.), the recovery step is initiated, and both the inner and the outer set of electrode arrays are energized such that gas also begins to accumulate in the trap. As gas accumulates in the trap, material concentrated in the collection chamber is displaced through a dispensing tube where it is collected by the user into defined volume fractions (mL).

Preparation of Bacterial Cultures and Media

As a model organism to test the efficacy of EF treatment, a non-pathogenic isolate of *E. coli* (ATCC strain 25922) was grown overnight on plate-count agar (Difco™) at 37° C. Colonies were then transferred into sterilized potassium phosphate buffer (0.1 M, pH 6.6) adjusted to achieve an absorbance of 0.13 at 600 nm as read on a commercially available spectrophotometer (Healthcare Ultraspec™ 10, General Electric, location). This absorbance was shown empirically to be equivalent to about $10^8$ CFU/ml ($\bar{x}=1.63\times10^8$ CFU/mL, s=$2.55\times10^2$ CFU/mL, n=3) through comparison to standard plate counting methods. Bacterial cultures and media were freshly prepared for each electroflotation experiment.

Preparation of Electroflotation Bacterial Suspension Samples

Phosphate buffer (0.1 M, pH 6.6) was used as the media to facilitate electrolytic charge transfer and moderate pH changes from half reactions at the electrodes. A conductivity (K) for this media of 12.8 mS/cm from acid dissociation and ionic conductivity data reported in the literature was inferred (Lide. D. R., 1994, CRC Handbook of Chemistry and Physics. 74th ed. CRC Press. p. 8-47, 5-91). Electrically conductive media is important to support high electrolysis rates efficiently with minimal over potential, and minimize corrosion and other undesirable redox reactions (Nagai, N. et al., 2003, Int. J. Hydrogen Energy 28:35-41; Chen, G. et al., 2004 September. Purif. Technol. 38:11-41). The pH was measured using an AB15 Plus meter (Accumet Basic, Fisher Scientific) and buffer was sterilized in an autoclave before inoculation. 380 mL of sterile phosphate buffer was inoculated with appropriate volumes of freshly prepared *E. coli* 25922 culture in 500 mL sterilized flasks to achieve the following bacterial suspension concentrations: $10^2$, $10^3$, $10^4$, $10^5$ or $10^6$ CFU/mL. To homogenously disperse bacteria in suspension, samples were mechanically shaken briefly (90 seconds) after inoculation and used promptly for subsequent electro-flotation experiments. Control samples were prepared identically to EF samples, except instead of recovery via media displacement, fractions were collected with pipettes directly from the freshly prepared media.

Electroflotation of *E. coli* 25922

Figure 12:
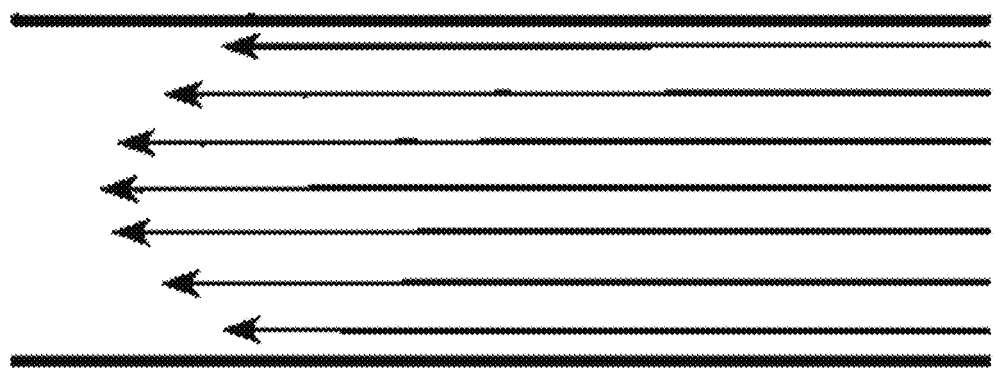
FIG. 12 depicts the behavior of bubble flux for low turbulence flotation conditions.
Figure 13:
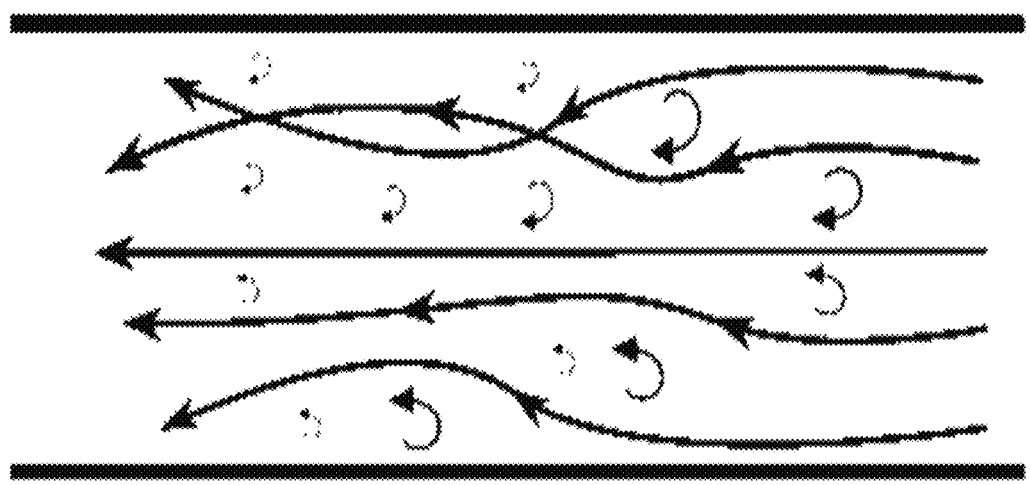
FIG. 13 depicts the behavior of bubble flux for high turbulence flotation conditions.

Prepared electro-flotation samples were gently poured into the electro-flotation chamber and sealed. To investigate the effects of varying EF treatment durations, samples were subjected to 10, 15, and 20 minutes of EF treatment. The "stirring effect" caused by rising clouds of bubbles (Zimmerman, W. B. et al., 2008, Recent Patents Eng. 2:1-8) can cause fluid to circulate, which may positively impact the collection efficiency by increasing particle/bubble collisions (Kyzas, G. et al., 2014, Processes 2:293-310; Walls, P. L. L. et al., 2014, Integr. Comp. Biol. 54:1014-1025; Alam, R. et al., 2016, J. Water Process Eng. 12:78-88) and rate of mass transport (Szpyrkowicz, L., 2005, Ind. Eng. Chem. Res. 44:7844-7853) by bubbles (Szpyrkowicz, L., 2005, Ind. Eng. Chem. Res. 44:7844-7853). On the other hand, when bubble flux exceeds a critical limit, hydrodynamic forces due to turbulence in fluid circulation acting on suspended cells can break fragile flocs of cell aggregates causing shear stress or damage to cells (Elias, C. B. et al., 1995, Chem. Eng. 50:2431-2440; Sowana, D. D. et al., 2001, Eng. Res. Des. 79:867-875; Nagai, N. et al., 2003, Int. J. Hydrogen Energy 28:35-41; Sharma, P. K. et al., 2005, Appl. Environ. Microbiol. 71:3668-3673). Furthermore, excessive mixing due to the "stirring effect" could prevent cells from concentrating at the surface of media in the column, decreasing recovery efficiency. In summary, low turbulence conditions are a gentle process producing bubbles in a "laminar" flow column (FIG. 12), but may result in slower or less efficient capture of suspended particles, while high turbulence conditions generate a "stirring effect" (FIG. 13) to increase cell-bubble collision, but may break apart aggregated cell flocs. The flux rate bubbles, defined by volumetric rate of bubbles passing through a cross sectional area at any given time point, is most directly related to current density at electrode surfaces (FIG. 13) (Chisti, Y., 2000, Trends Biotechnol. 18:420 432; Nagai, N. et al., 2003, Int. J. Hydrogen Energy 28:35-41; Chen, G., 2004 September. Purif. Technol. 38:11-41). It was observed that bubble flux and average bubble diameter were also dependent on frequency and duty cycle applied to electrodes. Lower frequencies and duty cycles, at the same current levels, generally resulted in smaller bubbles and less mass flux, as individual bubbles stopped growing and were more likely to randomly detach from electrode surfaces during the longer "off" periods.

Based on empirical observations of amount of turbulent mixing, I selected a "high turbulence" (HT) test condition to 500 mA/100 Hz/75% duty cycle for concentration and 650 mA/100 Hz/75% duty cycle for recovery. To achieve conditions with less turbulent mixing where bubble flux is highly collimated during concentration, I designated a "low-turbulence" (LT) test condition performed at 300 mA/20 Hz/30% for concentration and 600 mA/20 Hz/50% duty cycle for recovery. The reported currents were taken as the sum of the current through both inner and outer electrode arrays (where the current through the outer arrays was effectively 0 during the concentration step), measured at the end of the energized part of the cycle. A larger total current was always applied during recovery step because the current was distributed across both sets of arrays. In summary, inoculated EF samples were subjected to EF treatments at 27° C. varying duration (10, 15 and 20 minutes) for all bacterial concentrations ($10^2$-$10^4$ CFU/mL) at different levels of flotation turbulence (high, low) (Table I). Three experimental replicates were performed for each treatment. The summary and experimental outline are detailed in Table 1 and FIG. 14A and FIG. 14B.

TABLE I

Experimental matrix of tested EF treatment conditions

| Mixing Condition | CFU/mL | EF Duration (Min.) | Mixing Condition | CFU/mL | EF Duration (Min.) |
|---|---|---|---|---|---|
| Low Turbulence 300 mA 20 Hz 50% Duty Cycle | $10^2$ | 10 | High Turbulence 500 mA 100 Hz 75% Duty Cycle | $10^2$ | 10 |
|  |  | 15 |  |  | 15 |
|  |  | 20 |  |  | 20 |
|  | $10^3$ | 10 |  | $10^3$ | 10 |
|  |  | 15 |  |  | 15 |
|  |  | 20 |  |  | 20 |
|  | $10^4$ | 10 |  | $10^4$ | 10 |
|  |  | 15 |  |  | 15 |
|  |  | 20 |  |  | 20 |

Recovery of Electroflotation Treated Samples

To observe partitioning effects in electroflotated media, the first 3 mL displaced from every EF treatment condition were collected into individual 1 mL fractions in 1.5 mL Eppendorf tubes. DNA from all recovered fractions was extracted using crude cell lysate method (95° C. for 5 minutes) (Teh, C. S. J. et al., 2014, Sci. World J. 2014), followed by 15 seconds of low speed vortexing. The recovered samples were later used in downstream molecular testing in a LAMP assay to evaluate the recovery of detectable cellular material by EF.

Development of a Loop Mediated Isothermal Amplification (LAMP) Assay

For detection of *E. coli*, LAMP was used, a popular isothermal amplification chemistry that may be especially attractive for use in portable diagnostic systems (Kubota, R. et al., 2011, Biological Engineering Transactions 4.2:81-100; Kubota, R. et al., 2015a, Int. J. Mol. Sci. 16:4786-99). To target *E. coli* 25922 a previously published LAMP primer set (Teh, C. S. J. et al., 2014, Sci. World J. 2014) that was designated EcolC 3109_0 (Table II), targeting a conserved glycerate kinase coding region (EcolC 3109, Accession number: CP000946) of generic *E. coli* ATCC 8739 was modified. Evidently outer primers play a critical role in locally destabilizing inner primer annealing sites on template DNA to initiate the LAMP reaction cascade, so that proximity of outer primers to their corresponding inner primers can have a large effect on assay performance (Kubota, R. et al 2011, Biological Engineering Transactions, 4 (2), 81-100). Genome sequences returned from NCBI BLAST (blast.ncbi.nlm.nih.gov/Blast.cgi) for both ATCC 25922 and ATCC 8739 indicated that the forward outer primer (SEQ ID NO.1) target of EcolC 3109_0 was very distant from the FIP annealing site of EcolC 3109, suggesting a reason for poor performance that was observed for this primer set in the preliminary experiments.

5 alternative primer sets targeting the same single copy glycerate kinase gene from the *E. coli* ATCC 25922 genome sequence (NCBI GenBank, NZ_CP009072.1) was designed, including forward loop primers (LF-SEQ ID NO.12) as well as reverse loop primers (LB-SEQ ID NO.13). The top five modified primer sequences were generated using PrimerExplorer V4 software (PrimerExplorer, Eiken Chemicals, Tokyo, Japan, primerexplorer.jp/e/), and after preliminary screening (data not shown) the most promising primer set, designated EcolC 3109_1 (Table III), was selected for further use in this study. Experiments to compare performance of primer set EcolC 3109_1 to the original primer set EcolC 3109_0 were conducted using serially diluted DNA purified using a Wizard genomic DNA purification protocol (Promega Corportation, Madison, WI), from *E. coli* ATCC 25922 DNA. Absorbance (260 nm) of purified DNA was measured with a NanoDrop 1000 DNA spectrophotometer (Thermo Scientific) to estimate DNA concentrations. The copy number of template genomic DNA was estimated by mass, assuming a genome size of approximately 5.2 Mbp with 50.4% GC content, resulting in a genome mass of about 17 fentograms. Purity was determined by taking the absorbance ratios at 280/260 nm and 250/230 nm. All LAMP assays were conducted in triplicate.

TABLE II

Original EcolC 3109_0 LAMP Primer sequences (Teh, C. S. J. et al., 2014, Sci. World J. 2014) for amplification of the glycerate kinase gene region of generic Escherichia coli 25922

| Primer | Nucleotide Sequence (5' → 3') |
|---|---|
| Forward Outer (F3) | GGTAGATCGAACGGTCATCG (SEQ ID NO. 1) |
| Backward Outer (B3) | GGCCAGCAACGGATTACG (SEQ ID NO. 2) |
| Forward Inner (FIP) | CGCAGACTTCAAGCGTCACGATCGAAGGAACGGTG GATGC (SEQ ID NO. 3) |
| Backward Inner (BIP) | CCTTACCGGCGACGGGAAAACTTTTCAGGCGCGAC CAG (SEQ ID NO. 4) |
| Reverse Loop (LB) | TGAGATGGCGGCAGCAAGTG (SEQ ID NO. 5) |

TABLE III

Modified Ecol 3109_1 LAMP Primer sequences for amplification of the glycerate kinase gene region of generic Escherichia coli 25922.

| Primer | Nucleotide Sequence (5' → 3') |
|---|---|
| Forward Outer (F3) | GGCGAATGCCGTTATCCAG (SEQ ID NO. 6) |
| Backward Outer (B3) | CGTGACGCTTGAAGTCTGC (SEQ ID NO. 7) |
| Forward Inner (FIP) | CGCGCCTGAAAAGCGTAATCC (SEQ ID NO. 8) CGCATGACGAATCAGCTCTC (SEQ ID NO. 9) |
| Backward Inner (BIP) | CAATCACCGCCGTTTTCCCGT (SEQ ID NO. 10) CGATGGGCGAAACAGTGAAT (SEQ ID NO. 11) |
| Forward Loop (LF) | TGCTGGCGTCAAGTTTTGG (SEQ ID NO. 12) |
| Reverse Loop (LB) | CGCCGGTAAGGCCATAAAAA (SEQ ID NO. 13) |

LAMP Primer Reaction Conditions

All LAMP reactions using the modified primer set EcolC 3109_1 and original primer set EcolC 3109_0, were performed in 25 μL (total volume) containing 40 pmol of each inner primer (BIP and FIP) (SEQ ID NO.4, SEQ ID NO.10, SEQ ID NO.11 and SEQ ID NO.3, SEQ ID NO.8, SEQ ID NO.9), 5 pmol of each outer primer (B3 and F3) (SEQ ID NO.2, SEQ ID NO.7, SEQ ID NO.1, SEQ ID NO.6), 20 pmol of each loop primer (LB and LF where applicable) (SEQ ID NO.5, SEQ ID NO.13 and SEQ ID NO.12). Reactions were prepared by adding 5 μL of a stock primer solution and 5 μL of sample to 15 μL of commercially available Isothermal Mastermix with dye (Catalog No. ISO001, Optigene, Inc., Horsham, UK). All primers were synthesized commercially (Integrated DNA Technologies, Coralville, IA, USA). All reactions were performed in 0.1 mL TempPlate semi-skirt PCR 96-well Plates (Catalog No. 1402-9100, USA Scientific, Inc., Ocala, FL, USA) in a commercial real-time PCR machine (Applied Biosciences StepOnePlus™) incubated at 65° C. for 31 minutes. Fluorescence values were recorded every 30 seconds during the 31-minute reactions. The "threshold time" tr was estimated as the amount of time required for the fluorescence value to exceed a threshold value equivalent to the pooled average plus three standard deviations of the fluorescence values observed throughout reactions of triplicate negative control reactions (Kubota, R. et al., 2015a, Int. J. Mol. Sci. 16:4786-99; Kubota, R. et al., 2015b, Int. J. Mol. Sci., 16 (3), 4786-4799). Reported averages of tr values exclude assays with undefined tr values ($t_T$>31 minutes). Reactions were conducted in triplicate for each template DNA concentration and primer set, including for the non-template controls.

LAMP Primer Sequence Identity Among Generic E. coli Strains

To evaluate how conserved the primer annealing sites are among generic E. coli strains, in silico analysis was conducted on 58 published sequences of generic E. coli strains retrieved from NCBI GenBank database. The 58 sequences, including ATCC 25922, were aligned using BLASTn (blast.ncbi.nlm.nih.gov/Blast.cgi) against the modified primer set EcolC 3109_1. The BLASTn results were subsequently confirmed by multiple alignments of the sequences by using ClustalW v.2.1 (Conway institute UCD Dublin, Ireland, ftp.ebi.ac.uk/pub/software/clustalw2/) and BioEdit v7.2.6.1 sequence alignment editor software (North California State University, USA) and a percent match (%) value was calculated considering only the primer annealing site and not the entire target gene region. To verify the specificity of the modified primer set 3109_1 to E. coli, 26 previously published complete genomes (Lu, J. et al., 2014, J. Water Health 12:763-771) of non-E. coli strains were tested in silico using BLASTn. BLASTn results generated a percent query cover using BLAST's local alignment algorithm to scan the entire imputed (query) genome for sequence similarities between non-E. coli strains and primer set 3109_1 that could cause non-specific primer annealing.

Evaluation of LAMP Assay Using Electroflotation Treated Samples

For detection of E. coli 25922 in recovered fractions from electro-flotation treated samples, 5 μL of crude lysed sample from each fraction (1st, 2nd, 3rd mL) was directly used in an individual reaction tube (0.1 μL) under the previously described reaction conditions. Electroflotation experiments for each condition were conducted in triplicate. For every 1 mL fraction in each experimental replicate, 3 LAMP assays were performed. In parallel, a LAMP assay reaction curve was generated for control samples containing bacterial concentration of $10^2$-$10^6$ CFU/mL without electro-flotation treatment in order to compare differences in threshold times (tr) of samples subjected to varying electro-flotation treatment conditions (duration, turbulence level and initial inoculum level). Mean detection rates were calculated based upon the percentage of positive samples in 27 samples (9 samples/experiment) (Wang, H. et al., 2016, PLOS One 11:1-21). Detection was classified somewhat conservatively as a reaction with an observed threshold time (tr) less than 28 minutes to reject false amplifications due to primer selfannealing and other effects, even though false amplicons could readily be discriminated by melting temperature analysis (unpublished data).

LAMP Detection Distribution Between Collected Fractions

In all experiments, the EF treatments were designed to concentrate bacteria dispersed in 380 mL into 3 fractions (1 mL each). Evaluation of the detection rates in the different fractions could help determine the level of stratification of cellular component near the surface, and the possibility that cells can be confined in a thin layer at the media surface. To better interpret the efficiency of concentration, each 1 mL fraction (1st, 2nd, 3rd) collected from all experiments was analyzed individually for percentages of positive sample detection. Mean detection rates from each fraction were calculated based on the percentage of samples with observed $t_T$<28 minutes in 3 LAMP assays (3 assays/1 mL fraction), for each of the three experimental replicates at the given EF conditions.

Effect of Pluronic and Chitosan on LAMP

To test inhibitory effects on LAMP, varying concentrations of pluronic (0%, 0.05%, 0.1%, 0.5%, 1.0%, 2.0%) and chitosan (0, $5\times10^{-8}$, $5\times10^{-7}$, $5\times10^{-6}$, $5\times10^{-5}$, $5\times10^{-4}$, $5\times10^{-3}$ g $L^{-1}$) prepared in sterilized DI water and 0.1 M phosphate buffer (pH 6.0) respectively were added to individual LAMP assays. 25 μL reactions were prepared by adding 5 μL of a stock primer solution (Ecol 3109_1) and 5 μL of sample containing 4 μL of tested concentrations of pluronic or chitosan and 1 μL containing 0.2 ng of purified (Wizard genomic DNA purification protocol, Promega Corporation, Madison, WI) *E. coli* 25922 DNA to 15 L of commercially available Isothermal Mastermix with dye (Catalog No. ISO001, Optigene, Inc., Horsham, UK). All conditions were tested in triplicate including positive and negative controls.

EF Treatments+/−Pluronic F-68

To enhance viable cell recovery, variable concentrations (0.001, 0.01, 0.1, 1 g $L^{-1}$) of Pluronic (Pluronic®F-68, non-ionic surfactant, Thermo Fisher Scientific Inc., Waltham, MA, USA) was added to the prepared EF bacterial cultures ($10^2$, $10^3$ CFU/mL) and subjected to 15 min HT EF and 20 min LT EF. The 1st 3 mL displaced from every EF treatment condition were collected into individual 1 mL Eppendorf tubes. DNA from all recovered fractions was extracted using crude cell lysate method (100° C. for 5 min.) followed by 15 seconds of low speed vortexing. To increase DNA the quantity of DNA extraction, higher temperature (100° C.) was used for crude cell lysis whereas 95° C. was used in the foundational experiments section 6.10. For detection of *E. coli* 25922 in recovered fractions from EF treated samples, 5 μL of crude lysed sample was directly used in an individual LAMP assay following identical LAMP primer reaction conditions and primer set EcolC 3109_1 also detailed in Objective 1. For every 1 mL fraction, 3 LAMP assays were performed. Three experimental replicates were performed for each treatment condition.

EF treatment+/− (Chitosan+Pluronic)

Figure 15B:
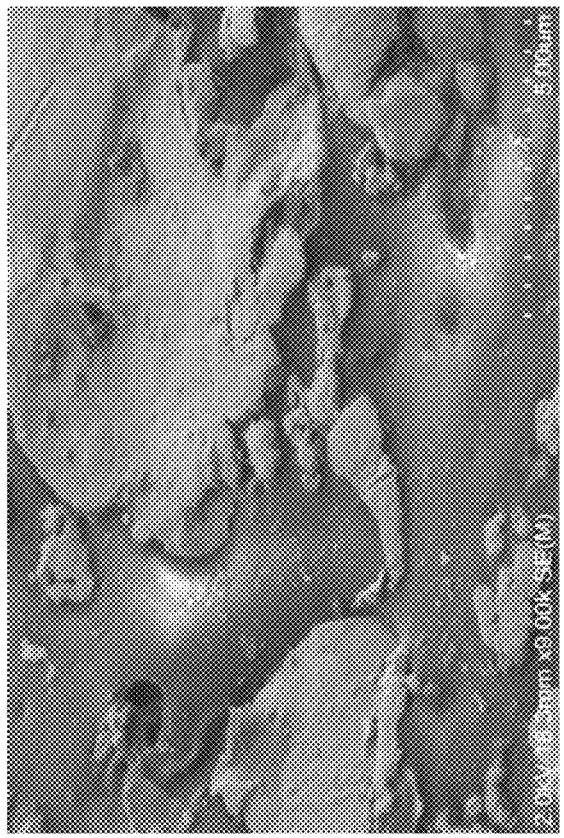
FIG. 15A and FIG. 15B, depicts SEM images of silver epoxy.

To aggregate cells producing shear protected flocs, variable concentrations of agricultural grade chitosan oligosaccharide (FIG. 15A, FIG. 15B) (soluble in pH 5-7) (Qingdao BZ Oligo Biotech Co., Ltd, Qingdao, China) (0.001, 0.01, 0.1, 1 g $L^{-1}$) was added to the prepared EF bacterial cultures ($10^2$ CFU/mL). Next, the cultures were placed on a shaker for 30 minutes at 50 rpm and then gently transferred to the EF cartridge and subjected to 20 min LT of EF treatment. Appropriate chitosan concentrations were prepared by serially diluting a stock concentration of 10 g $L^−$ chitosan. The 1st 3 mL displaced from the EF treatment condition was collected into individual 1 mL Eppendorf tubes. DNA from all recovered fractions was extracted using crude cell lysate method (100° C. for 5 min) followed by 15 seconds of low speed vortexing. To prevent LAMP inhibition, chitosan can be transformed from a DNA binding state to a DNA release state by adjusting the recovered fraction media pH (5.8) above the pKa (~9.5) of chitosan. To achieve this sample pH was adjusted from pH 5.8 to ~pH 10-10.5 by adding 99 μL of 1 M NaOH to each 1 mL fraction incubated at room temperature for 10 minutes followed by 30 seconds of medium speed vortexing. For detection of *E. coli* 25922 in recovered fractions from EF treated samples, 5 μL of crude lysed, adjusted pH 10 sample was directly used in an individual LAMP assay following identical LAMP primer reaction conditions using primer set EcolC 3109_1 as detailed in section 6.11.1 "LAMP Primer Reaction Conditions". For every 1 mL fraction, 3 LAMP assays were performed. Three experimental replicates were performed.

Eluting DNA from Chitosan by Increasing Sample pH

To test if changing the pH of chitosan containing samples could release DNA from chitosan and prevent LAMP inhibition by chitosan, simulated EF samples were prepared containing 0.1 g $L^{-1}$ Pluronic and varying concentrations of chitosan (0.01 and 0.1 g $L^{-1}$). Appropriate volumes of dissolved chitosan stock (10 g $L^-$ in sterile DI $H_2O$) was added to 0.1 M pH 6 phosphate buffer to achieve a chitosan concentration of 0.01 and 0.1 g $L^{-1}$ and distributed into 1 mL aliquots. Similarly, appropriate volumes of Pluronic was added to achieve 0.1 g $L^{-1}$ in all aliquots. Next, appropriate volumes of purified (Wizard genomic DNA purification protocol, Promega Corportation, Madison, WI) *E. coli* 25922 DNA was added to each 1 mL aliquots containing chitosan+Pluronic+phosphate buffer and let to sit for 10 minutes. Next, the pH of some (Table IV: sample C, D) simulated EF sample aliquots was adjusted from pH 6 to pH 10 by adding appropriate volumes of NaOH and letting stand at room temperature for 10 minutes. pH was verified using an AB15 Plus meter (Accumet Basic, Fisher Scientific). Individual 25 μL LAMP assays were prepared by adding 5 μL of varying samples as described in Table IV to 15 μL Isothermal Mastermix and 5 μL of a stock primer solution (Ecol 3109_1). Three experimental replicates were performed for each sample type. Negative controls did not contain DNA or chitosan, while positive controls contained DNA in pH 10 phosphate buffer titrated with NaOH.

TABLE IV

Experimental design to test if increasing pH prevents LAMP inhibition by

| | LAMP Assay Sample Descriptions | | | | | | | |
|---|---|---|---|---|---|---|---|---|
| Sample Type | *E. coli* 25922 DNA (ng) | DNA Volume (μL) | chitosan (g/L) | pH | DDnase Water (μL) | 0.1M Phosphate Buffer (μL) | 1M NaOH adjustment | Total Sample Volume (μL) |
| Negative | 0 | 0 | 0 | | 5 | 0 | no | 5 |
| Positive | 0.2 | 1 | 0 | 10 | 4 | 0 | no | 5 |
| A | 0.2 | 1 | 0.01 | 6 | 0 | 4 | no | 5 |
| B | 0.2 | 1 | 0.1 | 6 | 0 | 4 | no | 5 |

TABLE IV-continued

Experimental design to test if increasing pH prevents LAMP inhibition by

LAMP Assay Sample Descriptions

| Sample Type | E. coli 25922 DNA (ng) | DNA Volume (µL) | chitosan (g/L) | pH | DDnase Water (µL) | 0.1M Phosphate Buffer (µL) | 1M NaOH adjustment | Total Sample Volume (µL) |
|---|---|---|---|---|---|---|---|---|
| C | 0.2 | 1 | 0.01 | 10 | 0 | 4 | yes | 5 |
| D | 0.2 | 1 | 0.1 | 10 | 0 | 4 | yes | 5 |

Statistical Analysis

The performance of the electroflotation system is evaluated by effects on LAMP detection rates (0-100%) from samples subjected to various EF treatments in comparison to control samples without EF treatment. Differences in detection rates based on positive detection in LAMP assays were evaluated using two-way ANOVA. Dunnett's multiple comparisons post-hoc analysis was used to identify experimental treatment conditions that were different than corresponding controls. Statistical differences in the detection rates from each fraction collected were evaluated using two-way ANOVA and post-hoc Tukey's multiple comparisons test. Detection rate data evaluating the initial EF system performance was normalized using a log transformation, however the data presented in figures is not transformed.

To evaluate the effects (i.e. inhibition) of adding Pluronic and chitosan to a LAMP assay, differences in threshold times were evaluated by linear regression or two-way ANOVA and Dunnett's or Tukey's post-hoc analysis for multiple comparisons.

To quantify the effect of adding Pluronic to EF treatments changes in LAMP detection rates from EF treatments+ Pluronic samples were compared to corresponding control samples from EF treatments without Pluronic. The effect of chitosan was evaluated the same way except the control sample contained the 0.1 g $L^{-1}$ pluronic.

"Reliable detection" was deemed to be positive identification of copies of template DNA or bacterial cells in at least 95% of assays at the tested condition. Positive detection was classified for threshold times values $t_T$<28 minutes. Averaged threshold times exclude tr values ($t_T$>31 minutes). Significance was imputed for p-values less than 0.05.

The results of the experiments are now described.

Corrosion Inhibiting Coatings

Silver Filled Conductive Epoxy

Scanning Electron Microscopy

Figure 15A:
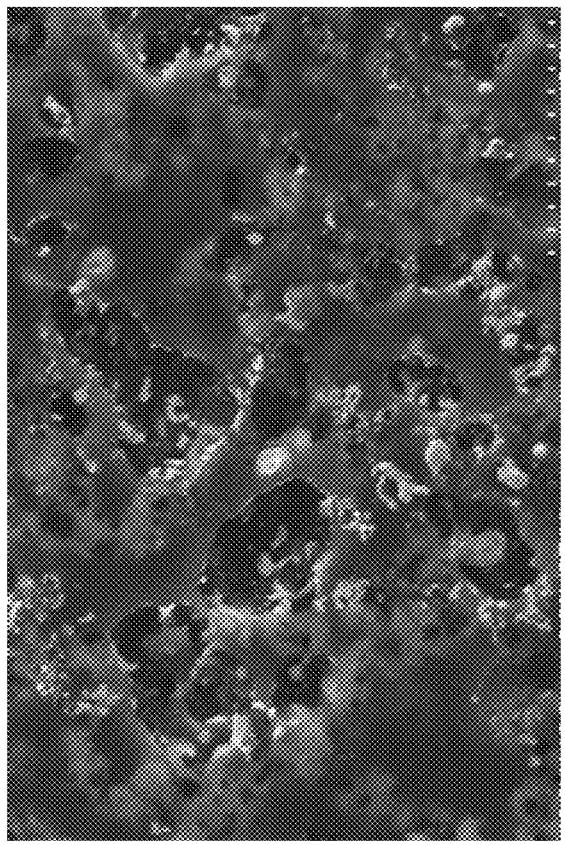

The silver epoxy, imaged by SEM prior to oxidation, shows an intact and smooth matrix (FIG. 15A). After oxidation (FIG. 15B), formation of holes and bubbles through the material was observed indicating the epoxy matrix had considerable changes in the physical morphology of the material.

Energy Dispersive X-Ray Spectroscopy (EDS)

Figure 16B:
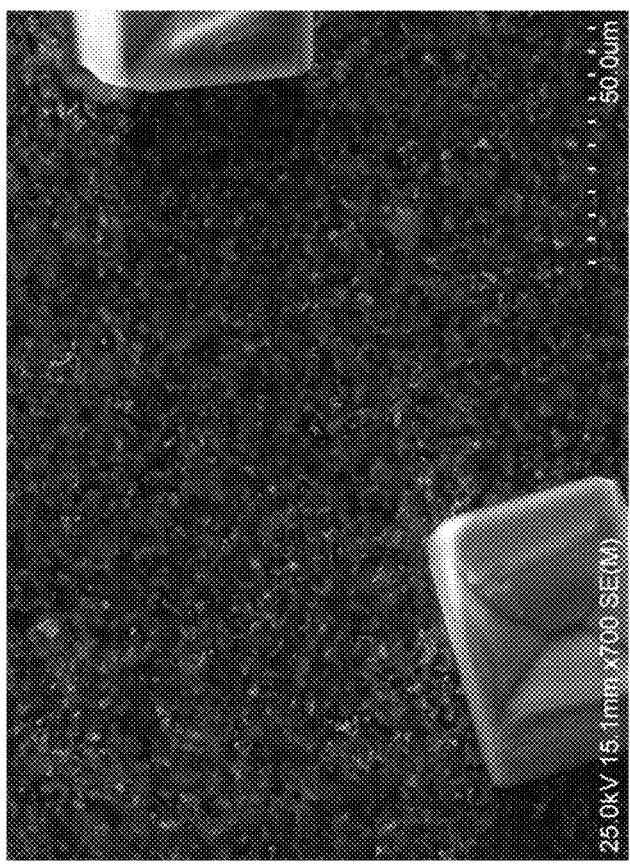
FIG. 16A and FIG. 16B depict overlaid energy dispersive X-ray spectroscopy (EDS)+scanning electron microscopy (SEM) images of silver epoxy after oxidation.
Figure 16A:
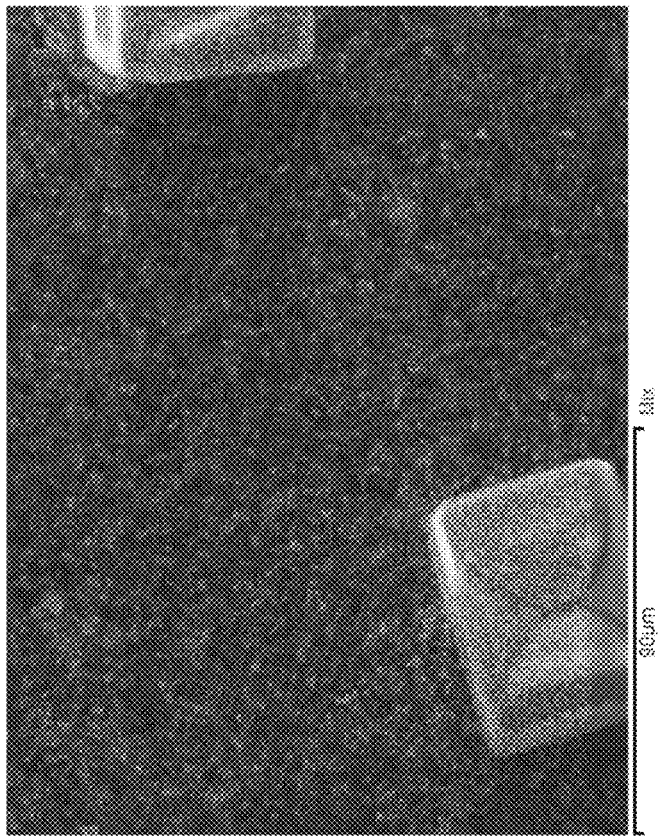
Figure 17B:
FIG. 17A and FIG. 17B depict overlaid EDS+SEM images of silver epoxy after reduction.
Figure 17A:
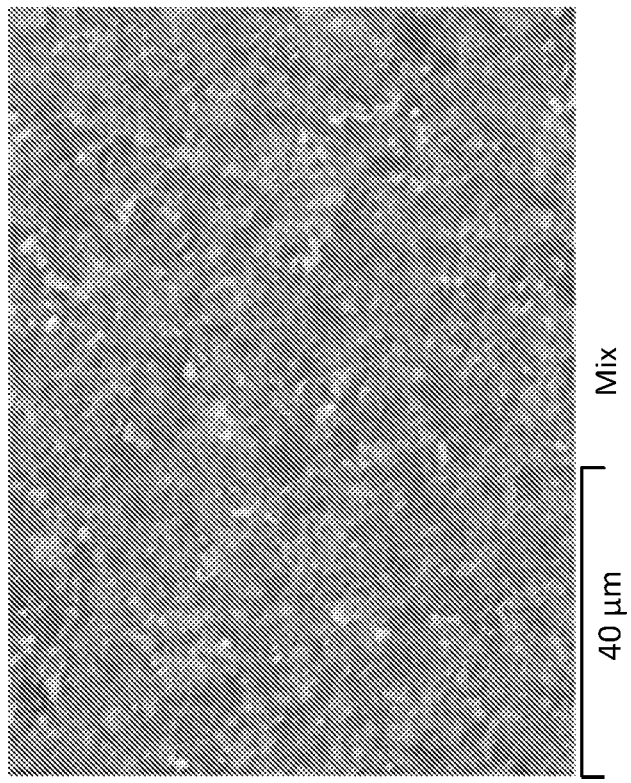
Figure 18:
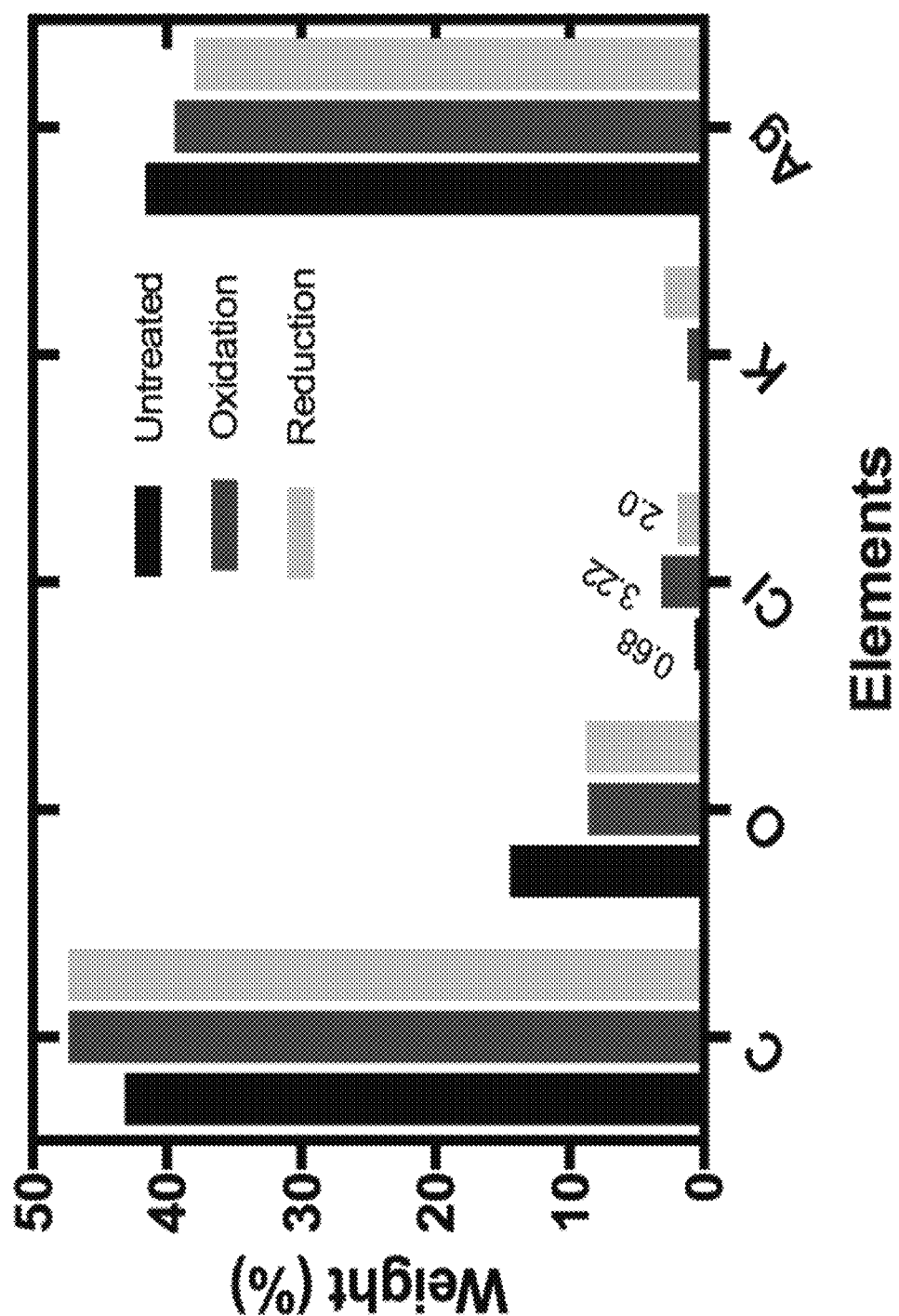
FIG. 18 is a graph depicting EDS percent weight (wt %) results of Silver Epoxy.

The EDS results (FIG. 16A through FIG. 18) confirmed that composition (% wt) of chlorine atoms on the untreated epoxy surface (Cl=0.68% wt) changed after oxidation (Cl=3.22 wt %) (FIG. 16A, FIG. 16B) and reduction (Cl=2.0% wt) (FIG. 17A, FIG. 17B). Percent weight (% wt) (FIG. 18) is calculated as the relative concentration of the element at the surface of the sample i.e. silver epoxy in the viewing window of the SEM. At least some chloride present in the EDS analysis after reduction is likely residual salt from the saturated KCl (4.56 M) solution (FIG. 16A). Although silver epoxy enabled hydrogen evolution at lower electrochemical potentials, and could be reversibly reduced, current (I) could not be sustained for long durations of time due to rapid chloridation and oxidation of the anodic surface. The rapid drop in surface conductivity of silver as it is oxidized to a coating of silver chloride paste renders silver epoxy as a poor choice for supporting intense anodic reactions for electrolysis.

Carbon Conductive Paste

Figure 19A:
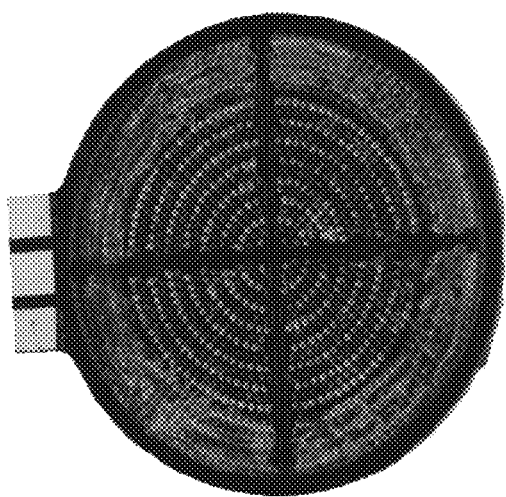
FIG. 19A and FIG. 19B depict an image of a carbon conductive paste (CCP) coated electrode array subjected to electroflotation (EF) and recorded current (mA).
Figure 19B:
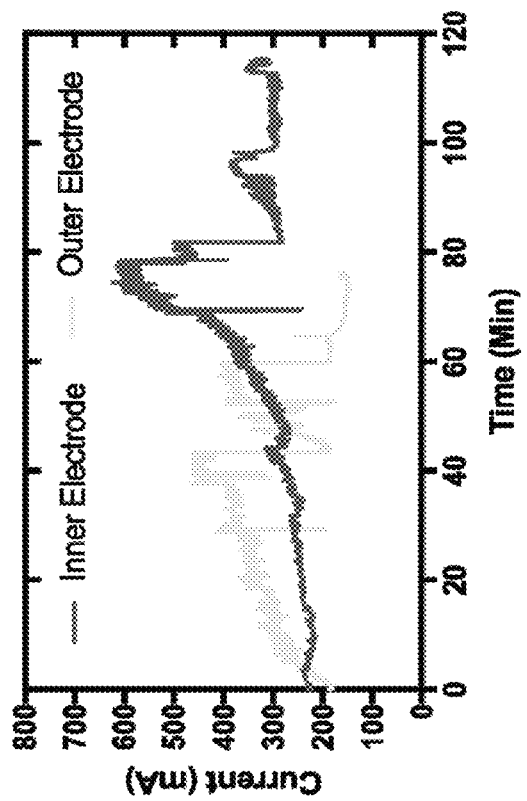

PCB electrode arrays coated with CCP supported relatively stable current densities (1.5-14.2 $mA/mm^2$) at an applied constant voltage (4.21 V) over 120 minutes. Visible evidence of long-term corrosion of the underlying metal was present on some, but not all, of the anodic surfaces of the electrode array (FIG. 19A). In (FIG. 19B), there is evidence that after ~75 minutes and 40 minutes for the inner and outer array respectively, the current sharply decreased. This suggests that for a short duration, e.g. for use in a disposable electrode array, CCP can adequately protect the underlying metal. However, without improved application and adhesion to underlying metal CCP may not be suitable for imparting long-term stability necessary for reusable electrode arrays.

Conductive Silicone

Figure 21B:
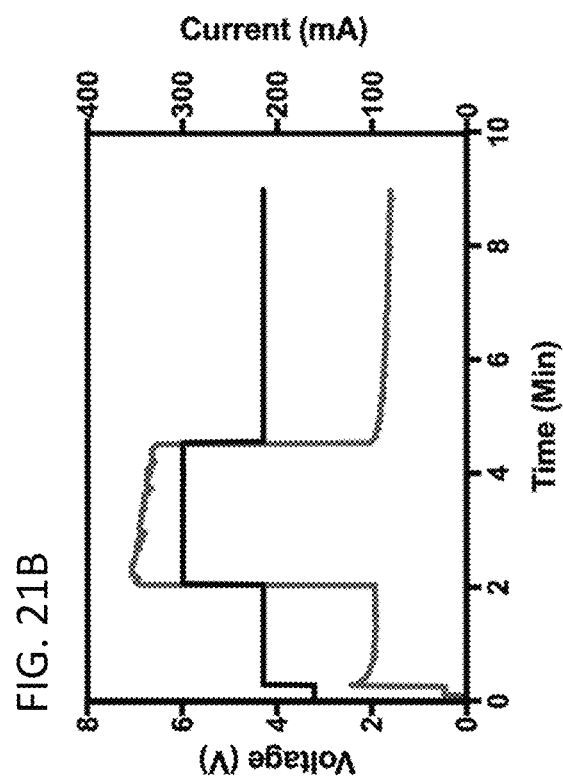
FIG. 21A and FIG. 21B depict PDMS (with and without surface modification) current (mA) at different applied voltages.
Figure 21A:
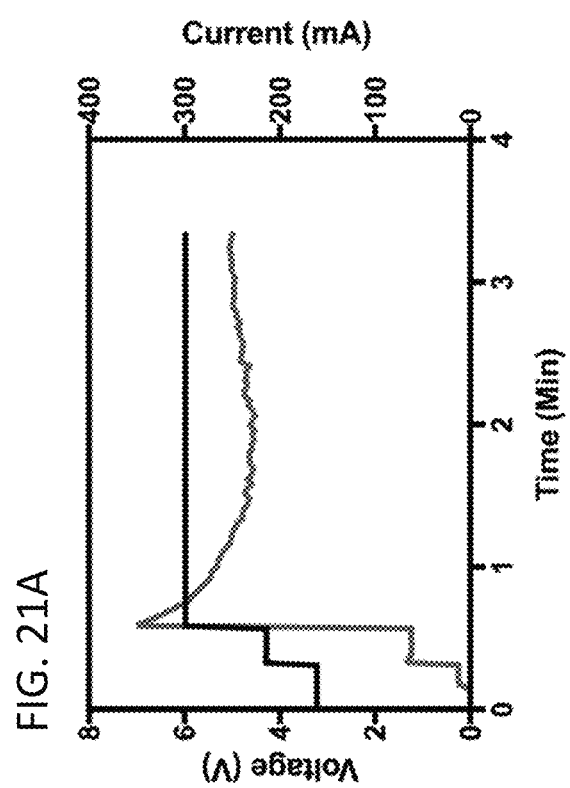

Modifying the surface of PDMS by oxygen plasma treatment followed by physio-absorption of PEG changed the surface from hydrophobic to hydrophilic. Prior to surface modification and during EF treatments, a layer of large bubbles covered the surface of the electrode arrays (FIG. 20A). After PDMS surface modification, the bubbles formed during electrolysis were visually smaller, quickly coalescing and releasing from the electrode substrate (FIG. 20B). Without $O_2$+PEG surface modification (FIG. 20A), at a voltage of 6 V, was initially about 330 mA but within minutes dropped to around 250 mA (FIG. 21A). For the same voltage (6 V) PCB electrodes with 02+PEG surface modification (FIG. 20B) sustained a stable current at 325-350 mA (FIG. 21B).

As previously mentioned, during constant current or constant voltage electrolysis, the wettability (hydrophobic/hydrophilic properties) of the surface of an electrode will affect how long a bubble resides on the electrode. When a bubble resides on the surface of the electrode, especially when the diameter is large, the ohmic resistance to current across the electrode/electrolyte interface increases (Bouazaze, H. et al., 2006, J. Electroanal. Chem. 597:60-68). FIG. 21A and FIG. 21B depicts peaks or noise that can likely be attributed to changes in electrolyte resistance as bubbles grow and detach. If the 1st peak is considered at 6 V for both before (FIG. 21A) and after (FIG. 21B) surface modification as the initial incremental resistance to current ($R_0$), it is not surprising that in both scenarios the current decreases from the initial peak as the electrolyte resistance increases for the same constant voltage. Although the surface modification was effective, the modified PDMS was not stable over multiple preliminary trials and unable to generate reproducible data and significant differences were observed between different electrodes. Furthermore, the flux and quantity of bubbles produced was much lower than achieved in the final electrode design.

Platinum Coated Titanium Electrodes

Figure 22:
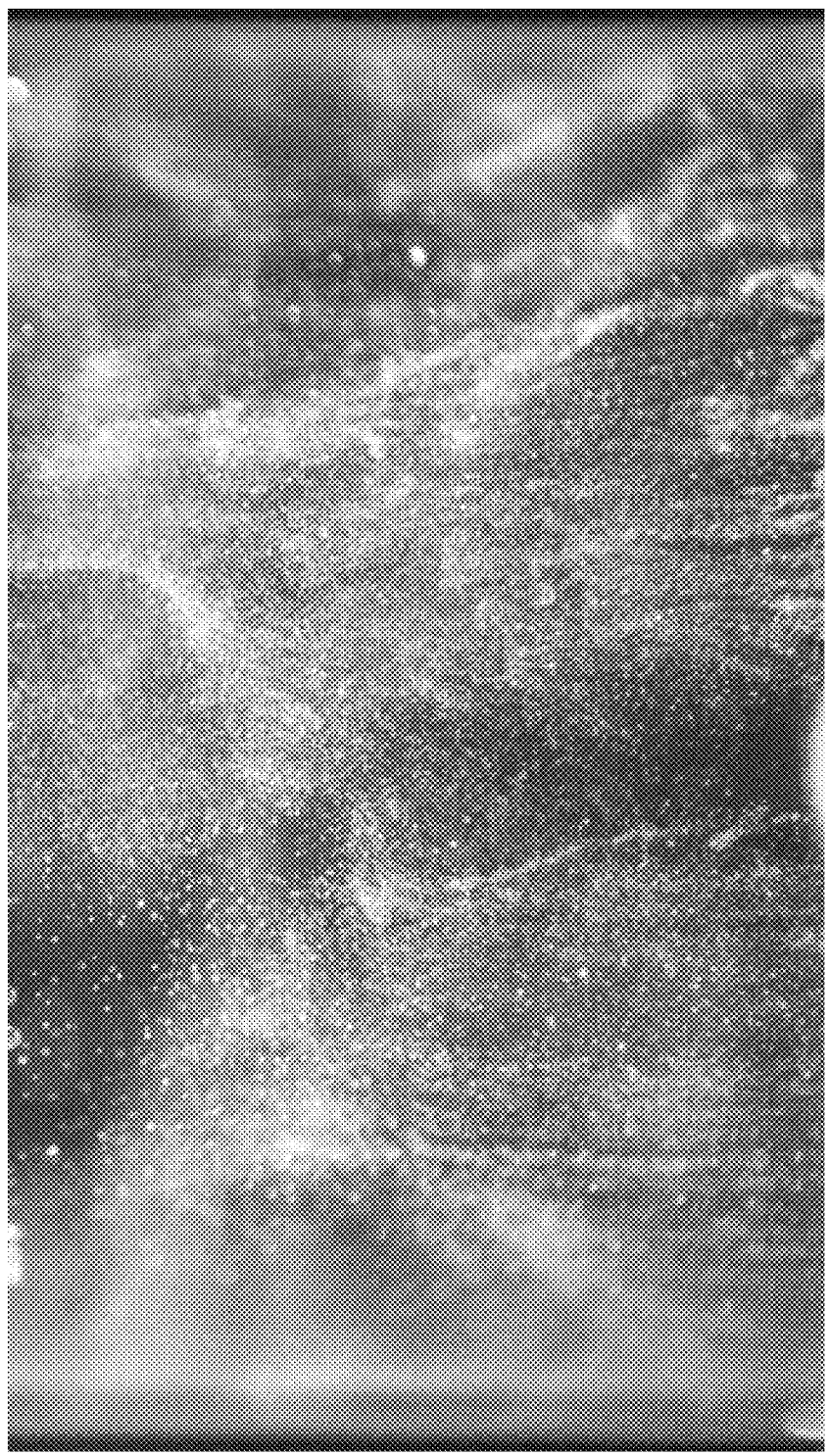
FIG. 22 depicts microbubbles produced by TiPt electrodes during EF.

TiPt electrode arrays were tested in HT and LT flotation conditions (n=3 for each condition). The microbubbles produced during electrolysis (FIG. 22) were uniformly distributed and the flux was noticeably sensitive to changes in current.

Figure 23A:
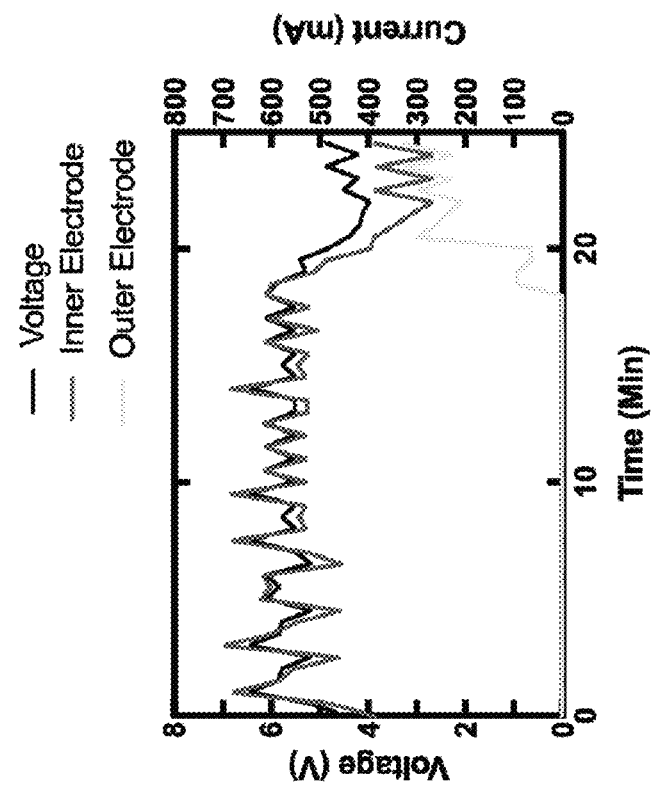
FIG. 23A and FIG. 23B depicts current/voltage readings of TiPt electrodes during EF.
Figure 23B:
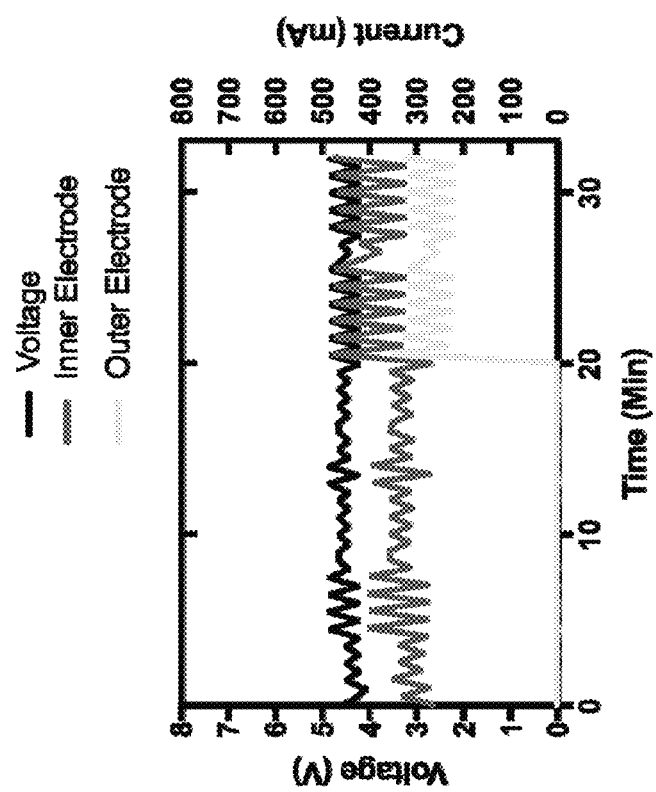

For example, LT conditions generated a columnar pillar of upwardly rising bubbles without mixing. For HT flotation conditions, a larger current was constantly applied, and significantly more bubbles were produced. Using the current control feature, for both HT (FIG. 23A) and LT (FIG. 23B) conditions, a constant current of 300 mA and 600 mA respectively was applied for 20 minutes. The current was regulated in software by adjusting the applied voltage up or down based on "errors" the measured current value relative to the desired value. Limitations in the resolution of the custom implemented adjustable regulator resulted in oscillations in applied voltage and current around the set-point current (FIG. 23A, FIG. 23B), though these oscillations did not produce noticeable oscillations in the bubble flux or bubble behavior. No signs of corrosion were observed during the initial 3 experimental replicates for each condition. The electrodes have run EF treatments over 100 times subsequent to the preliminary experiments reported here, and have reproduced stable electrochemical readings over time without any apparent signs of corrosion.

Lamp Assay

Evaluation of Modified LAMP Primer Set

Figure 24:
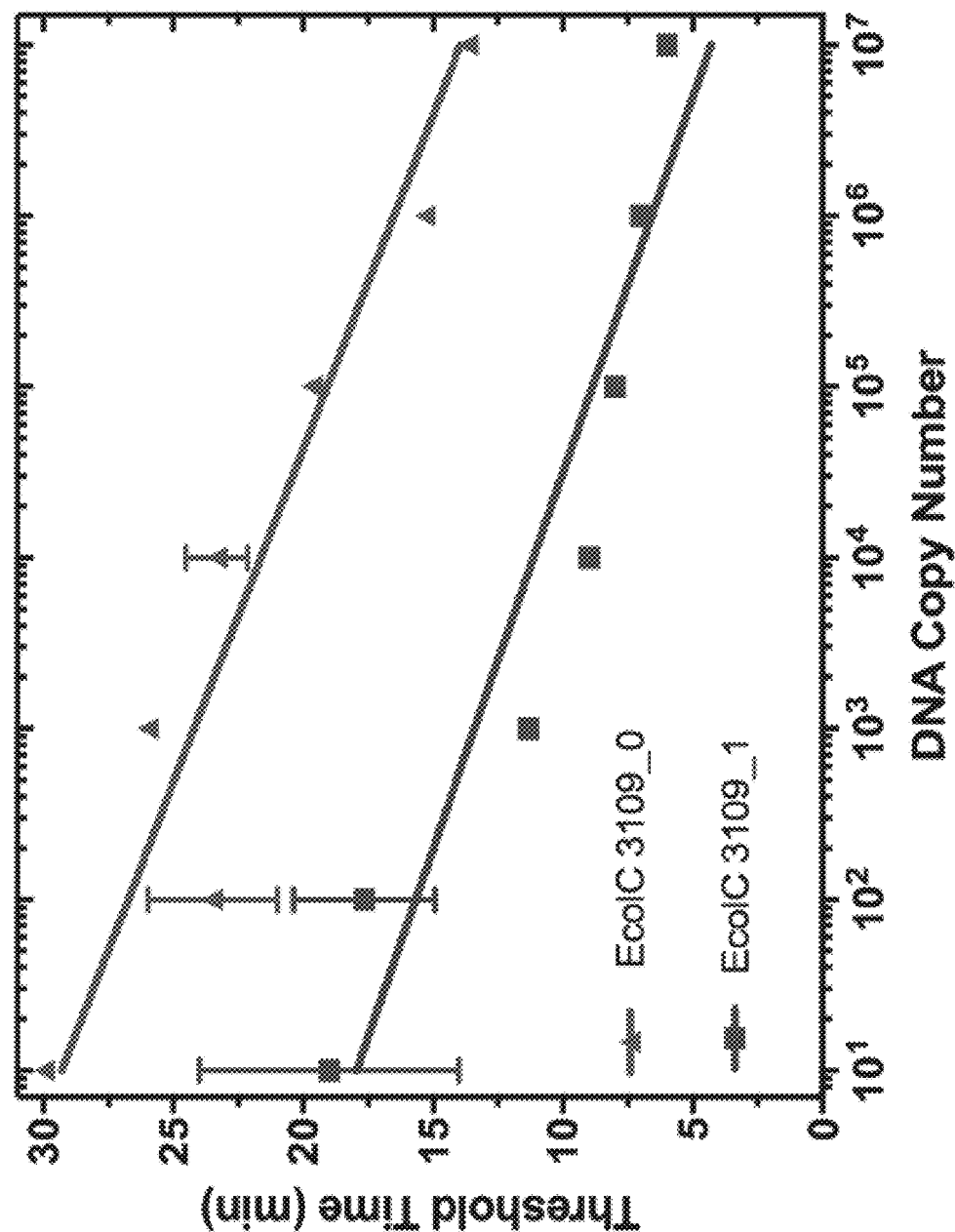
FIG. 24 is a graph depicting the performance of original versus modified EcolC 3109 LAMP primers. Quantitative comparison of observed threshold times for original primer set EcolC 3109_0 and modified primer set EcolC 3109_1 using purified *E. coli* 25922 DNA.

The modified primer set EcoIC 3109_1 was quantitatively compared to the original primer EcoIC 3109_0 with purified E. coli DNA over a range of DNA concentrations equivalent to $10^1$ to $10^7$ copy numbers per reaction (FIG. 24). Applying a semi-logarithmic regression to the quantitative comparison model, significant differences between y-intercept values were observed (P<0.001) between the primer sets, with EcoIC 3109_1 ($y_{int}$=20.24) reactions consistently amplifying sooner than those with the EcoIC 3109_0 ($y_{int}$=31.88) primer set. The detection limit for EcoIC 3109_0 was $10^2$ DNA copies, while EcoIC 3109_1 was able to detect DNA present at $10^1$ copy numbers at $t_T$=18 minutes. These results confirm that modifications to the previously published LAMP assay (Teh, C. S. J. et al., 2014, Sci. World J. 2014) resulted in improved detection limits and more robust amplification.

Specificity of Modified EcoIC 3109_1 Primer Set

In silico analysis supported specificity of the modified primer set (EcoIC 3109_1) towards generic E coli. Primer set 3109_1 was 100% identical to 25 E. coli sequences including E. coli ATCC 29522 while the remaining 33 E. coli sequences evaluated shared ≥95% match identify between the glycerate kinase gene region and 3109_1 primer binding regions. Primer set 3109_1 showed little to no specificity towards non-E. coli strains with a mean query coverage of 15+/−21.7%. A list of E. coli strains and non-E. coli strains with % match identity % query coverage respectively can be found in Table V.

TABLE V

Specificity tests of modified LAMP primer to non-E. coli strains. in silico results with respective query coverage (%) to primer set EcoIC 3109_1. Query coverage is calculated by considering the percentage of the input sequence (query ie. Primer sequences) overlapping the entire genome of the non-E. coli strains retrieved from the NCBI database.

| Strains | Source | LAMP in silico | Query cover % |
|---|---|---|---|
| Acinetobacter baumannii | ATCC 19606 | — | 0 |
| Aeromonas hydrophila | ATCC 7966 | — | 56 |
| Aeromonas caviae | ATCC 15468 | — | 8-15 |
| Bacillus cereus | ATCC 10876 | — | 0 |
| Burkholderia cepacia | ATCC 25416 | — | 40 |
| Campylobacter jejuni | ATCC 33560 | — | 0 |
| Citrobacter freundii | ATCC 8090 | — | 6-7 |
| Enterobacter aerogenes | ATCC 13048 | — | 53 |
| Enterobacter cloacae | ATCC 13047 | — | 0 |
| Enterococcus faecalis | ATCC 19433 | — | 0 |
| Enterococcus faecium | ATCC 19434 | — | 0 |
| Klebsiella oxytoca | ATCC 13182 | — | 60 |
| Klebsiella pneumoniae | ATCC 25955 | — | 0 |
| Lactobacillus acidophilus | ATCC 4796 | — | 0 |
| Listeria monocytogenes | Scott A | — | 0 |
| Micrococcus luteus | ATCC 4698 | — | 0 |
| Proteus mirabilis | ATCC 29906 | — | 0 |
| Proteus vulgaris | ATCC 29905 | — | 28 |
| Pseudomonas aeruginosa | ATCC 14886 | — | 0 |
| Salmonella enterica | | — | 56 |
| Serratia marcescens | ATCC 13880 | — | 6-7 |
| Shigella sonnei | | — | 34 |
| Staphylococcus aureus | ATCC 51811 | — | 0 |
| Staphylococcus aureus | ATCC BAA-39 | — | 0 |
| Streptococcus pyogenes | ATCC 10782 | — | 7 |
| Yersinia enterocolitica | | — | 13-43 |

LAMP Performance for Detection of E. coli w/Out EF Treatment

Figure 25:
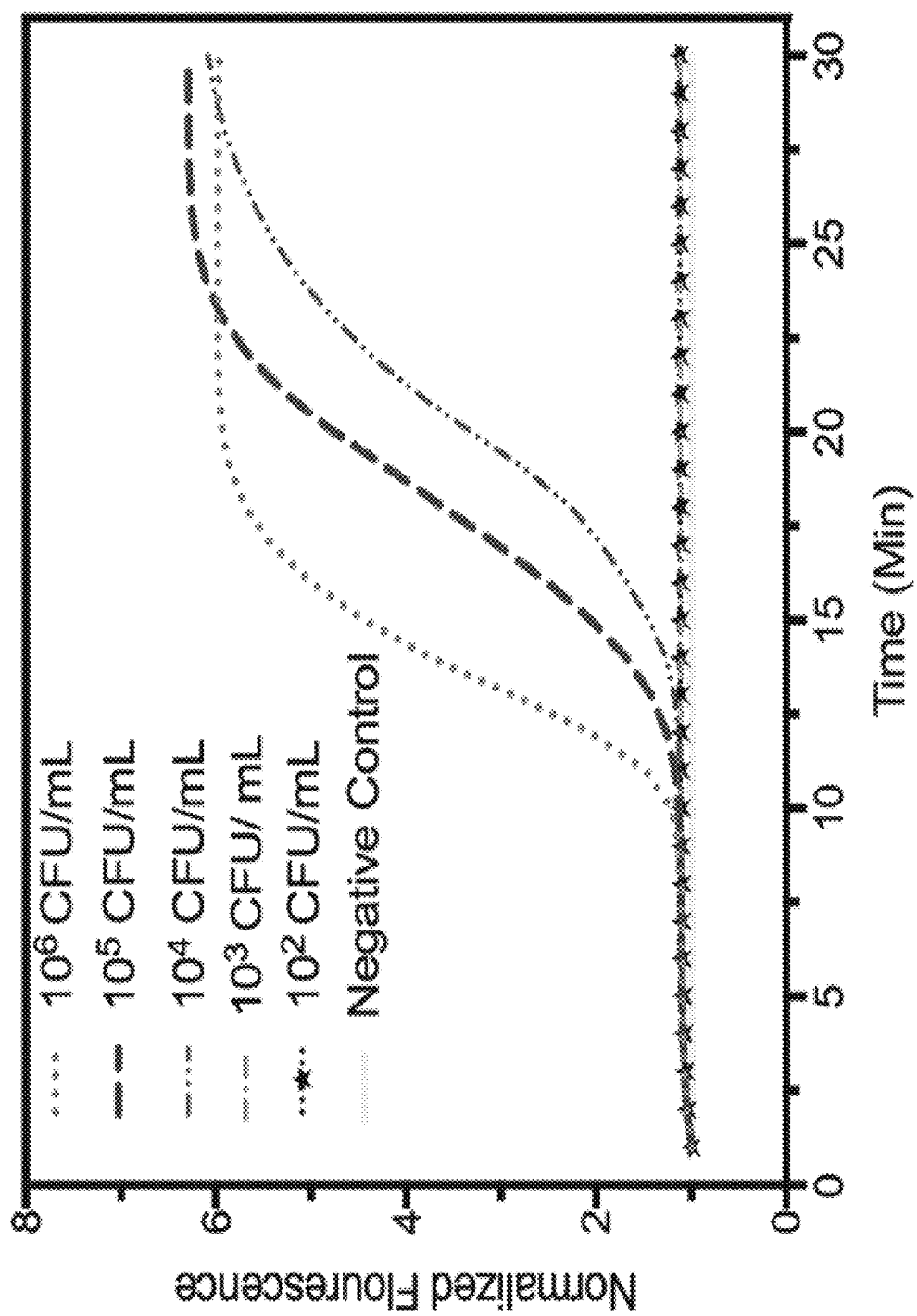
FIG. 25 is a graph depicting representative LAMP curves at varying untreated *E. coli* 25922 concentrations ($10^2$-$10^6$ CFU/mL). The lowest detectable concentration in these untreated controls was $10^4$ CFU/ml, though $10^5$ CFU/mL is required for reliable detection.

Representative amplification curves for control reactions using primer set EcoIC 3109_1 with untreated cell suspensions are shown in FIG. 25. The detection limit, where at least 95% of samples could be reliably detected, was observed to be about $10^5$ CFU/mL, as 100% of samples at this concentration resulted in amplification, but only 48% of samples at $10^4$ CFU/mL resulted in amplification. Mean threshold times observed in the positive $10^4$ CFU/mL samples was 16.58+/−3.43 minutes. Although EcolC 3109_1 detected purified *E. coli* DNA in quantities reliably at concentration as low as $10^2$ DNA copy number, the detection limit was higher (equivalent to 500 CFU or genome copies) in samples where only crude lysis was used to expose genomic DNA. No positive detection was observed in a total of 54 assays of untreated samples at either concentration of $10^2$ or $10^3$ CFU/mL. The baseline performance of the assay on crude cell lysates assay (FIG. 25) identified detection limitations and all subsequent electroflotation experiments were conducted with sample concentrations≤detection threshold limit=$10^5$ CFU/mL ranging from $10^2$-$10^4$ CFU/mL.

Electroflotation Treatment (EF)
Evaluation of EF Treatment Effects on Detection Limits of *E. coli*

Figure 26A:
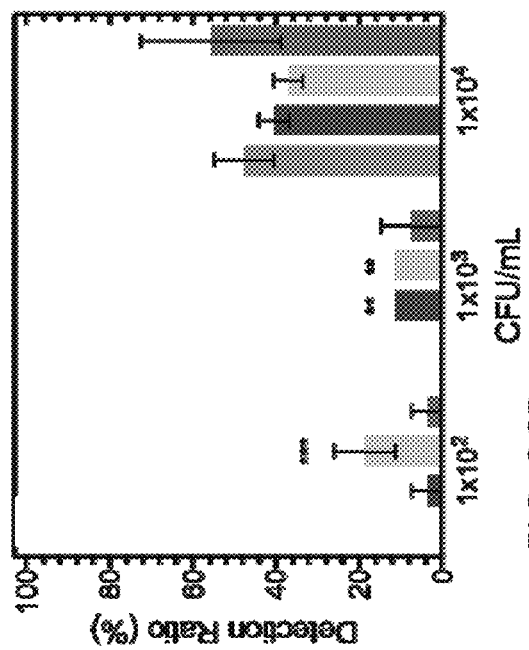
FIG. 26A through FIG. 26D are graphs depicting sensitivity of LAMP assays after high (FIG. 26B) and low turbulence (FIG. 26D) electroflotation treatments. In (FIG. 26A; high turbulence) and (FIG. 26C; low turbulence) each data point represents the detection ratio from 27 assays conducted on samples from one replicated electroflotation treatment (n=3 for each treatment). Treatments significantly different than controls are designated with asterisks (*p<0.05,  p<0.01, * p<0.001) Error bars are standard errors of the means.
Figure 26B:
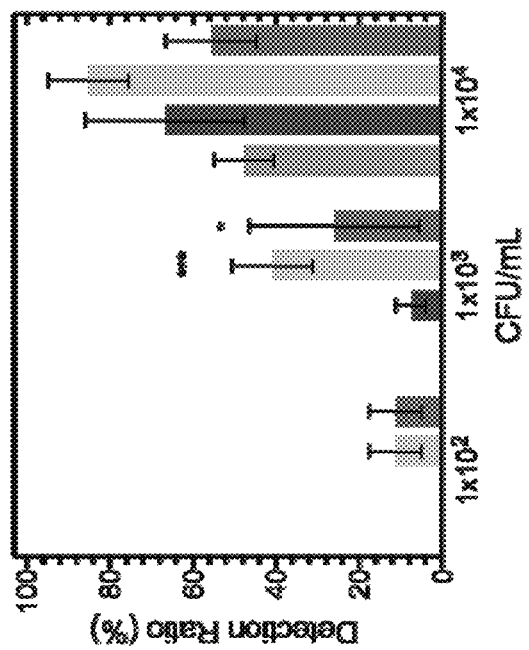
Figure 26C:
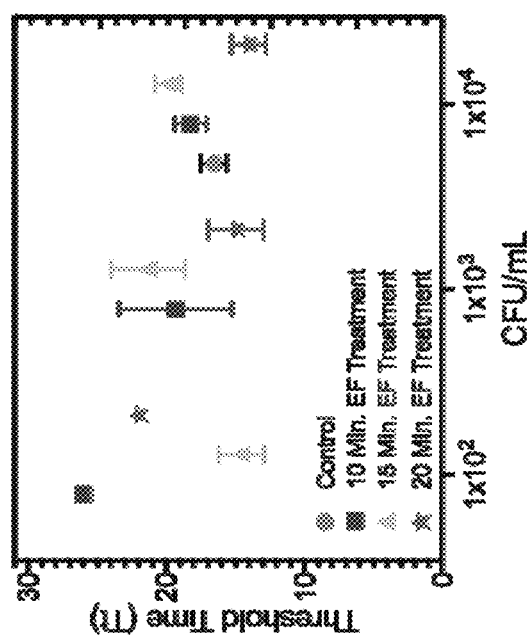
Figure 26D:
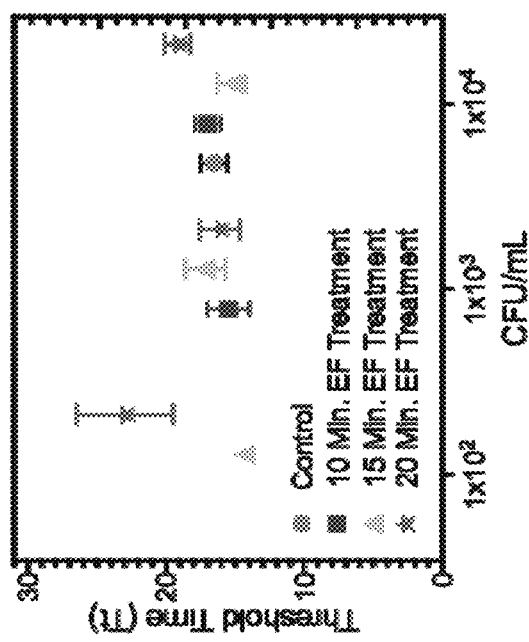

Samples were inoculated with varying concentrations of *E. coli* 25922 and subjected to various EF treatment conditions. Significant effects of EF treatments on detection rates of LAMP were observed for both high turbulence (FIG. 26A) (P=0.0019) and low turbulence conditions (P=0.002) (FIG. 26C) at the low concentrations tested ($10^3$ and $10^2$ CFU/mL). Using Dunnett's multiple comparison post-hoc analysis, 5 sets of experimental conditions at concentrations below $10^4$ CFU/mL were observed to have significant differences in detection rates after EF treatment when compared to the corresponding controls. For high turbulence conditions, significant differences were observed for $10^2$ CFU/mL at 15 minutes, $10^3$ CFU/mL at 10 minutes, and $10^3$ CFU/mL at 15 minutes of EF treatment with a mean detection rates of 18.57% (P=0.009), 11.11% (P=0.0031), 11.11% (P=0.0031) respectively (FIG. 26B). For low turbulence treatments in samples containing $10^3$ CFU/mL, significant differences were seen in 15 minutes (P=0.0007) and 20 minutes (P=0.0371) of EF treatment with mean detection rates of 40.73% and 25.92% respectively (FIG. 26D). Low turbulence conditions had overall higher detection rates for both $10^3$ and $10^4$ CFU/mL samples for both 15- and 20-minutes EF treatment when compared to their high turbulence counterparts. Although not considered significant, 100% detection was achieved in 1 experimental replicate for both 10 and 15 minutes for $10^4$ CFU/mL under low turbulence conditions. Similarly, over 50% detection rates were achieved for some 2 experiments at $10^3$ CFU/mL. Although detection rates did improve for conditions previously described, reliable detection requires 95% detection of positive samples.

Figure 27A:
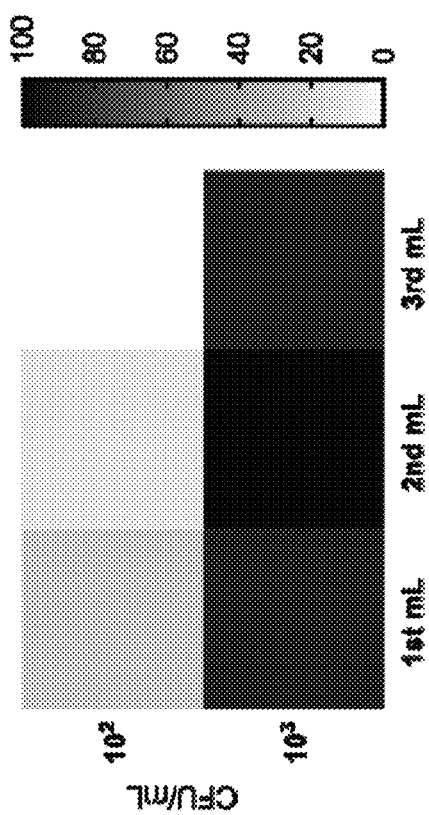
FIG. 27A and FIG. 27B depict heat maps of positive LAMP assays partitioned in collected fractions. The distribution of LAMP assays positively detecting *E. coli* 29522 in each recovered 1 mL fraction is shown. Each square shows the mean detection rate of 9 LAMP assays testing recovered fractions containing 0.01 g L-1 Pluronic (FIG. 27A) and 0.1 g L-1 Pluronic (FIG. 27B) treated with low-turbulence electroflotation conditions.
Figure 27B:
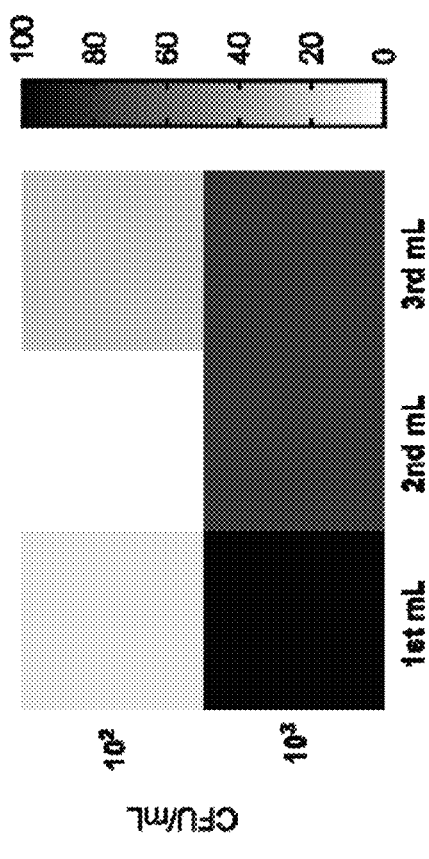
Figure 28A:
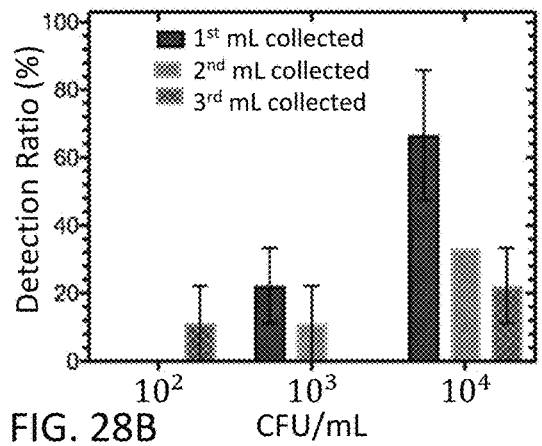
FIG. 28A through FIG. 28F depicts distribution of positive LAMP assay detection in individual collected fractions. 3 LAMP assays were performed for each 1st, 2nd, and 3rd mL sample fractions collected following high turbulence conditions for 10 (FIG. 28A), 15 (FIG. 28B), and 20 (FIG. 28C) minute EF treatment and low turbulence conditions for 10 (FIG. 28D), 15 (FIG. 28E), and 20 (FIG. 28F) minute EF treatment. Detection ratios are percentages of positive detection out of 3 assays for each recovered fraction. Each EF treatment for each bacterial concentration ($10^2$-$10^4$ CFU/mL) was repeated 3 times. Error bars are standard errors of the means.
Figure 28B:
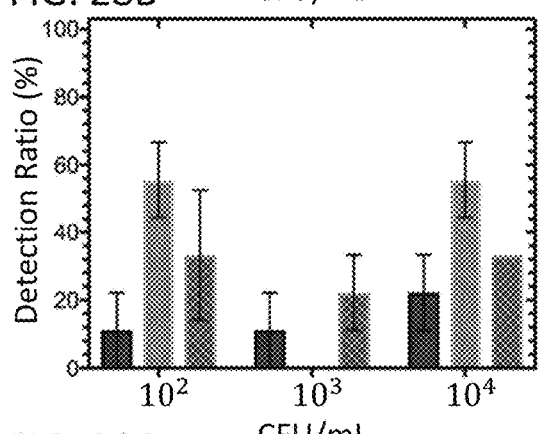
Figure 28C:
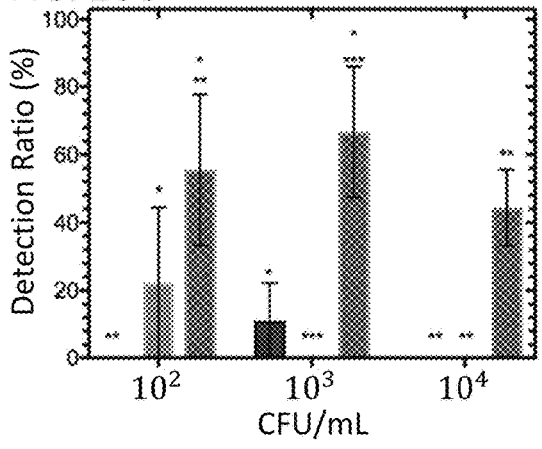
Figure 28D:
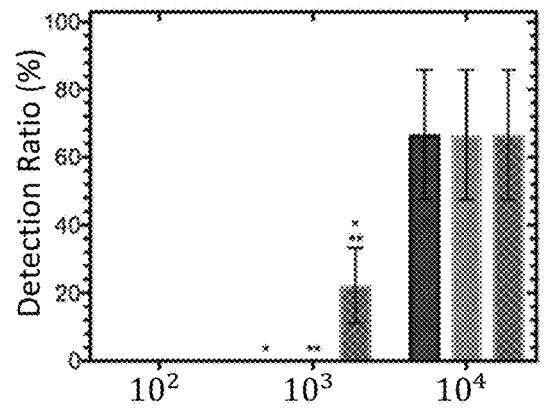
Figure 28E:
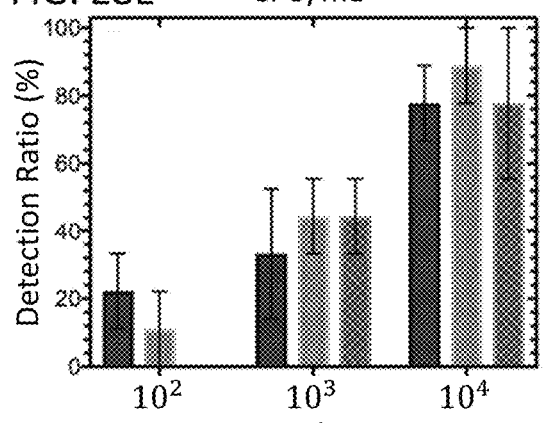
Figure 28F:
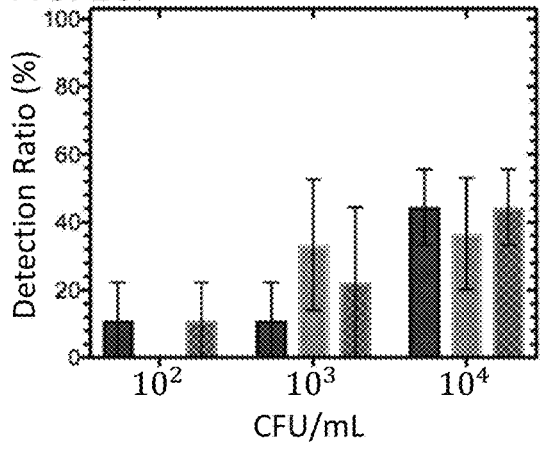

To identify the density gradient of *E. coli* in the recovered fraction distribution of positive LAMP assays for each 1 mL aliquot was analyzed separately. Samples containing 0.01 g $L^{-1}$ pluronic and $10^3$ CFU/mL (FIG. 27A) contained quantifiably higher concentrations of DNA in the 1st mL. In contrast samples containing 0.1 g $L^{-1}$ (FIG. 27B) pluronic yielded more positive LAMP assays in the 2nd mL than the 1st mL. For samples containing $10^2$ CFU/mL *E. coli* there was an even more variable distribution pattern of quantifiable DNA as these samples were below the detection limit of the LAMP assay. The fractions collected for samples containing $10^3$ CFU/mL did contain higher concentrations of DNA (by one order of magnitude) when compared to corresponding controls however the results were inconsistent and there was as much recovered in the third fraction as the first. While there is a definite density gradient established by the flotation process, turbulent mixing of the effluent likely prevents all the particulates from concentrating at the very top of the electroflotation chamber column.

Detection Rate Distribution Between Collected Fractions

The distribution of *E. coli* detection in each 1 mL fraction collected after EF treatment was analyzed by conducting 3 LAMP assays/1 mL fraction to determine the degree of stratification of *E. coli* in the top fractions of the media, and to observe which treatments were most effective at concentrating bacteria near the surface (FIG. 28A through FIG. 28F). Significant differences were observed (P<0.0001) in detection rates between fractions 1, 2 and 3 only for high turbulence treated samples at 20 minutes (FIG. 28C) while low turbulence treated samples showed no overall difference in detection rates between fractions. EF conditions that resulted in highly variable detection rates between fractions 1, 2 and 3, did not correspond, or share overlap with, the conditions where increased or improved detection rates with EF treatments were observed. Generally, low turbulence conditions had more even distribution of detection rates between fractions 1, 2 and 3 for all concentrations (CFU/mL) and varying durations (10, 15, 20 minutes) of EF treatment when no chemical additives were added to the buffer to promote flocculation or to mask the hydrophobicity of cell surfaces.

Pluronic F-68 Inhibition on LAMP

Figure 29:
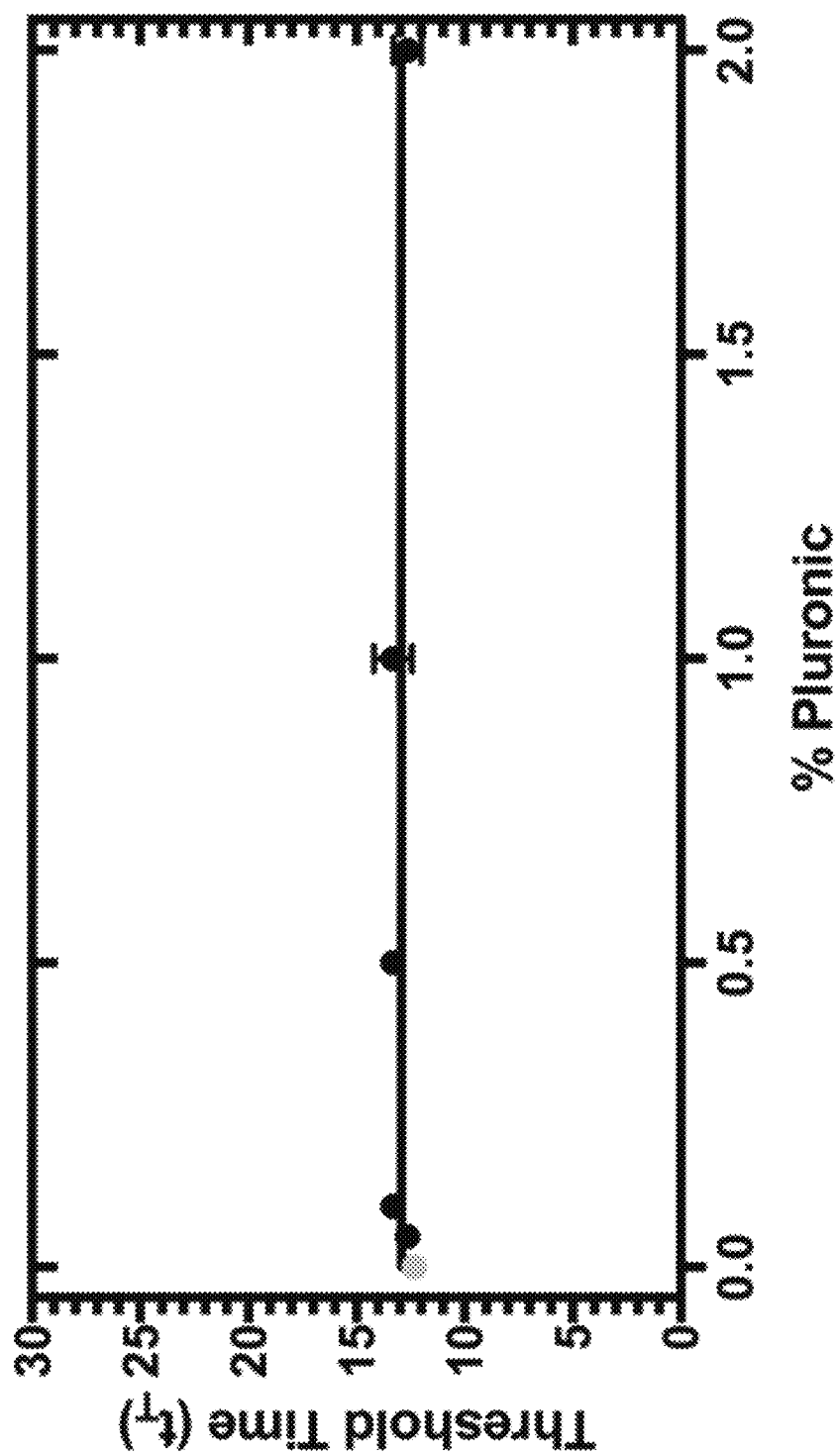
FIG. 29 depicts the results of inhibition on LAMP assays by Pluronic. Observed LAMP threshold times for samples containing varying concentrations of Pluronic (0.0%, 0.05%, 0.1%, 0.5%, 1.0%, 2.0%). Control group (0% Pluronic) indicated by green dot. Each data point represents 3 replicates at each condition. Error bars are standard errors of the mean.

LAMP assays were not inhibited by the addition of Pluronic to samples at all tested concentrations (0.05%, 0.1%, 0.5%, 1.0%, and 2.0%) (FIG. 29). Inhibition on LAMP, characterized by increased threshold times, was evaluated by linear regression. The linear regression between threshold time and Pluronic concentration (Y=0.01735*X+12.93) had a slope that was not statistically different than showed zero, (p=0.9542) indicating no observable effect of Pluronic concentration.

Chitosan Inhibition on LAMP

Figure 30:
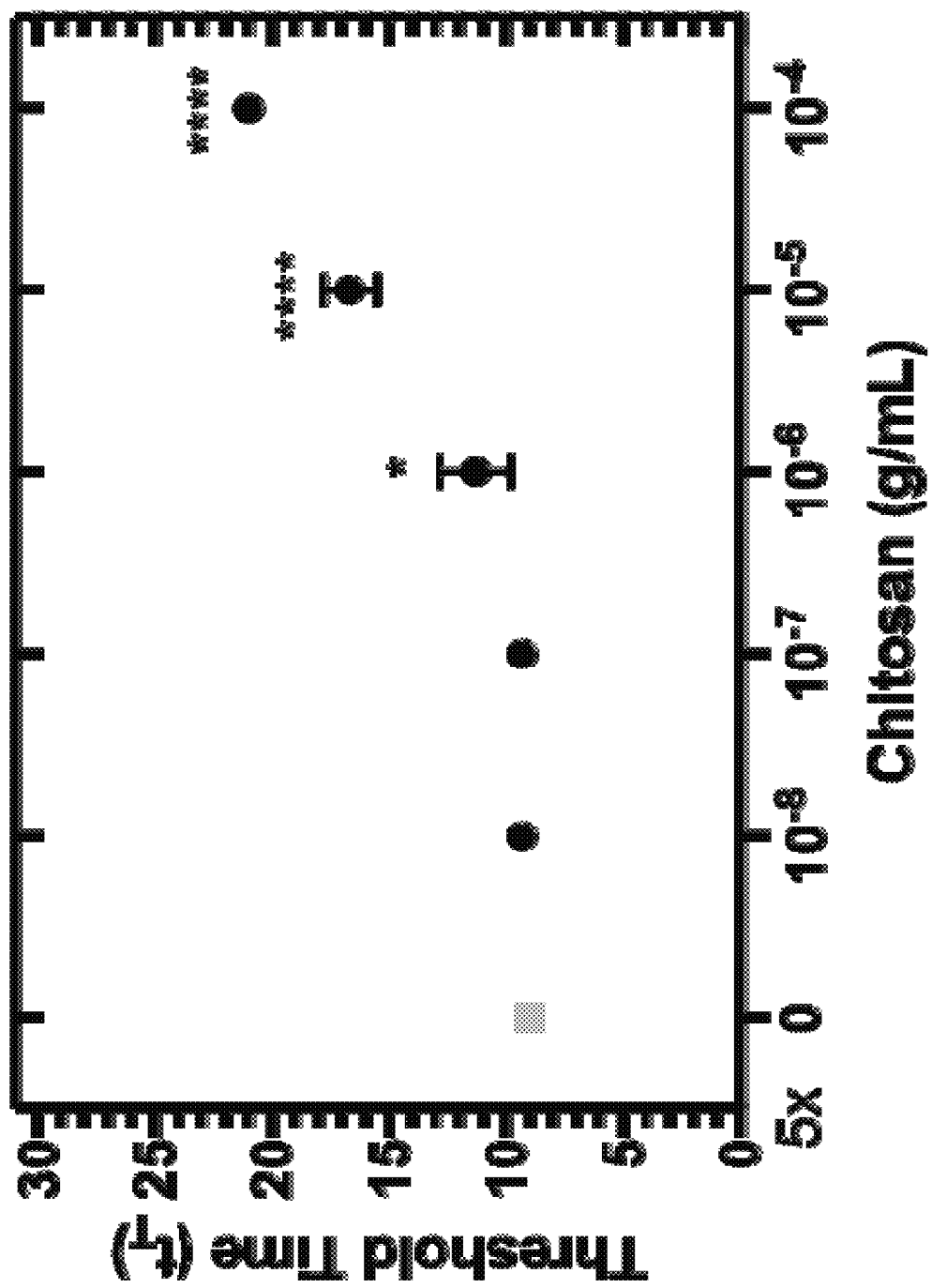
FIG. 30 depicts the results of inhibition on LAMP assays by chitosan. Observed LAMP threshold times for EF samples containing varying concentrations of chitosan (0, $5 \times 10^{-8}$, $5 \times 10^{-7}$, $5 \times 10^{-6}$, $5 \times 10^{-5}$, $5 \times 10^{-4}$, $5 \times 10^{-3}$ g L$^{-1}$). Chitosan completely inhibited LAMP at concentration >$10^{-3}$ g L$^{-1}$ (data not shown). Each data point represents the mean threshold time (tr) from (n=3) LAMP assays. Treatments significantly different than control (0 g L$^{-1}$ chitosan, green dot) are indicated by asterisk (*p<0.05, **** p<0.0001) Error bars are standard errors of the mean.

The effects of chitosan in a LAMP assay reaction were evaluated. Significant effects on threshold times (tr) of varying chitosan concentrations were observed (p=0.0001). Complete inhibition of LAMP occurred from samples containing chitosan concentrations above $5\times10^{-4}$ g $mL^{-1}$. This resulted in and no detection of *E. coli* 25922 by LAMP under these conditions. Using Dunnett's multiple comparison post-hoc analysis, 5 chitosan concentrations were observed to have significant effects on LAMP when compared to a corresponding control assay containing no chitosan ($t_T$=9 min., n=3). For chitosan concentrations above $10^{-7}$ g $L^{-1}$ significant differences in mean threshold times were observed for $10^{-6}$ g $mL^{-1}$, $10^{-5}$ g $mL^{-1}$, $10^{-4}$ g $mL^{-1}$ with mean threshold times of 11.33 (p=0.04), 16.67 (p=0.0001) and 21 (p=0.0001) respectively (FIG. 30).

Preventing LAMP Inhibition by Chitosan

The amino group of chitosan is cationic below its pKa (~pH 9.5). In this state, it will bind through electrostatic interaction to negatively charged negatively charged bacterial cells i.e. *E. coli* and also anionic DNA. Chitosan binding to anionic DNA can also prevent LAMP primer binding and inhibit amplification. At pH 6 chitosan present in concentrations of 0.01 and 0.1 g $L^{-1}$ inhibited amplification of 0.2 ng of *E. coli* 25922. LAMP was not inhibited, however, for the same concentrations of chitosan (0.01, 0.1 g $L^{-1}$) at pH 10 (FIG. 31C). Although PCR reactions can be completely inhibited at pH>9.0, LAMP assays with a sample pH 10 without chitosan, were only slightly inhibited and still robust enough to be able to amplify template DNA. The time to detection was longer by 3 minutes when comparing threshold times from the pH 10 chitosan (0.01, 0.1 g L−1) samples ($t_T$=15 min.), to control samples ($t_T$=12 min.). No difference in threshold time (tr) was observed between samples containing 0.01 or 0.1 g $L^{-1}$ chitosan. By adjusting the pH of the samples from pH 6 to pH 10, LAMP inhibition by chitosan was prevented and amplification of target was unaffected.

Chitosan present at concentrations above 1 g L$^{-1}$ in samples with a pH of 5.8 completely inhibited amplification of 0.2 ng of *E. coli* 25922. Samples containing 1 g L$^{-1}$ chitosan significantly (p=0.025) inhibited LAMP amplification increasing the time to detection by 6 minutes (t$_T$=15, @=9.24) compared to the control samples (t$_T$=9, 0=0) (FIG. 31A). Although samples containing 0.01 g L$^{-1}$ (p=0.998) and 0.1 g L$^{-1}$ (p=0.897) chitosan did not significantly inhibit LAMP reactions, slight inhibition was observed increasing the average time to detection from (t$_T$=9) to (t$_T$=9.6) and (t$_T$=11.33) respectively (FIG. 31A). Treatment with sodium hydroxide decreased the inhibition on LAMP amplification in samples containing lower concentrations of chitosan (0.01-0.1 g L$^{-1}$) and also in samples containing high concentrations of chitosan (1 g L$^{-1}$) so that amplification was normalized compared to control samples at the equivalent template DNA concentration (FIG. 31B). LAMP amplification was inhibited completely in samples containing chitosan in concentrations greater than 1 g L$^{-1}$ and sodium hydroxide was ineffective to improve amplification (FIG. 31B). Electroflotation treatments will non-specifically concentrate any particle ranging in size from 0.5 microns to 200 microns, including chitosan aggregates. Although the concentrations of chitosan used as a flocculant in this research (i.e. 0.01 and 0.1 g L$^{-1}$) were below levels causing complete inhibition it is important to note that the observed slight inhibition on LAMP will increase as the concentration of chitosan increases in the recovered samples.

Figure 32:
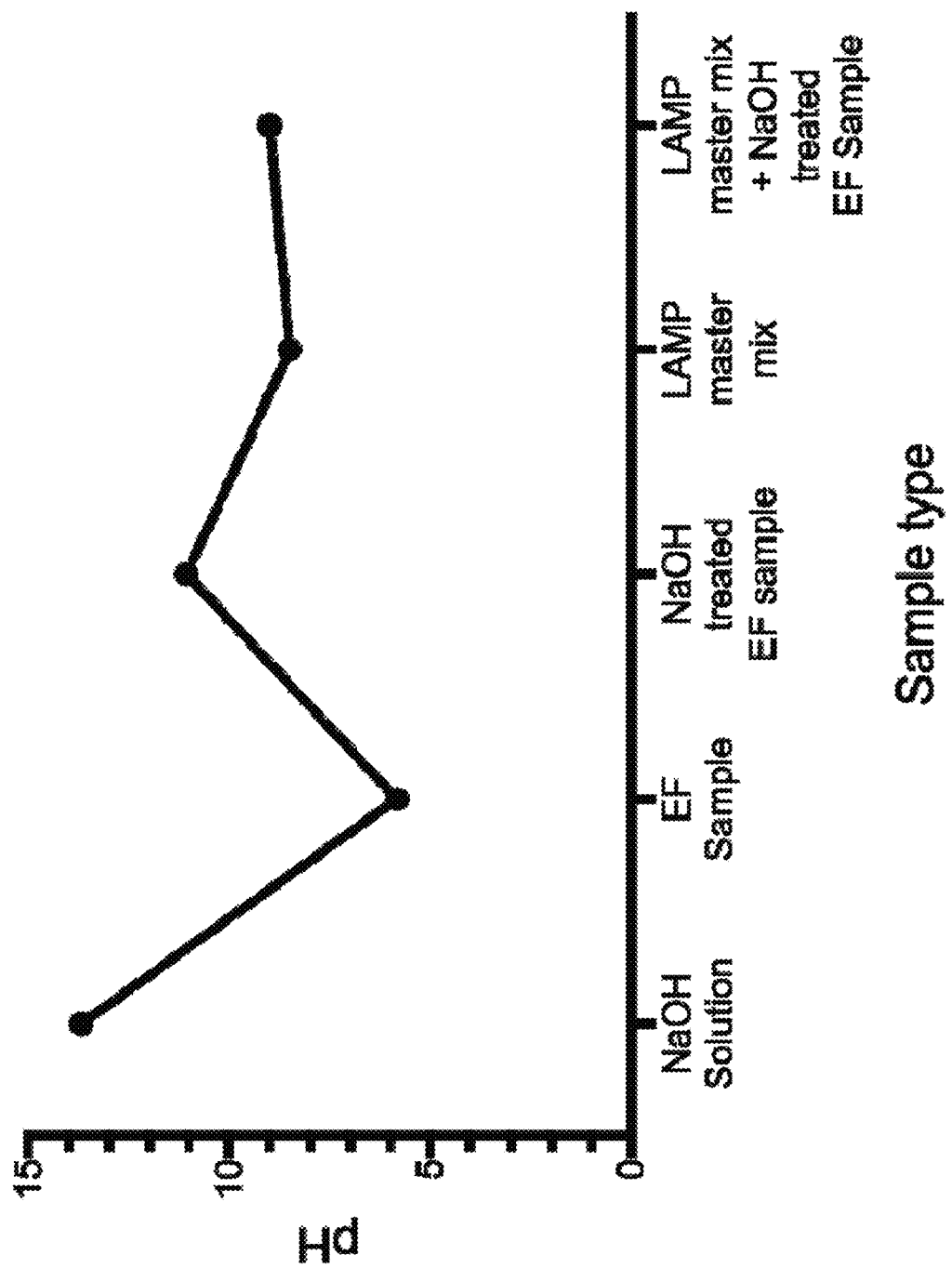
FIG. 32 depicts sample pH values. The pH was reported for each stage during sample preparation and LAMP assay.

In FIG. 32 it is shown that the pH of NaOH solution is approximately 13 and by adding the NaOH solution to the EF samples the pH value of the mixture was approximately 11. This value is well above chitosans pKa (~pH 9.5) and is effective to release the DNA for use in subsequent amplification. However, the pH value drops dramatically to 9 by mixing the NaOH treated sample with LAMP reaction buffer and no significant difference was observed between the LAMP reaction buffer with and without (pH=8.5) NaOH treated samples. This effect is due to the buffering capacity of the commercially available isothermal mastermix likely containing Tris-HCl or equivalent. The 5 μL of crude lysed and adjusted pH (pH 11) samples was pipetted from the supernatant after following sample preparation procedures described in section "Inhibitor removal". This procedure adequately removed enough chitosan to prevent inhibition in LAMP assays once the pH is normalized by the buffers contained in the reaction mix and below the pKa of chitosan.

EF Treatment+/−Pluronic F-68

To protect cells from lysis by hydrodynamic shear forces during EF treatments, varying concentration of Pluronic (0.001, 0.01, 0.1, 1.0 g L$^{-1}$) were added to EF samples. In preliminary experiments (data not shown) 0.001 g L$^{-1}$ Pluronic concentration was presumed too low to affect EF treatments and did not significantly change the detection rates by LAMP. At the same time, the addition of 1 g L$^{-1}$ Pluronic to EF treatments resulted in undesirable amounts of foam formation during electrolysis, leading to premature sample displacement and potential aerosolization of the target pathogen. Therefore, after preliminary screening of Pluronic concentrations, 0.1 and 0.01 g L$^{-1}$ were subsequently investigated.

Figure 33A:
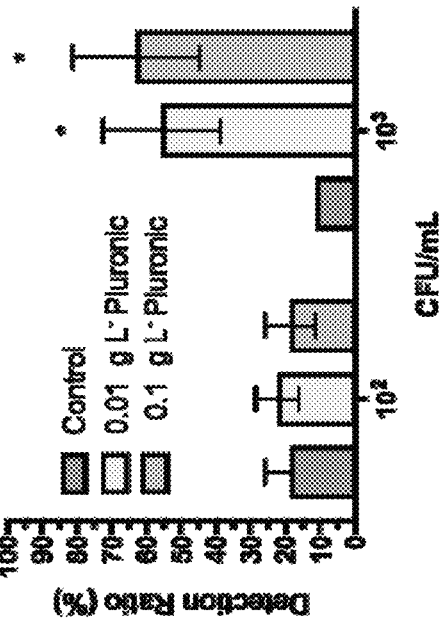
FIG. 33A through FIG. 33D depict sensitivity of LAMP assay with EF+/−Pluronic F-68 treated samples. LAMP threshold times after 15 min. HT (FIG. 33A) or 20 min LT (FIG. 33C) with the addition of 0.01 and 0.1 g L$^{-1}$ Pluronic to EF treatments. In (FIG. 33B) and (FIG. 33D), each bar represents the mean detection ratio from 27 assays conducted on samples from 3 replicated EF treatments. (9 assays/treatment, n=3 for each treatment). Treatments significantly different than controls are designated with asterisks (*p<0.05,  p<0.01, * p<0.001). In (FIG. 33B) and (FIG. 33D) Error bars are standard errors of the means. For (FIG. 33A) and (FIG. 33C), whiskers are from min to max and means are indicated by +. The box extends from the 25th to 75th percentiles.
Figure 33B:
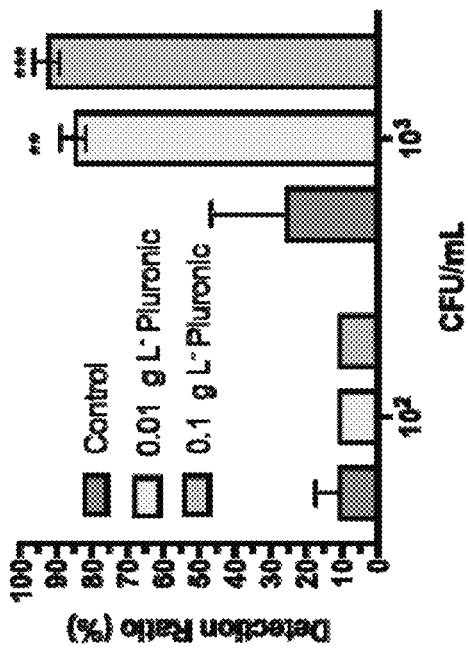
Figure 33C:
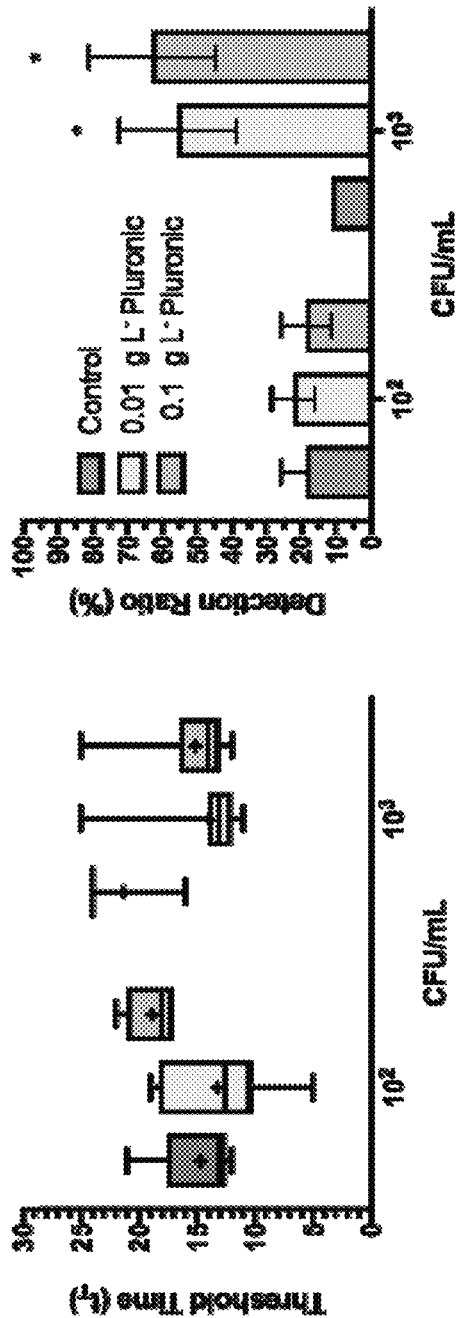
Figure 33D:
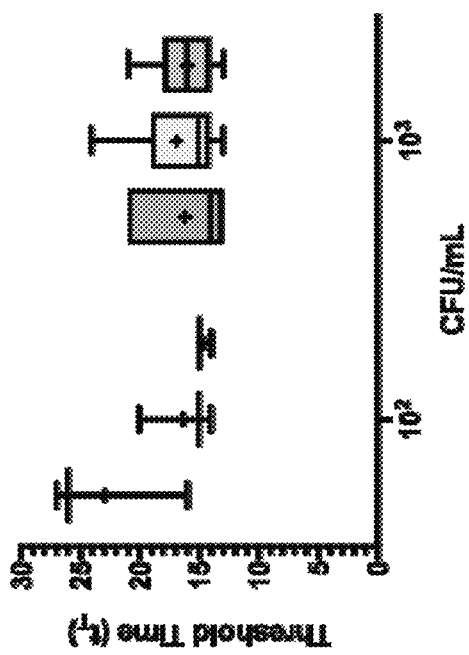

Using a 2-way ANOVA, no significant effects on LAMP detection rates were observed for 15-minute HT with the addition of Pluronic (0.01, 0.1 g L$^{-1}$) (FIG. 33B) when compared to control samples subjected to EF but without Pluronic. However, using Tukey's multiple comparison pot-hoc analysis, 2 experimental conditions were observed to have significant effects on LAMP detection rates after EF treatment when compared to corresponding controls (FIG. 33D). For 15-minute HT conditions, significant differences were observed for 10$^3$ CFU/mL at 0.01 g L$^{-1}$ (p=0.04) and 0.1 g L$^{-1}$ (p=0.019) with a mean detection rate of 55.55% and 62.96% respectively (FIG. 33B). In parallel, significant effects of EF treatments with the addition of Pluronic (0.01, 0.1 g L$^{-1}$) on LAMP detection rates were observed for 20-minute LT (p=0.0059) conditions at 10$^2$ and 10$^3$ CFU/mL tested concentrations (FIG. 33D). Using Tukey's multiple comparison post-hoc analysis, 2 experimental conditions were observed to have significant effects on LAMP detection rates after EF treatment when compared to corresponding controls. For 20-minute LT conditions, significant differences were observed for 10$^3$ CFU/mL at 0.01 g L$^{-1}$ (p=0.0016) and 0.1 g L$^{-1}$ (p=0.0006) with a mean detection rate of 85.18% and 92.59% respectively. No significant differences were observed between different Pluronic concentrations (0.01, 0.1 g L$^{-1}$) at either tested *E. coli* concentration (10$^2$, 10$^3$ CFU/mL).

Low turbulence conditions had overall greater increased detection rates by LAMP than compared to corresponding high turbulence conditions at 10$^2$ CFU/mL and 10$^3$ CFU/mL when media was supplemented with Pluronic. Furthermore, the addition 0.1 g L$^{-1}$ Pluronic resulted in greater increases in detection rates compared to the addition of 0.01 g L$^{-1}$ Pluronic for tested concentrations of 10$^3$ CFU/mL for both high and low turbulence conditions. LT turbulence conditions may be more desirable to stably recover aggregate flocs of bacteria by chitosan, therefore the concentration of Pluronic that performed the best under LT conditions (0.1 g L$^{-1}$) was chosen for subsequent EF treatments to test the effects of chitosan. In summary, reliable detection (>95%) was almost achieved (92.59%) for 20-minute LT EF treatments testing bacterial quantities of 10$^3$ CFU/mL with the addition of 0.1 g L$^{-1}$ Pluronic. While this is not quite the 95% detection rate required for low tolerance pathogens, this is significant improvement from the ~25% detection rates that were observed in corresponding controls without Pluronic. In subsequent experiments, to investigate the effects of chitosan, EF treatments were conducted only on samples containing 10$^2$ CFU/mL and 0.1 g L$^{-1}$ Pluronic at 20-minute LT EF conditions.

EF Treatment+/− (Chitosan+Pluronic)

Figure 34:
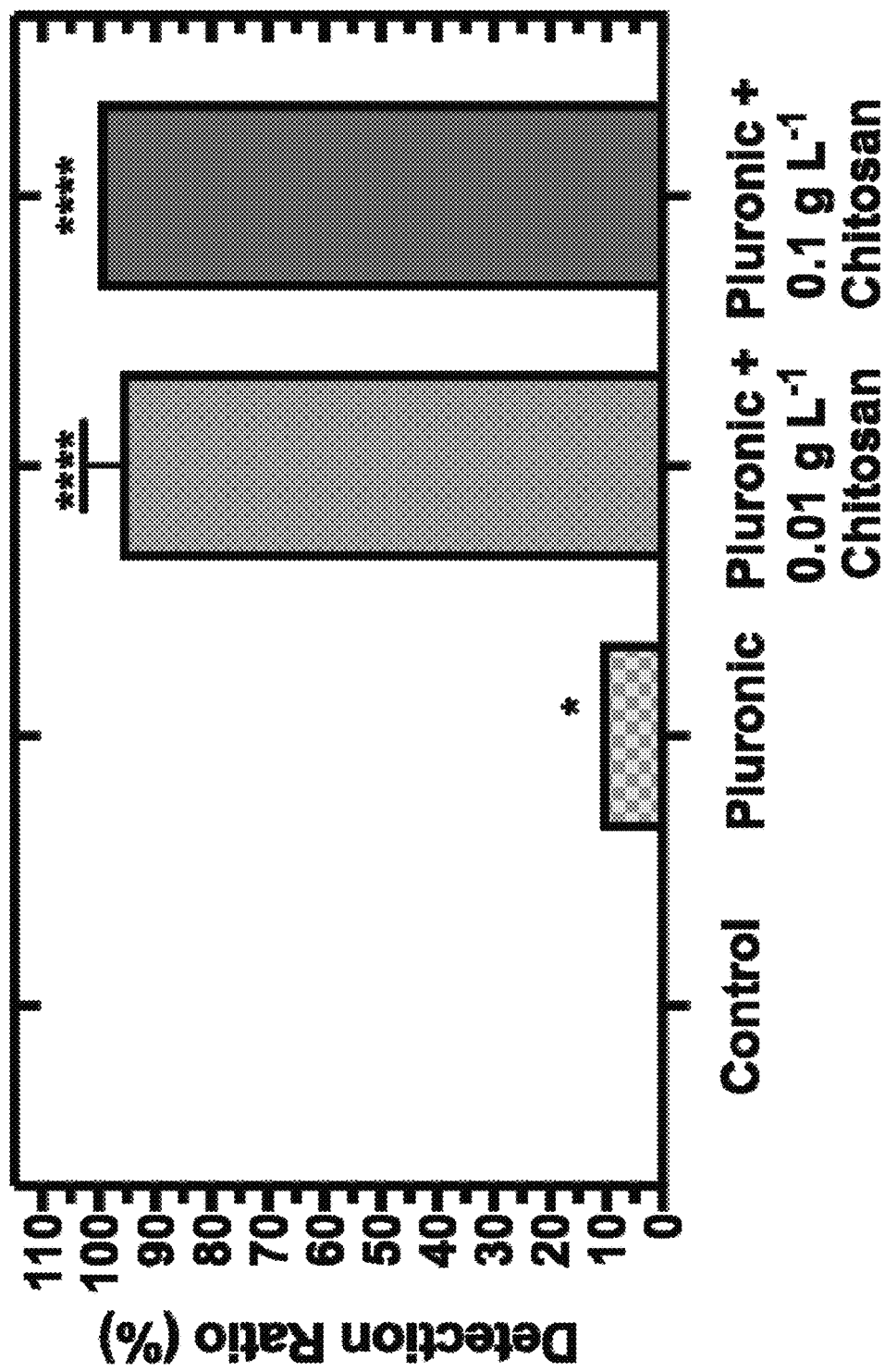
FIG. 34 depicts LAMP assay detection rate of EF+/− (chitosan+Pluronic F-68). $10^2$ CFU/mL, Low turbulence, 20-minute treatment with the additions of 0.1 g L$^{-1}$ Pluronic+0.01 g L$^{-1}$ chitosan. Control contained no Pluronic. Each bar represents the total detection rate from 9 assays testing only the 1st mL collected from 3 replicated EF treatments (3 assays/1 mL, n=3). Treatments significantly different than controls are designated with asterisk (*p<0.05, **** p<0.0001). Error bars are standard errors of the means.

LAMP was conducted on the first mL collected after 20-minute low turbulence EF treatments containing 10$^2$ CFU/mL bacterial quantities and 0.1 g L$^{-1}$ pluronic and 0.1 and 0.01 g L$^{-1}$ chitosan. Significant differences were observed for treatments containing chitosan (p=0.0001) when compared to corresponding controls (FIG. 34). Dunnett's multiple comparison post-hoc analysis identified 2 treatments that were significantly different from the EF treatments only containing pluronic and no chitosan. For 10$^2$ CFU/mL LT 20 min, when compared to corresponding treatments only containing pluronic, significant differences were observed for EF treatments containing 0.01 g L$^{-1}$ chitosan (p=<0.0001) and 0.1 g L$^{-1}$ chitosan (p=<0.0001) with mean detection rates of 96.3% and 100% respectively.

Figure 35:
FIG. 35 is an image of an exemplary electroflotation system. For testing the efficacy of electroflotation treatment for point-of-care sample preparation a self-contained battery powered EF device was designed to interface wirelessly with an Android app.

Sample acquisition, concentration and detection of bacterial contaminants was achieved in less than 2 hours without a specialized laboratory facility or traditional enrichment methods by a custom designed portable, automated electroflotation EF system (FIG. 35). The EF system was capable of concentrating hundreds of mL (380 mL) containing 10$^2$ CFU/mL *E. coli* into 1 mL containing approximately 10$^4$-10$^5$ CFU/mL. This technology is ideal to support and enhance sensitive detection of bacterial contaminants by portable molecular diagnostics especially in point-of-care testing. All processes presented in this research can be performed during field testing including DNA extraction (crude cell lysis) and removal of LAMP inhibitors. The degree to which the EF system was capable of concentrating bacteria dispersed in media was measured indirectly, by observing changes in detection rates of a LAMP assay. Identifying the limit of detection of the LAMP assay without EF treatment allowed inferring that if reliable detection was achieved, the EF system must concentrate the bacteria levels above this limit. The designed LAMP assay could detect dispersed *E. coli* present in quantities of $10^4$ CFU/mL and $10^5$ CFU/mL at a rate of ~50% and 100% respectively. Optimizing surfactant (Pluronic F-68) and flocculant (chitosan) concentrations eventually allowed reliable detection of bacterial quantities of $10^2$ CFU/mL at an average rate of 96.3%-100%. The EF system met the detection rate (~95%) required for testing high consequence pathogens at the tested levels, and detection limits may be improved more through scale up of the original sample, reduction in the recovered fraction volume, or for other assays with lower detection limits than the one used here for demonstration in this work (Kubota R. et al., 2015a, Int. J. Mol. Sci. 16:4786-99).

The proposed technology is novel, and addresses needs of federal agencies such the EPA, which has ongoing research initiatives aimed towards innovative approaches to separate bacteria, viruses and parasites from large volumes of water, up to 1600 liters. The EF system demonstrates potential to be adapted into current or new state or federal water, food, agriculture or aquaculture testing methodologies. There are ongoing collaborations with the Water Resources Research Center at the University of Hawai'i at Mānoa aimed to integrate these technologies to detect microbial communities in Honolulu's water supplies, to evaluate contamination risks and to aid resource management to make informed decisions during disasters like hurricanes, flooding, and sewage contamination (data not shown). Many pacific islands like Guam and Samoa face similar water quality challenges and would benefit from knowledge generated in Hawaii and this research. Portable biotechnology has broad applications in Hawai'i's growing aquaculture industry and sustainable farming infrastructure, especially in the context of expanded testing requirements under the Food Safety Modernization Act.

EF Treatment with Chitosan and Pluronic

Figure 36:
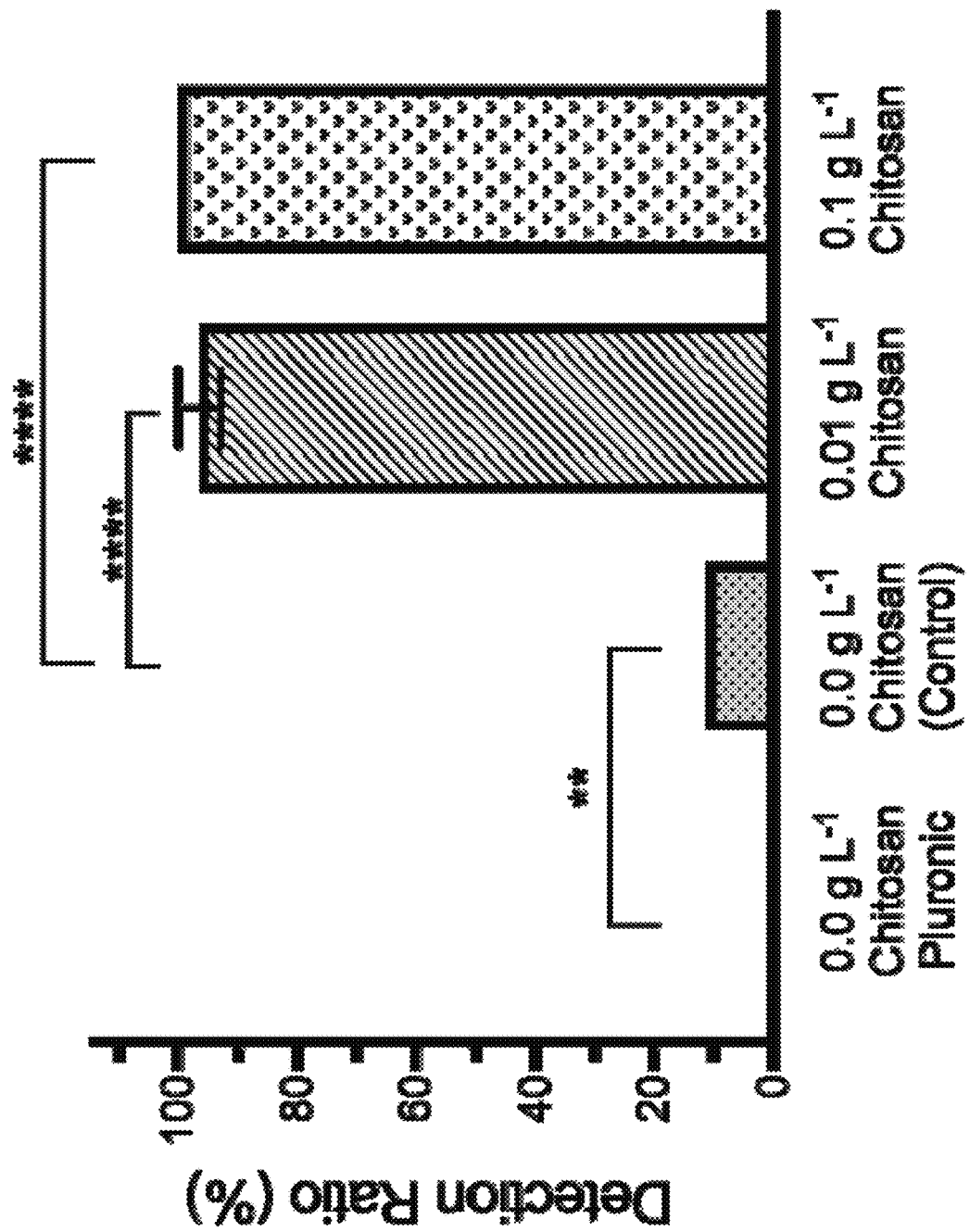
FIG. 36 depicts LAMP assay detection rate of EF treated samples with chitosan and Pluronic. $10^2$ CFU/mL, Low turbulence, 20-minute treatment with the additions of 0.1 g $L^{-1}$ Pluronic+0.01 g $L^{-1}$ chitosan. Control contained 0.1 g $L^{-1}$ Pluronic but no chitosan. Each bar represents the total detection rate from 9 assays testing only the 1 st mL collected from 3 replicated EF treatments (3 assays/1 mL, n=3). Treatments significantly different than controls are designated with asterisk (*p<0.01, **** p<0.0001). Error bars are standard errors of the means.

Following 20-minutes of low turbulence EF treatment of media with $10^2$ CFU/mL *E. coli* 25922 and 0.1 g $L^{-1}$ Pluronic, LAMP assays positively detected the bacteria with mean detection rates of 100% and 96.3% respectively in samples with 0.1 or 0.01 g $L^{-1}$ chitosan. Statistically significant differences (p=0.0001) in detection rates were observed for all treatments containing chitosan (0.1 or 0.01 g $L^{-1}$) when compared to corresponding controls (0.0 g $L^{-1}$ chitosan) (FIG. 36). Dunnett's multiple comparison a posteriori test confirmed both tested concentrations of chitosan (0.1 g $L^{-1}$; p=0.0001 and 0.01 g $L^{-1}$; p=0.0001) resulted in significantly different detection rates compared to EF treatments containing Pluronic but no chitosan.

Example 2: Electrolysis

The principle of electroflotation is fundamentally centered around electrolysis of water to evolve oxygen ($O_{2(g)}$) and hydrogen ($H_{2(g)}$) gas microbubbles, respectively generated by electron transfer at anodic and cathodic electrode surfaces. When an electric potential is applied to a set of electrodes in contact with an electrolytic solution, net positive current travels from the anode (positive) to the cathode (negative). If potential exceeds the redox potential difference for a paired set of half-reactions, such as evolution of oxygen at the anode and hydrogen gas at the cathode, those reactions can result in electron transfer across the electrode/electrolyte interface:

Anodic reaction $2H_2O_{(l)} \rightarrow 4e^- + 4H^+ + O_{2(g)}$      Eq. (3)

Cathodic reaction $4e^- + 4H^+ \rightarrow 2H_{2(g)}$      Eq. (4)

Overall reaction $2H_2O_{(l)} \rightarrow O_{2(g)} + 2H_{2(g)}$ $\Delta E° = -1.23$ V      Eq. (5)

The anodic reaction (4) especially is often different from that shown above. For example, sometimes a sacrificial material such as aluminum or iron is used for the anode to generate trivalent ions to enhance flocculation of electrically stabilized particles or colloids (Gregory, J. et al., 2011, Colloid Interface Sci. 169:1-12). Anodic reactions may also result in undesirable corrosion and passivation of metal anodes, or generation of reactive chlorine species from chloride ions in solution (such as used for electrolytic chlorination; Zhao Y. et al., 2017, J. Electrochem. Soc. 164: E138-E143). Electrolytic charge transfer through the media is facilitated by ionized salts such as potassium phosphate while the electrodes provide a physical interface between the buffer and electrical circuit driving current. Buffering salts such as phosphate also moderate bulk pH changes due to imbalances in the acid-base chemistries of the half-reactions, and local pH changes due around individual electrodes.

The realization of highly efficient water electrolysis depends on the interactions between process parameters including applied voltage (V), current (I), media pH and conductivity, spatial geometry and arrangement of electrodes, electrode material, surface wettability (Alam, R. et al., 2016, J. Water Process Eng. 12:78-88) and electrical resistivity (p). Electrical resistivity attributed to gas bubbles, activation energies, mass transfer, circuit resistance or electrode erosion can largely hinder electrolysis reactions (Santos, D. M. F. et al., 2013, Quim. Nova 36:1176-1193). The initiation and propagation of corrosion is a major concern during electrolysis and is an inextricably linked process between the previously mentioned parameters and environmental conditions. Electrode corrosion can result in physicochemical changes in the material composition and morphology, resulting in impaired ability to support redox charge transfer across the electrode/electrolyte interface. As a result, it is highly critical that electrodes be designed to be resistant to mechanical and chemical degradation (Santos, D. M. F. et al., 2013, Quim. Nova 36:1176-1193). The electrode material durability largely determines the reproducibility and efficacy of the electroflotation cell. Therefore, the electrochemical properties of the electrodes must remain stable under changes in operating conditions i.e., resistant to corrosion over a wide range of applied potentials (V) and current densities (A/m$^2$).

Printed Circuit Boards (PCBs)

The first iteration of electrodes used in the EF assembly were custom designed planar, gold electroplated arrays patterned on a custom printed circuit board (PCB) manufactured by OSH-Park (Lake Oswego, OR, USA). PCB's are widely used for electronic assemblies and applications including cell phones, computers, and microelectronics. PCB's support conductive electrical pathways by chemically etching patterns onto copper sheets laminated on non-conductive substrates. OSH-Park uses a typical FR4 epoxy glass as their substrate material. While PCB's may not be commonly used to pattern electrodes, PCB's do offer some unique advantages like custom patterning, relatively low costs, and quick manufacturing.

PCB's can be manufactured with complex electrical pathways through multiple copper conductor layers (typically 2 or 4, but sometimes as many as 16 or more) stacked between layers the dielectric substrate, and interconnected by metallic plated "vias". After the initial printing and lamination of the layers to bind them together the through holes are drilled and electroplated with copper. Although copper is the most common material used in microelectronics, copper is highly susceptible to rapid corrosion oxygen-rich environments (Bui Q. V. et al., 2010, Mater. Res. Bull. 45:305-308). Corrosion is an energetically favorable process converting metals from a high to low energy form (de Leon A. et al., 2015, Intelligent Coatings for Corrosion Control. p. 409-430). Therefore, exposed copper remaining on the circuit board will oxidize and rapidly erode or form a non-conductive oxide layer. To ensure corrosion protection of PCB's, surface finishes are used to protect the copper vias by preventing the formation of a passive oxide, while also providing a solderable surface (Salahinejad, E. et al., 2017, Eng. Fail. Anal. 79:538-546). Common surface finishes including hot air solder leveling (HASL), immersion tin, and electroless nickel immersion gold (ENIG). In the final stages of manufacturing, OSH-Park applies an ENIG surface finish to PCB's. ENIG is a double layer metallic coating of 0.05 $\mu$m-0.2 $\mu$m of gold over 3.04 $\mu$m-6.09 $\mu$m of nickel ENIG has been rated as one of the superior finishes exhibited desirable electrochemical properties like improved electrical interconnections with high conductivity, and supporting high current densities (Bui Q. V. et al., 2010, Mater. Res. Bull. 45:305-308). Inert metals like Au are resistant to corrosion, however the reliability of the Au layer to protect the substrate metals from corrosion largely depends on the thickness, porosity, quality finish and the environmental exposure conditions (Ballantyne, A. et al., 2004, Adv. Colloid Interface Sci. 111:117-29; Bui Q. V. et al., 2010, Mater. Res. Bull. 45:305-308). Degradation of PCB metals due to corrosion remains a challenging issue in electronics despite advances in electroplating surface finishes. Ultimately, corrosion of the surface or substrate metals can result in undesirable shorts or discontinuities in the patterned circuits or complete PCB failure (Fu H. et al. 2015, IEEE, pp 124-129; Salahinejad, E. et al., 2017, Eng. Fail. Anal. 79:538-546). It is notable that the conditions required for electrolysis (i.e., long durations of applied potential across electrode arrays in media containing aqueous electrolytes) are extremely corrosive, such that even relatively "inert" metals like gold can readily be oxidized.

Corrosion Inhibiting Coatings

As previously mentioned, surface finishes are used to protect the mechanical properties of the underlying copper electrical traces from corrosion. However, under harsh conditions such as application of high potentials on electrodes submerged in an electrolyte solution, corrosion is aggressive even on an ENIG surface.

Recently protection of metals and alloys from corrosive environments by conjugated or conductive polymer coatings has been achieved, offering a new area of research for corrosion control methodologies. In 1977, polyaceteylene was doped with iodine to convert the electrically insulating polymer into a material that exhibited high electrical conductivity. The discovery and development of a new class of polymeric materials by doping electrically insulating materials to convert them into electrically conducting polymers (CP) won the Nobel prize in chemistry in 2000 (Zarras, P. et al., 2003, Radiat. Phys. Chem. 68:387-394). Conjugated chains of CPs have repeating units of polymer backbones containing $\pi$-electron networks. There are two main types of doping: oxidative or p-doped where electrons from the backbone are removed resulting in cationic polymers and reductive or n-doped where electrons are added to the backbone resulting in anionic polymers (Angelopoulos, M., 2001, Current 45:57-75; Zarras, P. ct al., 2003, Radiat. Phys. Chem. 68:387-394; Khosla, A. 2012, ECS Interface 21:67-70). The cations and anions formed from the doping of an electron donor or electron acceptor act as charge carriers transforming the material to be electrically conductive. Doping allows the loosely bound electrons to "push" charge across the alternating double bonds of the conjugated polymer resulting in an electrical current through the polymer chain (Rohwerder, M. et al., 2007, Electrochim. Acta 53:1300-1313; Percino, M. J. et al., 2013, John Wiley & Sons, Incorporated). Polyanilines, polypyrrole, polyheterocycles, and poly(phenylene-vinylene) are common classes of CPs and are applied to the surface metal either chemically or electrochemically.

Extensive research has been done on CPs and their application as corrosion inhibiting coatings. While CPs demonstrate potential to prevent corrosion on the EF systems PCB electrode arrays, the application and synthesis of the CPs require complex chemistry and electropolymerization techniques and often volatile materials that are not compatible where autoclaving or other methods are necessary to sterilize surfaces used in molecular diagnostic methods. Despite low manufacturing costs, complicated adhesion of CPs due to incomplete electropolymerization to the metal, and thermal instability result in poor corrosion protection (Breslin C. B. et al., 2005, Mater. Des. 26:233-237). Previously it has been shown (unpublished material) reduced the rate of corrosion of gold electrodes by applying a polypyrrole coating onto the surface, however the corrosion resistance only lasted 20-30 minutes. Taking into consideration the aforementioned complications, CPs were ruled out as viable corrosion inhibiting coatings for the application.

While extensive research was being conducted on CPs in the early 2000's, parallel research was being conducted on electrically conductive pastes and adhesives composed of conducting fillers including carbon, gold and silver, polymer binders (pasting liquids), additives and carriers (Zhang J. et al., 2012, RSC Advances 2.11 (2012): 4787-4791). The principle of conductive pastes is similar to conductive polymers in that ultimately both provide a protective barrier to the electrodes, except the application and synthesis of the conductive paste film to the substrate material is much simpler, reducing the quantity of processing steps. Conductive fillers are homogenously dispersed within the polymeric adhesive matrix to achieve high conductivity throughout the matrix (Švancara, I. et al., 2009, Electroanalysis 21:7-28). Particle-particle contact of additive conductive fillers forms an electrical pathway throughout a normally electrically insulating material. The number and quality of particle-particle interactions determines the resistivity of the matrix and a critical composition for conduction is reached when current can reliably flow through any path in the matrix without reaching an electrically isolated "dead end" (Montemayor, L. C., 2002, Powder Technol. 204:1-10). In contrast, conjugated or conductive polymers rely on electropolymerization to form alternating double and single bonds in the polymer chain enabling electron delocalization throughout the whole matrix (Percino, M. J. et al., 2013, John Wiley & Sons, Incorporated). In this research a screen-printing method was used, where the conductive pastes are patterned in various shapes and thicknesses in a single step to the planar substrate using a screen mask followed by a thermal curing step (Metters J. P. et al., 2013, Sensors Actuators B Chem. 177:1043-1052; Metters J. P. et al., 2012, Sensors Actuators, B Chem. 169:136-143; Moscicki A. et al., 2017, Graphene, Carbon Nanotubes, and Nanostructures. CRC Press, 303-320).

Silver Filled Conductive Epoxy

Silver filled conductive epoxy is a two-part, silver filled, electrically conductive adhesive rated for superior toughness, and high bond strength to similar and dissimilar substrates. EP21TDCS has extremely low volume resistivity ($10^{-3}$ ohm cm$^{-1}$). EP21TDCS does not contain any volatile solvents, which often require extreme curing procedures to eliminate from the compound's matrix.

While silver is not a common electrode material used to support electrolysis, it was hypothesized that its use might confer several distinct advantages in the electroflotation process. Silver/silver chloride (Ag/AgCl) electrodes are one of the most commonly used reference electrodes due to their relatively low standard state redox potential, and highly reversible nature of the Ag/AgCl redox reaction. It was hypothesized that hydrogen could be efficiently evolved at a silver cathode at low electrical potential, while any chloride ions present in the electrolyte could be sequestered on a silver anodic surface. By alternating the potential between two silver electrodes, these processes could potentially be sustained by periodically reversing the chloridation/corrosion on the anodized surfaces. The reversible silver/silver chloride redox reaction conducted at low anodic potentials could inhibit the formation of reactive chlorine species in chloride containing media, helping prevent oxidative damage and lysis of microbial cells.

Media solutions containing chloride are not uncommon in microbial culturing and enrichment processes, including Tris-EDTA and sodium chloride (Winslow, C.-E. A., 1931). The presence of chloride in solutions becomes problematic during electrolysis when a voltage potential greater than 0.81 volts is applied, which is the potential energy required to drive the reaction in water to form hypochlorite (OCl$^-$):

$$Cl_{2(g)} + 2e^- \leftrightarrow 2Cl^- \quad E°=1.35 \text{ V} \quad \text{Eq. 6}$$

$$HClO + H^+ + 2e^- \leftrightarrow Cl^- + H_2O \quad E°=1.482 \text{ V} \quad \text{Eq. 7}$$

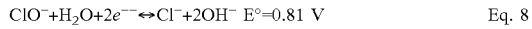

$$ClO^- + H_2O + 2e^- \leftrightarrow Cl^- + 2OH^- \quad E°=0.81 \text{ V} \quad \text{Eq. 8}$$

The formation of hypochlorite decreases the pH of the solution. Hypochlorite is a potent oxidizer and can potentially oxidize or disinfect suspended cells (WHO, 2007). Mitigation of electrochemically generated reactive chlorine species is necessary to prevent cell lysis and death of viable target pathogens so that cells collected by EF are preserved in a more intact state to facilitate detection.

Carbon Conductive Paste (CCP)

Carbon conductive pastes (CCP) have become popular in electrochemistry and have been used for the fabrication of carbon paste electrodes, sensors and detectors. CCP is a mixture of graphite powder and binders including epoxy resins or pasting liquids most commonly in the form of a black baste. Binders are chemically inert, non-volatile and are high viscosity materials (Švancara, I. et al., 2009, Electroanalysis 21:7-28). CCPs physical properties like resistivity can easily be modified depending on the desired application. For example, adding ionic binding materials or chemically active binders in specific proportions facilitates charge transfer through the material. CCP's exhibit phenomenally high conductivity and low ohmic resistance, despite containing electrically insulating binders like silicone or epoxy. The electrochemical processes that enable CCP's high conductivity are not well understood, but are mostly attributed to graphite, a conductive material that is highly resistant to corrosion. Wiping or wetting the top layer of the CCP after electrochemical activity can renew the surface instantaneously, which is an emphasized advantage of the material (Švancara, I. et al., 2009, Electroanalysis 21:7-28).

Conductive Silicone

Conductive silicone is a rubber base with repeating units of poly(dimethyl-siloxane) (PDMS). The elastomer is generally a smooth black paste with a tightly controlled viscosity to assure complete fill-in around complicated contours and complex configurations. Conductive silicone can be filled with metals like silver, copper, or gold to achieve superior conductivity, however these fillers are expensive and also are susceptible to corrosion. Similarly, to CCPs, the electrical conductivity can be achieved by filling or impregnating silicone matrices that normally have a high electrical resistivity ($p=6.3 \times 10^6$) (Halladay, D. et al., 1963, John Wiley and Sons) with graphite to achieve a low resistivity, conductive material state.

PDMS is a popular material suitable for biological applications such as biofilm growth substrate, cell culture, and for the fabrication of microfluidic devices or next generation DNA sequencing where fluid flows with capillary action (Luo, C. et al., 2006, Microelectronics J. 37:1036-1046; Zhao, L. H. et al., 2012, Sensors Actuators, A Phys. 181: 33-42; halldorsson, S. et al., 2015, Biosens. Bioelectron. 63:218-231). Despite the low-cost fabrication of PDMS, applications that use electroosmotic flow to drive or pump fluids across or through PDMS devices, as seen in microfluidics, are challenged by the inherent hydrophobic surface properties of PDMS. The non-polar methyl groups on repeating units of —O—Si(CH$_3$)$_2$— cause the surface of PDMS to exhibit hydrophobic properties with a water contact angle of 105°-120° (Bhattacharya, S. et al., 2005, J. Microelectromechanical Syst. 14:590-597; Almutairi, Z. et al., 2012, Eng. Asp. 415:406-412). Relative to this research, a hydrophobic electrode surface will affect the physiochemical parameters during electrolysis including bubble nucleation, growth and detachment from the surface. The amount of time a bubble occupies a domain on the electrode surface before detaching is regulated by the relative magnitude of surface energies at the gas/electrode and electrolyte/electrode interfaces and, therefore, gas bubbles stick longer and grow larger in size on hydrophobic surfaces (Bouazaze, H. et al., 2006, J. Electroanal. Chem. 597:60-68).

Figure 37:
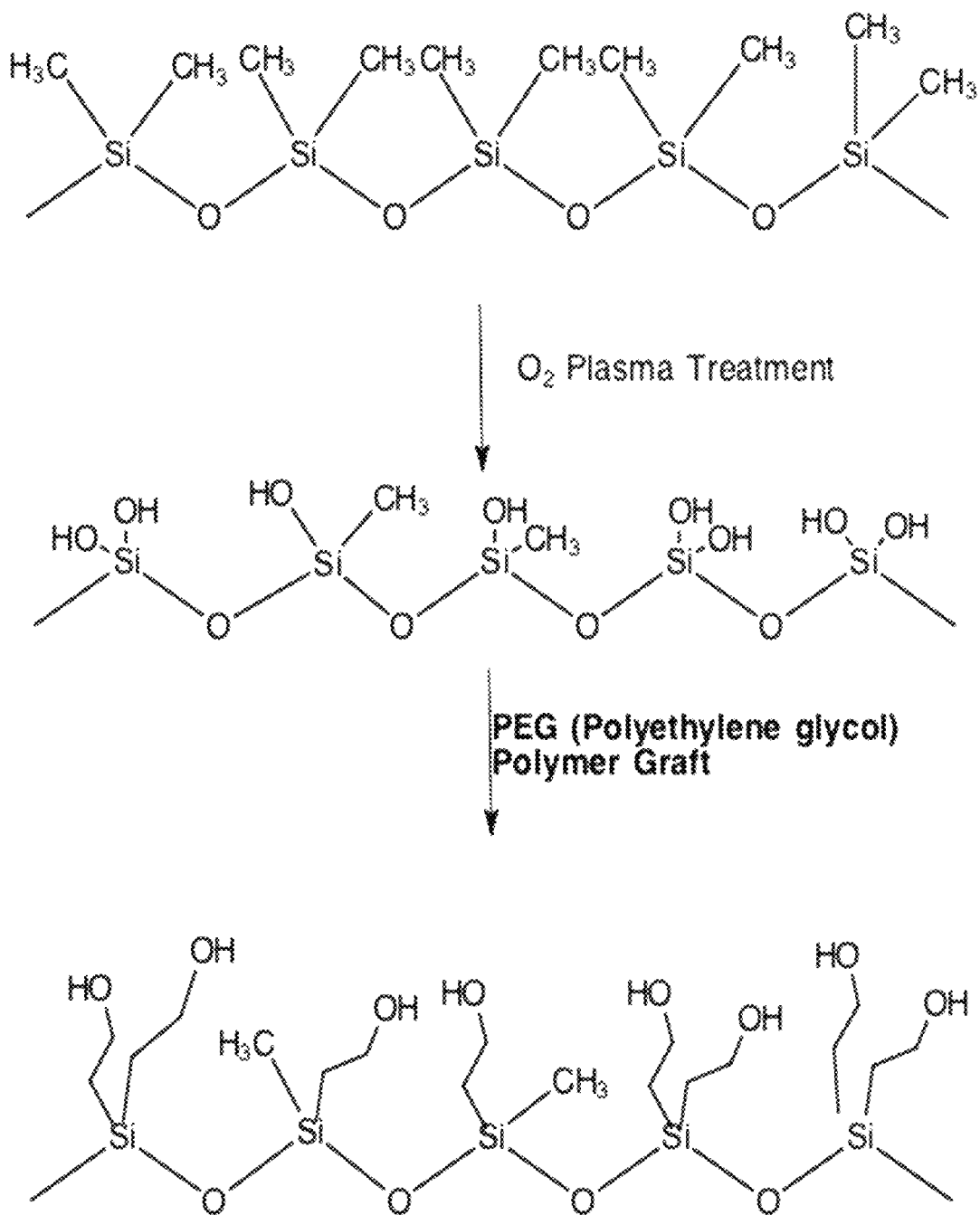
FIG. 37 depicts the mechanism of PDMS hydrophobic to hydrophilic surface modification. $O_2$ plasma treatment followed by PEG grafting.

Given these challenges, extensive research has been done to develop surface treatments to improve the wetting characteristics of PDMS so that the surface is permanently modified to exhibit hydrophilic properties. PDMS surface treatments include chemical and physical techniques like removing uncured oligomers, monomer grafting (Hu, S. et al., 2002, Anal. Chem. 74:4117-4123), and doping PDMS with chemicals (Bodas, D. et al., 2006, Microelectron. Eng. 83:1277-1279; Luo, Y. et al., 2006, Anal. Chem. 78:4588-4592). Among numerous methods of surface modification, extensive studies use oxygen plasma treatment of PDMS for its low cost, rapid and reliable application (Bhattacharya, S. et al., 2005, J. Microelectromechanical Syst. 14:590-597; Bhattacharya, S. et al., 2007, Appl. Surf. Sci. 253:4220-4225; Bodas, D. et al., 2006, Microelectron. Eng. 83:1277-1279; Almutairi, Z. et al., 2012, Eng. Asp. 415:406-412; Hemmila, S. et al., 2012, Appl. Surf. Sci. 258:9864-9875;

Hoffmann, S. et al., 2012, J. Food Prot. 75:1292-1302; Zhao, L. H. et al., 2012, Sensors Actuators, A Phys. 181:33-42). Exposure to oxygen ($O_2$) plasma treatment oxidizes the PDMS surface so that the exposed methyl groups on the repeating —O—Si($CH_3$)$_2$— units are replaced with hydroxyl (—OH) polar groups to form hydrophilic functional silanol groups. Although the one-step $O_2$ plasma surface activation is highly effective, it is not stable over long periods of time resulting in hydrophobic restoration of the PDMS surface within hours to days. The instability of $O_2$ plasma treatment can be attributed to the migration of mobile low molecular weight, uncured polymers containing untreated non-polar siloxane groups rearranging towards the surface of the PDMS (Bhattacharya, S. et al., 2005, J. Microelectromechanical Syst. 14:590-597; Hemmila, S. et al., 2012, Appl. Surf. Sci. 258:9864-9875). Therefore, grafting and tethering additional surface functional groups are necessary to make the hydrophilic modification permanent. Research has shown that grafting polyethylene-glycol (PEG) by physisorption can permanently attach terminal hydroxy groups onto longer chain hydrocarbons that maintain a much more stable orientation on the surface of $O_2$ plasma treated PDMS (Hemmila, S. et al., 2012, Appl. Surf. Sci. 258:9864-9875) (FIG. 37).

Platinum Coated Titanium Electrodes

In the last few decades the chlor-alkali industry has devoted much research to produce electrodes that are not disposable during water treatment and disinfecting processes. H. Beer used metals that remain conductive as oxides and also are robust against anodic polarization (Duby, P., 1993, JOM 45:41-43). Progress in this industry has resulted in lowered manufacturing costs and custom design including patterning and cutting of metals. Commercial companies, like Qi Tin Xi in China who eventually manufactured the electrodes, are able to affordably manufacture prototype volumes of custom electrode designs. Titanium anodes coated with a 5-micron layer of platinum have high anti-corrosion resistance and are therefore not consumed or dissolved during electrolysis, have a long working life, and low operating voltage so that power consumption remains low.

The disclosures of each and every patent, patent application, and publication cited herein are hereby each incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An electroflotation device comprising:
a cylindrical body having a hollow interior, an upper end, and a lower end;
a base sealed to the lower end of the body, wherein the base comprises an electrode array exposed to the hollow interior of the body, the electrode array having a concentric outer array and inner array;
a removable lid connected to the upper end of the body, wherein a hollow core having an open lower end and upper end extends from the lid into the hollow interior of the cylindrical body, such that the hollow core defines an inner space within the hollow core and an outer space between the hollow core and the cylindrical body, and wherein the hollow core extends past a lower rim of the lid for a distance between about 10% and 50% of a height of the body;
wherein the inner space is in vertical alignment with the inner array and the outer space is in vertical alignment with the outer array; and
a microcontroller.

2. The device of claim 1, wherein the open upper end of the hollow core is connected to the lid at a headspace, with a taper terminating in an aperture.

3. The device of claim 2, wherein the aperture comprises a port adaptable with a connector selected from the group consisting of: threaded connectors, luer locks, and stepped connectors.

4. The device of claim 3, wherein the aperture can be connected to an attachment through the port selected from the group consisting of: a dispenser, a filter, a valve, a DNA purification chip, a microfluidic chip, and a spigot.

5. The device of claim 1, wherein the lid comprises an airtight and watertight fitting provided by an O-ring, a rubber flange, or a gasket.

6. The device of claim 1, wherein the outer and inner arrays each comprise at least one anode and at least one cathode.

7. The device of claim 6, wherein the electrodes are arranged in a horizontal pattern of concentric rings alternating between anode and cathode.

8. The device of claim 6, wherein the electrodes are insert molded and permanently fixed into a thermoplastic elastomer base.

9. The device of claim 1, wherein the electrodes are made of a material selected from the group consisting of: platinum, silver, nickel, palladium, gold, copper, iridium, rhodium, and mercury.

10. The device of claim 1, wherein the electrodes are printed circuit boards and comprise a protective surface finish selected from the group consisting of: silver filled conductive epoxy, carbon conductive paste, conductive silicone and platinum coated titanium.

11. The device of claim 1, wherein the device comprises at least one sensor selected from the group consisting of: flow sensors, pressure sensors, liquid level sensors, temperature sensors, pH sensors, volume sensors, level sensors, current sensors, turbidity sensors, conductivity sensors, and voltage sensors.

12. A method of detecting and identifying pathogens, wherein the method comprises the steps of:
providing the electroflotation device according to claim 1;
supplying a sample into the electroflotation device;
energizing the inner array to form upward flowing microbubbles that direct and concentrate sample particulates into the inner space;
energizing both inner and outer arrays so that gas accumulates in the inner and outer spaces and pushes/impels sample particulates in the inner space through the hollow core and out of the lid;
collecting defined volume fractions of the sample particulates through the lid;
performing DNA extraction using an extraction method to release nucleic acids in the volume fraction of the sample particulates;

amplifying the released nucleic acids by a nucleic acid amplification assay; and identifying pathogens using specific primers.

13. The method of claim 12, wherein the nucleic acid amplification assay is selected from the group consisting of: polymerase chain reaction (PCR); strand displacement amplification (SDA); roiling circle amplification (RCA); nucleic acid sequence-based amplification (NASBA), Q-β replicase amplification; helicase-dependent amplification (HAD); loop-mediated isothermal amplification (LAMP); nicking enzyme amplification reaction (NEAR), and recombinase polymerase amplification (RPA).

14. The method of claim 12, wherein the method further comprises a step of pathogen identification using an immunoassay, flow cytometry, or cell senescence assay.

15. The method of claim 12, wherein the sample is selected from the group consisting of: bodily fluids, environmental samples, plant materials, biological warfare agent samples, research samples, irrigation water, agricultural product rinsates, drinking water, waste water, agricultural runoff, food homogenates, aquaponics reflow water, flood water, ocean water, and fresh water.

16. The method of claim 12, wherein the method comprises a further step of contacting the sample with an additive formulation selected from the group consisting of: a flocculant, a surfactant, a pH modifier, and combinations thereof.

17. The method of claim 16, wherein the flocculant is chitosan.

18. The method of claim 16, wherein the surfactant is a polypropylene oxide-polyethylene oxide mixed polymer.

19. The method of claim 16, wherein the pH is adjusted to above 9.5.

* * * * *